(12) United States Patent  
Boudreaux

(10) Patent No.: US 8,979,890 B2
(45) Date of Patent: *Mar. 17, 2015

(54) SURGICAL INSTRUMENT WITH JAW MEMBER

(75) Inventor: Chad P. Boudreaux, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1166 days.

This patent is subject to a terminal disclaimer.

(21) Appl. No.: 12/896,411

(22) Filed: Oct. 1, 2010

(65) Prior Publication Data

US 2012/0083784 A1 Apr. 5, 2012

(51) Int. Cl.
*A61B 18/14* (2006.01)
*A61B 18/00* (2006.01)
*A61B 19/00* (2006.01)

(52) U.S. Cl.
CPC ..... *A61B 18/1445* (2013.01); *A61B 2018/0063* (2013.01); *A61B 2018/1455* (2013.01); *A61B 2019/304* (2013.01)
USPC ............................... 606/207; 606/51; 606/52

(58) Field of Classification Search
CPC ............. A61B 2018/00607; A61B 2018/1455; A61B 18/1445; A61B 18/085
USPC ..................... 606/37, 51, 52, 207
See application file for complete search history.

(56) References Cited

U.S. PATENT DOCUMENTS

| | | |
|---|---|---|
| 2,736,960 A | 3/1956 | Armstrong |
| 2,849,788 A | 9/1958 | Creek |
| 3,015,961 A | 1/1962 | Roney |
| 3,526,219 A | 9/1970 | Balamuth |
| 3,636,943 A | 1/1972 | Balamuth |
| 3,776,238 A | 12/1973 | Peyman et al. |
| 3,805,787 A | 4/1974 | Banko |
| 3,862,630 A | 1/1975 | Balamuth |
| 3,900,823 A | 8/1975 | Sokal et al. |
| 3,918,442 A | 11/1975 | Nikolaev et al. |
| 3,956,826 A | 5/1976 | Perdreaux, Jr. |
| 4,156,187 A | 5/1979 | Murry et al. |

(Continued)

FOREIGN PATENT DOCUMENTS

| | | |
|---|---|---|
| EP | 0443256 A1 | 8/1991 |
| EP | 0456470 A1 | 11/1991 |

(Continued)

OTHER PUBLICATIONS

*Technology Overview*, printed from www.harmonicscalpel.com, Internet site, website accessed on Jun. 13, 2007, (3 pages).

(Continued)

*Primary Examiner* — Joseph Stoklosa
*Assistant Examiner* — Jocelyn D Ram

(57) ABSTRACT

A surgical instrument for supplying energy to tissue may comprise a handle, a trigger, an electrical input, and a shaft extending from the handle. The surgical instrument may comprise an end effector first and second tissue engaging surfaces that are slanted with respect to a transection plane. The end effector may, for example, have an electrode defining a V-shaped cross sectional profile. The end effector may comprise a plurality of raised surfaces that are received by a plurality of indentions when the end effector is in the closed position. The end effector may comprise a cutting member having a plurality of bands.

5 Claims, 40 Drawing Sheets

(56) References Cited

U.S. PATENT DOCUMENTS

| | | |
|---|---|---|
| 4,200,106 A | 4/1980 | Douvas et al. |
| 4,445,063 A | 4/1984 | Smith |
| 4,491,132 A | 1/1985 | Aikins |
| 4,634,420 A | 1/1987 | Spinosa et al. |
| 4,640,279 A | 2/1987 | Beard |
| 4,708,127 A | 11/1987 | Abdelghani |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,922,902 A | 5/1990 | Wuchinich et al. |
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grzeszykowski |
| 5,213,569 A | 5/1993 | Davis |
| 5,221,282 A | 6/1993 | Wuchinich |
| 5,226,910 A | 7/1993 | Kajiyama et al. |
| 5,241,236 A | 8/1993 | Sasaki et al. |
| 5,241,968 A | 9/1993 | Slater |
| 5,257,988 A | 11/1993 | L'Esperance, Jr. |
| 5,261,922 A | 11/1993 | Hood |
| 5,263,957 A | 11/1993 | Davison |
| 5,282,800 A | 2/1994 | Foshee et al. |
| D347,474 S | 5/1994 | Olson |
| 5,322,055 A | 6/1994 | Davison et al. |
| 5,324,299 A | 6/1994 | Davison et al. |
| 5,346,502 A | 9/1994 | Estabrook et al. |
| 5,366,466 A | 11/1994 | Christian et al. |
| D354,564 S | 1/1995 | Medema |
| 5,411,481 A | 5/1995 | Allen et al. |
| 5,419,761 A | 5/1995 | Narayanan et al. |
| 5,421,829 A | 6/1995 | Olichney et al. |
| 5,449,370 A | 9/1995 | Vaitekunas |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,562,609 A | 10/1996 | Brumbach |
| 5,562,610 A | 10/1996 | Brumbach |
| 5,601,601 A | 2/1997 | Tal et al. |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,741,226 A | 4/1998 | Strukel et al. |
| 5,810,859 A | 9/1998 | DiMatteo et al. |
| 5,827,323 A | 10/1998 | Klieman et al. |
| 5,828,160 A | 10/1998 | Sugishita |
| 5,843,109 A | 12/1998 | Mehta et al. |
| 5,879,364 A | 3/1999 | Bromfield et al. |
| 5,893,835 A | 4/1999 | Witt et al. |
| 5,897,569 A | 4/1999 | Kellogg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,989,274 A | 11/1999 | Davison et al. |
| 5,989,275 A | 11/1999 | Estabrook et al. |
| 6,033,375 A | 3/2000 | Brumbach |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,113,594 A | 9/2000 | Savage |
| 6,139,320 A | 10/2000 | Hahn |
| 6,152,902 A | 11/2000 | Christian et al. |
| 6,159,160 A | 12/2000 | Hsei et al. |
| 6,159,175 A | 12/2000 | Strukel et al. |
| 6,206,844 B1 | 3/2001 | Reichel et al. |
| 6,210,403 B1 | 4/2001 | Klicek |
| 6,214,023 B1 | 4/2001 | Whipple et al. |
| 6,233,476 B1 | 5/2001 | Strommer et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,352,532 B1 | 3/2002 | Kramer et al. |
| 6,379,320 B1 | 4/2002 | Lafon et al. |
| 6,383,194 B1 | 5/2002 | Pothula |
| 6,387,109 B1 | 5/2002 | Davison et al. |
| 6,391,042 B1 | 5/2002 | Cimino |
| 6,416,486 B1 | 7/2002 | Wampler |
| 6,423,073 B2 | 7/2002 | Bowman |
| 6,423,082 B1 | 7/2002 | Houser et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,316 B1 | 2/2003 | Nicholson et al. |
| 6,533,784 B2 | 3/2003 | Truckai et al. |
| 6,537,291 B2 | 3/2003 | Friedman et al. |
| 6,543,456 B1 | 4/2003 | Freeman |
| 6,544,260 B1 | 4/2003 | Markel et al. |
| 6,561,983 B2 | 5/2003 | Cronin et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,716,215 B1 | 4/2004 | David et al. |

(56) References Cited

U.S. PATENT DOCUMENTS

| | | | |
|---|---|---|---|
| 6,733,506 B1 | 5/2004 | McDevitt et al. | |
| 6,770,072 B1 | 8/2004 | Truckai et al. | |
| 6,773,444 B2 | 8/2004 | Messerly | |
| 6,786,383 B2 | 9/2004 | Stegelmann | |
| 6,790,216 B1 | 9/2004 | Ishikawa | |
| 6,802,843 B2* | 10/2004 | Truckai et al. | 606/51 |
| 6,828,712 B2 | 12/2004 | Battaglin et al. | |
| 6,869,439 B2 | 3/2005 | White et al. | |
| 6,875,220 B2 | 4/2005 | Du et al. | |
| 6,905,497 B2 | 6/2005 | Truckai et al. | |
| 6,908,472 B2 | 6/2005 | Wiener et al. | |
| 6,913,579 B2* | 7/2005 | Truckai et al. | 600/564 |
| 6,926,716 B2* | 8/2005 | Baker et al. | 606/51 |
| 6,929,632 B2 | 8/2005 | Nita et al. | |
| 6,929,644 B2 | 8/2005 | Truckai et al. | |
| D509,589 S | 9/2005 | Wells | |
| 6,945,981 B2 | 9/2005 | Donofrio et al. | |
| D511,145 S | 11/2005 | Donofrio et al. | |
| 6,976,969 B2 | 12/2005 | Messerly | |
| 6,977,495 B2 | 12/2005 | Donofrio | |
| 6,984,220 B2 | 1/2006 | Wuchinich | |
| 7,011,657 B2 | 3/2006 | Truckai et al. | |
| 7,041,088 B2 | 5/2006 | Nawrocki et al. | |
| 7,041,102 B2 | 5/2006 | Truckai et al. | |
| 7,070,597 B2 | 7/2006 | Truckai et al. | |
| 7,074,219 B2 | 7/2006 | Levine et al. | |
| 7,077,039 B2 | 7/2006 | Gass et al. | |
| 7,077,853 B2 | 7/2006 | Kramer et al. | |
| 7,083,619 B2 | 8/2006 | Truckai et al. | |
| 7,087,054 B2 | 8/2006 | Truckai et al. | |
| 7,108,695 B2 | 9/2006 | Witt et al. | |
| 7,112,201 B2 | 9/2006 | Truckai et al. | |
| 7,118,564 B2 | 10/2006 | Ritchie et al. | |
| 7,125,409 B2 | 10/2006 | Truckai et al. | |
| 7,135,018 B2 | 11/2006 | Ryan et al. | |
| 7,135,030 B2 | 11/2006 | Schwemberger et al. | |
| 7,153,315 B2 | 12/2006 | Miller | |
| 7,156,189 B1 | 1/2007 | Bar-Cohen et al. | |
| 7,156,853 B2 | 1/2007 | Muratsu | |
| 7,157,058 B2 | 1/2007 | Marhasin et al. | |
| 7,159,750 B2 | 1/2007 | Racenet et al. | |
| 7,163,548 B2 | 1/2007 | Stulen et al. | |
| 7,169,146 B2 | 1/2007 | Truckai et al. | |
| 7,179,271 B2 | 2/2007 | Friedman et al. | |
| 7,186,253 B2 | 3/2007 | Truckai et al. | |
| 7,189,233 B2 | 3/2007 | Truckai et al. | |
| 7,204,820 B2 | 4/2007 | Akahoshi | |
| 7,220,951 B2 | 5/2007 | Truckai et al. | |
| 7,223,229 B2 | 5/2007 | Inman et al. | |
| 7,229,455 B2 | 6/2007 | Sakurai et al. | |
| 7,273,483 B2 | 9/2007 | Wiener et al. | |
| 7,309,849 B2 | 12/2007 | Truckai et al. | |
| 7,311,709 B2 | 12/2007 | Truckai et al. | |
| 7,331,410 B2 | 2/2008 | Yong et al. | |
| 7,354,440 B2 | 4/2008 | Truckal et al. | |
| 7,380,695 B2 | 6/2008 | Doll et al. | |
| 7,381,209 B2 | 6/2008 | Truckai et al. | |
| 7,390,317 B2 | 6/2008 | Taylor et al. | |
| 7,408,288 B2 | 8/2008 | Hara | |
| D576,725 S | 9/2008 | Shumer et al. | |
| 7,419,490 B2 | 9/2008 | Falkenstein et al. | |
| D578,643 S | 10/2008 | Shumer et al. | |
| D578,644 S | 10/2008 | Shumer et al. | |
| D578,645 S | 10/2008 | Shumer et al. | |
| 7,431,704 B2 | 10/2008 | Babaev | |
| 7,472,815 B2 | 1/2009 | Shelton, IV et al. | |
| 7,479,148 B2 | 1/2009 | Beaupre | |
| 7,479,160 B2 | 1/2009 | Branch et al. | |
| 7,503,893 B2 | 3/2009 | Kucklick | |
| 7,534,243 B1 | 5/2009 | Chin et al. | |
| D594,983 S | 6/2009 | Price et al. | |
| 7,567,012 B2 | 7/2009 | Namikawa | |
| D618,797 S | 6/2010 | Price et al. | |
| 7,751,115 B2 | 7/2010 | Song | |
| 7,770,774 B2 | 8/2010 | Mastri et al. | |
| 7,780,659 B2 | 8/2010 | Okada et al. | |
| D631,965 S | 2/2011 | Price et al. | |
| 7,901,423 B2 | 3/2011 | Stulen et al. | |
| 2001/0025184 A1 | 9/2001 | Messerly | |
| 2001/0039419 A1 | 11/2001 | Francischelli et al. | |
| 2002/0019649 A1 | 2/2002 | Sikora et al. | |
| 2002/0022836 A1 | 2/2002 | Goble et al. | |
| 2002/0077550 A1 | 6/2002 | Rabiner et al. | |
| 2002/0115997 A1* | 8/2002 | Truckai et al. | 606/51 |
| 2002/0120266 A1* | 8/2002 | Truckai et al. | 606/50 |
| 2002/0156493 A1 | 10/2002 | Houser et al. | |
| 2003/0055443 A1 | 3/2003 | Spotnitz | |
| 2003/0114851 A1* | 6/2003 | Truckai et al. | 606/51 |
| 2003/0199870 A1* | 10/2003 | Truckai et al. | 606/51 |
| 2003/0204199 A1 | 10/2003 | Novak et al. | |
| 2003/0212332 A1 | 11/2003 | Fenton et al. | |
| 2004/0030254 A1 | 2/2004 | Babaev | |
| 2004/0047485 A1 | 3/2004 | Sherrit et al. | |
| 2004/0092921 A1 | 5/2004 | Kadziauskas et al. | |
| 2004/0097919 A1 | 5/2004 | Wellman et al. | |
| 2004/0097996 A1 | 5/2004 | Rabiner et al. | |
| 2004/0199193 A1 | 10/2004 | Hayashi et al. | |
| 2004/0204728 A1 | 10/2004 | Haefner | |
| 2004/0260300 A1 | 12/2004 | Gorensek et al. | |
| 2005/0049546 A1 | 3/2005 | Messerly et al. | |
| 2005/0143769 A1 | 6/2005 | White et al. | |
| 2005/0165345 A1 | 7/2005 | Laufer et al. | |
| 2005/0177184 A1 | 8/2005 | Easley | |
| 2005/0192610 A1 | 9/2005 | Houser et al. | |
| 2005/0209620 A1 | 9/2005 | Du et al. | |
| 2005/0261581 A1 | 11/2005 | Hughes et al. | |
| 2005/0261588 A1 | 11/2005 | Makin et al. | |
| 2005/0288659 A1 | 12/2005 | Kimura et al. | |
| 2006/0030797 A1 | 2/2006 | Zhou et al. | |
| 2006/0063130 A1 | 3/2006 | Hayman et al. | |
| 2006/0069388 A1* | 3/2006 | Truckai et al. | 606/45 |
| 2006/0079878 A1 | 4/2006 | Houser | |
| 2006/0084963 A1 | 4/2006 | Messerly | |
| 2006/0190034 A1 | 8/2006 | Nishizawa et al. | |
| 2006/0211943 A1 | 9/2006 | Beaupre | |
| 2006/0235306 A1 | 10/2006 | Cotter et al. | |
| 2006/0253050 A1 | 11/2006 | Yoshimine et al. | |
| 2007/0016235 A1 | 1/2007 | Tanaka et al. | |
| 2007/0016236 A1 | 1/2007 | Beaupre | |
| 2007/0055228 A1 | 3/2007 | Berg et al. | |
| 2007/0060915 A1 | 3/2007 | Kucklick | |
| 2007/0063618 A1 | 3/2007 | Bromfield | |
| 2007/0129716 A1 | 6/2007 | Daw et al. | |
| 2007/0130771 A1 | 6/2007 | Ehlert et al. | |
| 2007/0131034 A1 | 6/2007 | Ehlert et al. | |
| 2007/0149881 A1 | 6/2007 | Rabin | |
| 2007/0162050 A1 | 7/2007 | Sartor | |
| 2007/0173872 A1 | 7/2007 | Neuenfeldt | |
| 2007/0185380 A1 | 8/2007 | Kucklick | |
| 2007/0219481 A1 | 9/2007 | Babaev | |
| 2007/0249941 A1 | 10/2007 | Salehi et al. | |
| 2007/0265560 A1 | 11/2007 | Soltani et al. | |
| 2007/0275348 A1 | 11/2007 | Lemon | |
| 2007/0282335 A1 | 12/2007 | Young et al. | |
| 2007/0287933 A1 | 12/2007 | Phan et al. | |
| 2008/0009848 A1 | 1/2008 | Paraschiv et al. | |
| 2008/0058585 A1 | 3/2008 | Novak et al. | |
| 2008/0058775 A1 | 3/2008 | Darian et al. | |
| 2008/0058845 A1 | 3/2008 | Shimizu et al. | |
| 2008/0082039 A1 | 4/2008 | Babaev | |
| 2008/0082098 A1 | 4/2008 | Tanaka et al. | |
| 2008/0172051 A1 | 7/2008 | Masuda et al. | |
| 2008/0177268 A1 | 7/2008 | Daum et al. | |
| 2008/0188878 A1 | 8/2008 | Young | |
| 2008/0200940 A1 | 8/2008 | Eichmann et al. | |
| 2008/0208231 A1 | 8/2008 | Ota et al. | |
| 2008/0234708 A1 | 9/2008 | Houser et al. | |
| 2008/0234709 A1 | 9/2008 | Houser | |
| 2008/0234710 A1 | 9/2008 | Neurohr et al. | |
| 2008/0234711 A1 | 9/2008 | Houser et al. | |
| 2008/0262490 A1 | 10/2008 | Williams | |
| 2008/0281200 A1 | 11/2008 | Voic et al. | |
| 2008/0287948 A1 | 11/2008 | Newton et al. | |
| 2009/0030311 A1 | 1/2009 | Stulen et al. | |

(56) References Cited

U.S. PATENT DOCUMENTS

| | | |
|---|---|---|
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0143795 A1 | 6/2009 | Robertson |
| 2009/0143806 A1 | 6/2009 | Witt et al. |
| 2010/0036370 A1 | 2/2010 | Mirel et al. |
| 2010/0036405 A1 | 2/2010 | Giordano et al. |
| 2010/0179577 A1 | 7/2010 | Houser |
| 2010/0187283 A1 | 7/2010 | Crainich et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0238065 A1* | 9/2011 | Hunt et al. .................. 606/45 |
| 2012/0022525 A1* | 1/2012 | Dietz et al. .................. 606/45 |
| 2012/0083783 A1* | 4/2012 | Davison et al. ............. 606/45 |
| 2013/0030433 A1* | 1/2013 | Heard ........................... 606/45 |
| 2013/0079762 A1* | 3/2013 | Twomey et al. ............. 606/29 |

FOREIGN PATENT DOCUMENTS

| | | |
|---|---|---|
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 1199044 B1 | 12/2005 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| WO | WO 92/22259 A2 | 12/1992 |
| WO | WO 98/37815 A1 | 9/1998 |
| WO | WO 01/54590 A1 | 8/2001 |
| WO | WO 2005/122917 A1 | 12/2005 |
| WO | WO 2006/042210 A2 | 4/2006 |
| WO | WO 2006/119139 A2 | 11/2006 |
| WO | WO 2006/129465 A1 | 12/2006 |
| WO | WO 2007/047531 A2 | 4/2007 |
| WO | WO 2007/143665 A2 | 12/2007 |
| WO | WO 2009/027065 A1 | 3/2009 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,420, filed Oct. 1, 2010.

F. A. Duck, "Optical Properties of Tissue Including Ultravioelt and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

Campbell et al, "Thermal Imaging in Surgery," p. 19-3, in *Medical Infrared Imaging*, N. A. Diakides and J. D. Bronzino, Eds. (2008).

International Search Report for PCT/US2011/053413, dated Jul. 2, 2013 (4 pages).

Written Opinion for PCT/US2011/053413, dated Jul. 2, 2013 (4 pages).

\* cited by examiner

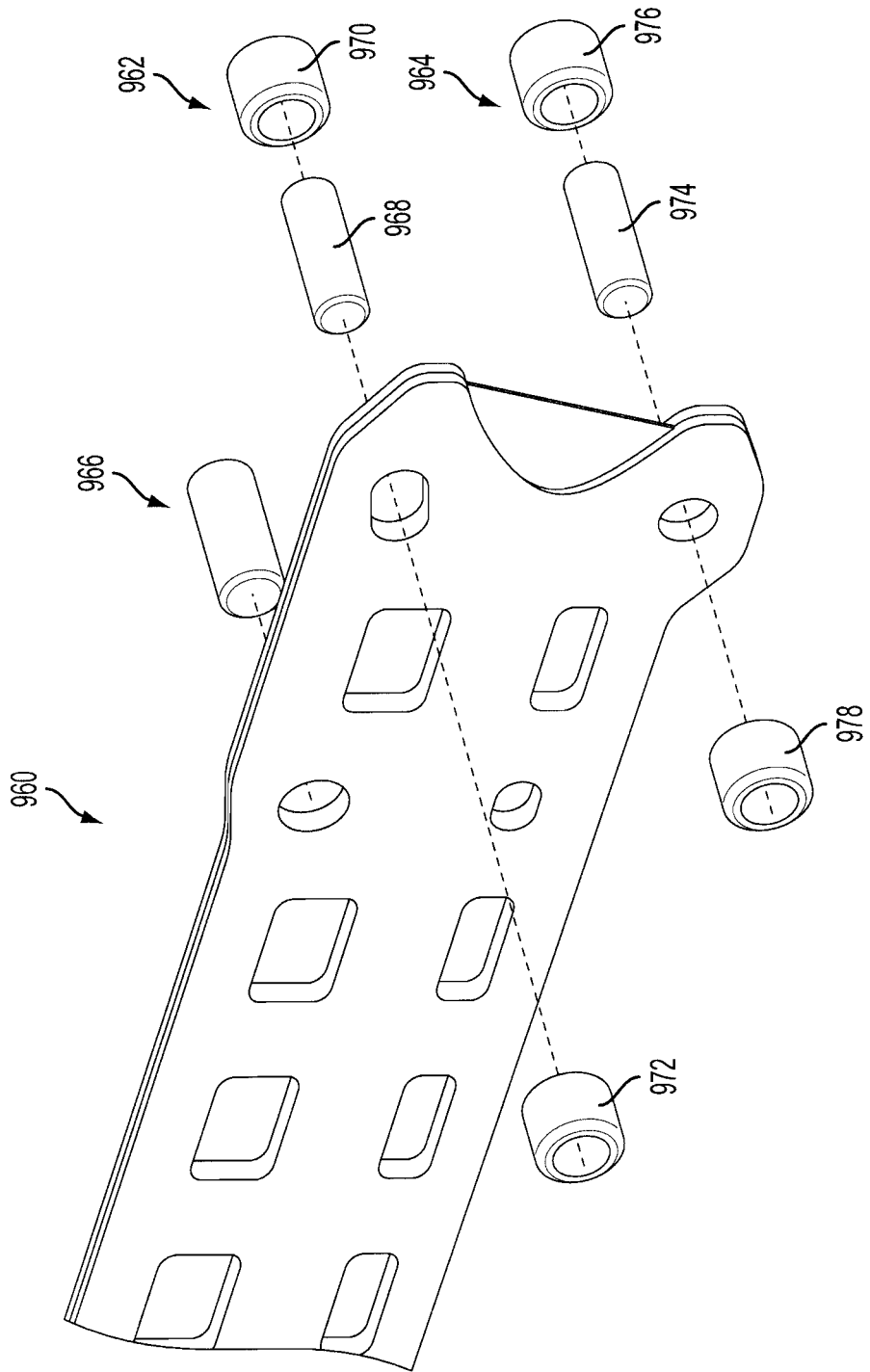

SURGICAL INSTRUMENT WITH JAW MEMBER

BACKGROUND

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow through the electrodes and into the tissue. The surgical instrument can further comprise an electrical input, a supply conductor electrically coupled with the electrodes, and/or a return conductor which can be configured to allow current to flow from the electrical input, through the supply conductor, through the electrodes and tissue, and then through the return conductor to an electrical output, for example. In various circumstances, the energy can generate heat within the captured tissue to create one or more hemostatic seals within the tissue. Such embodiments may be particularly useful for sealing blood vessels, for example. The surgical instrument can further comprise a cutting member which can be moved relative to the tissue and electrodes in order to transect the tissue.

The foregoing discussion is intended only to illustrate various aspects of the related art in the field of the invention at the time, and should not be taken as a disavowal of claim scope.

SUMMARY

In accordance with various embodiments, a surgical instrument for supplying energy to tissue may comprise a handle. The handle may comprise a trigger, an electrical input, and a shaft extending from the handle. The shaft may comprise a conductor. The trigger may be selectively actuatable to electrically couple the electrical input and the conductor. The surgical instrument may comprise an end effector defining a longitudinal axis and a transection plane. The end effector may comprise a first jaw member and a second jaw member. At least one of the first jaw member and the second jaw member may be movable relative to the other of the first jaw member and the second jaw member to clamp tissue intermediate the first jaw member and the second jaw member. The end effector may further comprise an electrode electrically coupled with the conductor and first and second tissue engaging surfaces coupled to one of the first and second jaw members and extending along the longitudinal axis. Each of the first and second tissue engaging surfaces may have an inner portion and an outer portion, wherein the first and second tissue engaging surfaces are slanted with respect to the transection plane.

In accordance with various embodiments, a surgical instrument for supplying energy to tissue may comprise a handle. The handle may comprise a trigger and an electrical input. A shaft may extend from the handle, wherein the shaft comprises a conductor, and wherein the trigger is selectively actuatable to electrically couple the electrical input and the conductor. The surgical instrument may comprise an end effector defining a longitudinal axis and comprising a first jaw member and a second jaw member. At least one of the first jaw member and the second jaw member may be movable relative to the other of the first jaw member and the second jaw member between an open and closed positions to clamp tissue intermediate the first jaw member and the second jaw member in the closed position. The end effector may comprise a passive electrode having a passive electrode tissue contacting surface and an active electrode having a first active electrode tissue contacting surface and a second active electrode tissue contacting surface. The active electrode may be electrically coupled with the conductor and the first active electrode tissue contacting surface may be generally parallel to the passive electrode tissue contacting surface in the closed position. The second active electrode tissue contacting surface may be generally oblique to the passive electrode tissue contacting surface in the closed position.

In accordance with various embodiments, a surgical instrument for supplying energy to tissue may comprise a handle that comprises a trigger and an electrical input. The surgical instrument may comprise a shaft extending from the handle, wherein the shaft comprises a conductor, and wherein the trigger is selectively actuatable to electrically couple the electrical input and the conductor. The surgical instrument may comprise an end effector defining a longitudinal axis. The end effector may comprise a first jaw member and a second jaw member. At least one of the first jaw member and the second jaw member may be movable relative to the other of the first jaw member and the second jaw member between open and closed positions to clamp tissue intermediate the first jaw member and the second jaw member in the closed position. The end effector may further comprise a first electrode coupled with the conductor. The first electrode may comprise a plurality of raised surfaces. A tissue contacting surface may oppose the first electrode in the closed position, wherein the tissue contacting surface may define a plurality of indentations. The indentations may be positioned to receive the plurality of raised surfaces when the first and second jaw members are in the closed position.

In accordance with various embodiments, a surgical instrument for supplying energy to tissue may comprise a trigger, an electrical input, and a shaft extending from the handle. The shaft may comprise a conductor and the trigger may be selectively actuatable to electrically couple the electrical input and the conductor. The surgical instrument may further comprise an end effector defining a longitudinal axis. The end effector may comprise a first jaw member and a second jaw member. At least one of the first jaw member and the second jaw member may be movable relative to the other of the first jaw member and the second jaw member between open and closed positions to clamp tissue intermediate the first jaw member and the second jaw member in the closed position. The first and second jaw members may define a channel. The end effector may comprise a cutting member including a distal end, wherein the cutting member is sized and configured to fit at least partially within the channel. The cutting member may be configured to translate along the channel between a retracted position and a fully advanced position. The cutting member may comprise at least a first, second, and third bands, wherein the second band is disposed intermediate the first and third bands and comprises a sharp distal cutting element. The end effector may further comprise at least one compression element extending from the cutting member, wherein the at least one compression element engages one of the first and second jaws to move the first and second jaws from the open position to the closed position when the cutting member translates with respect to the first jaw member beyond the retracted position.

In accordance with various embodiments, a surgical instrument for supplying energy to tissue may comprise a handle, a trigger, an electrical input, and a shaft extending from the handle. The shaft may comprise a conductor and the trigger may be selectively actuatable to electrically couple the electrical input and the conductor. The surgical instrument may comprise an end effector defining a longitudinal axis. The end effector may comprise a first jaw member comprising a cammed compression surface along the longitudinal axis and a second jaw member, wherein at least one of the first jaw member and the second jaw member is movable relative to the other of the first jaw member and the second jaw member between an open and a closed position to clamp tissue intermediate the first jaw member and the second jaw member in the closed position. The first and second jaw members may define a channel. The end effector may comprise a cutting member including a distal end, wherein the cutting member is sized and configured to fit at least partially within the channel. The cutting member may be configured to translate along the channel between a retracted position and a fully advanced position. The end effector may comprise at least one compression element extending from the cutting member and contacting the cammed compression surface, wherein the at least one compression element engages the cammed compression surface to move the first and second jaws from the open position to the closed position when the cutting member translates with respect to the first and second jaw members beyond the retracted position.

In accordance with various embodiments, a surgical instrument for supplying energy to tissue may comprise a handle, a trigger, and an electrical input. The surgical instrument may comprise a shaft extending from the handle, wherein the shaft comprises a conductor, and wherein the trigger is selectively actuatable to electrically couple the electrical input and the conductor. The surgical instrument may comprise an end effector defining a longitudinal axis. The end effector may comprise a first jaw member comprising a cammed compression surface along the longitudinal axis and a second jaw member. At least one of the first jaw member and the second jaw member may be movable relative to the other of the first jaw member and the second jaw member between an open and a closed position to clamp tissue intermediate the first jaw member and the second jaw member in the closed position. The first and second jaw members may define a channel. The end effector may further comprise a cutting member including a distal end, wherein the cutting member is sized and configured to fit at least partially within the channel. The cutting member may be configured to translate along the channel between a retracted position and a fully advanced position with the cutting member defining a transection plane. The end effector may further comprise an electrode comprising a tapered tissue contacting surface.

In accordance with various embodiments, a surgical instrument for supplying energy to tissue may comprise a handle that comprises a trigger, an overload member operatively coupled to the trigger, and an electrical input. The surgical instrument may further comprise a shaft extending from the handle, wherein the shaft comprises a conductor, and wherein the trigger is selectively actuatable to electrically couple the electrical input and the conductor. The surgical instrument may comprise an end effector defining a longitudinal axis and comprising a first jaw member and a second jaw member. At least one of the first jaw member and the second jaw member may be movable relative to the other of the first jaw member and the second jaw member to clamp tissue intermediate the first jaw member and the second jaw member. The end effector may further comprise an electrode electrically coupled with the conductor.

In accordance with various embodiments, a surgical instrument for supplying energy to tissue may comprise a handle, a trigger, an electrical input, and a shaft extending from the handle. The shaft may comprise a conductor and the trigger may be selectively actuatable to electrically couple the electrical input and the conductor. The surgical instrument may comprise an end effector defining a longitudinal axis. The end effector may comprise a first jaw member comprising a cammed compression surface along the longitudinal axis and a second jaw member. At least one of the first jaw member and the second jaw member may be movable relative to the other of the first jaw member and the second jaw member between an open and a closed position to clamp tissue intermediate the first jaw member and the second jaw member in the closed position. The first and second jaw member may define a channel. The end effector may comprise a cutting member including a distal end, wherein the cutting member is sized and configured to fit at least partially within the channel. The cutting member may be configured to translate along the channel between a retracted position and a fully advanced position. The cutting member may comprise a first compression element and a second compression element separated by a distance. The first compression element may be engagable to the first jaw member and the second compression element engagable to the second jaw member, wherein the first compression element is moveable relative to the cutting member.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 30 is a perspective exploded view of a movable cutting member comprising closure pin assemblies in accordance with one non-limiting embodiment.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
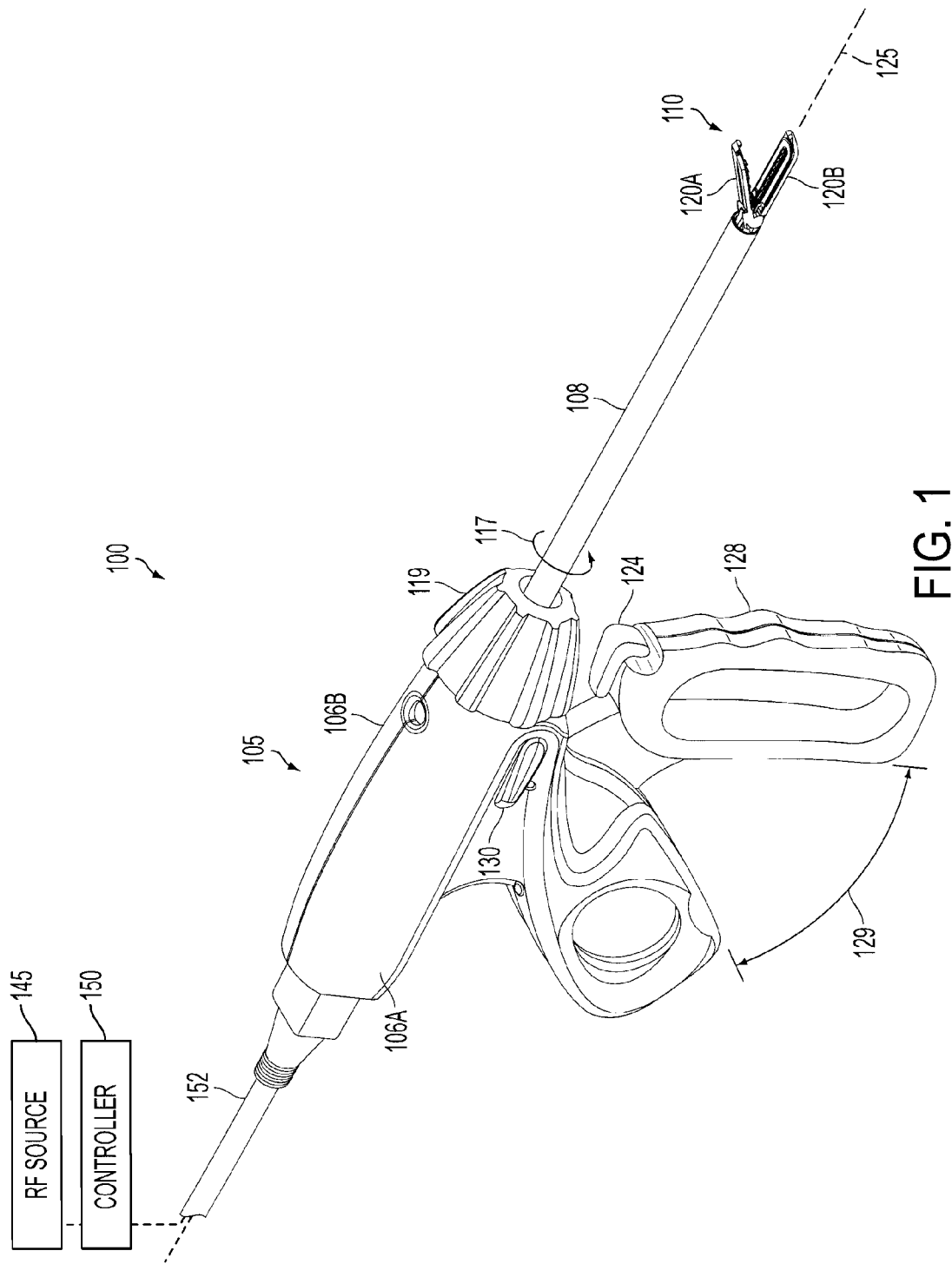
FIG. 1 is a perspective view of a surgical instrument illustrated in accordance with at least one embodiment.

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments.

However, surgical instruments may be used in many orientations and positions, and these terms are not intended to be limiting and absolute.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Various embodiments of systems and methods relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to ensure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

A surgical instrument can be configured to supply energy, such as electrical energy, ultrasonic energy, and/or heat energy, for example, to the tissue of a patient. For example, various embodiments disclosed herein provide electrosurgical jaw structures adapted for transecting captured tissue between the jaws and for contemporaneously welding or sealing the captured tissue margins with controlled application of RF energy. Surgical instruments may also be configured to, for example, grasp, sever, and staple tissue.

In more detail, in various embodiments, referring now to FIG. 1, an electrosurgical instrument 100 is shown. The surgical or electrosurgical instrument 100 may comprise a proximal handle 105, a distal working end or end effector 110 and an introducer or elongate shaft 108 disposed in-between and at least partially operably coupling the handle 105 to the end effector 110. The end effector 110 may comprise a set of openable-closeable jaws with straight or curved jaws—an upper first jaw 120A and a lower second jaw 120B. The jaws 120A and 120B may be operably coupled together such that the first jaw 120A may move between an open position and a closed position with respect to the second jaw 120B. First jaw 120A and second jaw 120B may each comprise an elongate slot or channel 142A and 142B (see FIG. 3), respectively, disposed outwardly along their respective middle portions. The first jaw 120A and the second jaw 120B may be coupled to an electrical source 145 and a controller 150 through electrical leads in the cable 152. The controller 150 may be used to activate the electrical source 145. In various embodiments, the electrical source 145 may comprise an RF source, an ultrasonic source, a direct current source, and/or any other suitable type of electrical energy source, for example.

Figure 2:
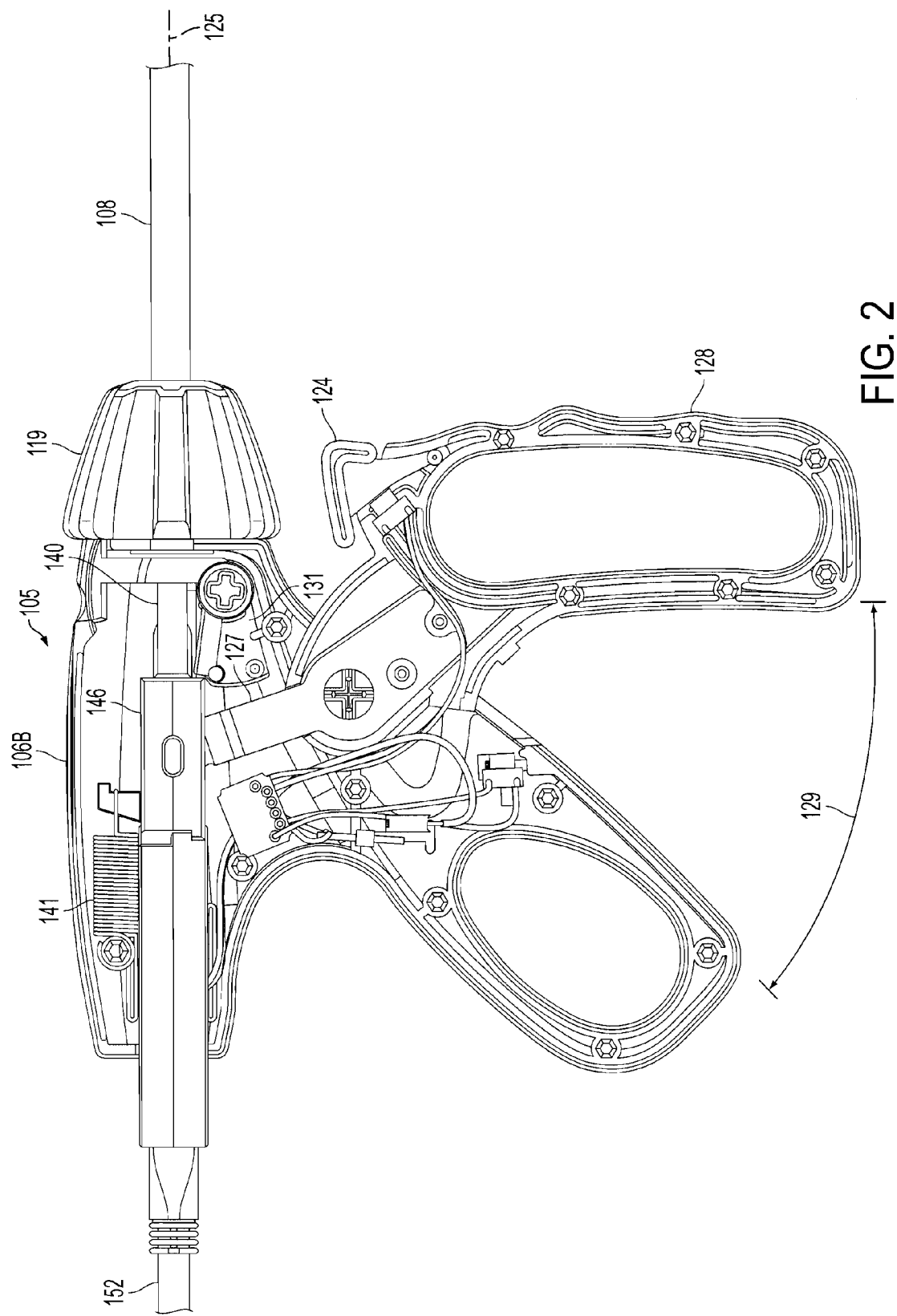
FIG. 2 is a side view of a handle of the surgical instrument of FIG. 1 with a half of a handle body removed to illustrate some of the components therein.

Moving now to FIG. 2, a side view of the handle 105 is shown with half of the first handle body 106A (see FIG. 1) removed to illustrate some of the components within the second handle body 106B. The handle 105 may comprise a lever arm or trigger 128 extending from the handle body 106A and/or 106B. The trigger 128 may be pulled along a path 129 such that the trigger 128 moves with respect to the body 106A and/or 106B. The trigger 128 may also be operably coupled to a movable cutting member 140 disposed within the elongate shaft 108 by a shuttle 146 operably engaged to an extension 127 of the trigger 128. Accordingly, movement of the trigger 128 relative to the handle body 106A and/or 106B may cause the cutting member 140 to translate with respect to one or both of the jaws 120A and 120B (see FIG. 1). Also, as described in more detail below, the cutting member 140 may be releasably engaged with a closure beam 170 (see FIGS. 3-4) that is also movably associated with the jaws 120A, 120B. The shuttle 146 may further be connected to a biasing device, such as a spring 141, which may also be connected to the second handle body 106B, to bias the shuttle 146 and thus the cutting member 140 and/or the closure beam 170 (FIG. 3) in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers or sliders for actuating the first jaw 120A and the second jaw 120B. The elongate shaft 108 may have a cylindrical or rectangular cross-section and can comprise a thin-wall tubular sleeve that extends from the handle 105. The elongate shaft 108 may include a bore extending therethrough for carrying actuator mechanisms, such as the cutting member 140 and/or the closure beam 170, for example, for actuating the jaws and for carrying electrical leads for delivery of electrical energy to electrosurgical components of the end effector 110.

The end effector 110 may be adapted for capturing, welding or sealing, and transecting tissue. The first jaw 120A and the second jaw 120B may close to thereby capture or engage tissue about a longitudinal axis 125 defined by the cutting member 140. The first jaw 120A and the second jaw 120B may also apply compression to the tissue. The elongate shaft 108, along with the first jaw 120A and the second jaw 120B, can be rotated a full 360 degrees, as shown by arrow 117, relative to the handle 105 through, for example, a rotary triple contact. The first jaw 120A and the second jaw 120B can remain openable and/or closeable while rotated. In some embodiments, a collar 119, or other rotational control device, may be manipulated by the user to rotate the end effector 110.

Figure 4:
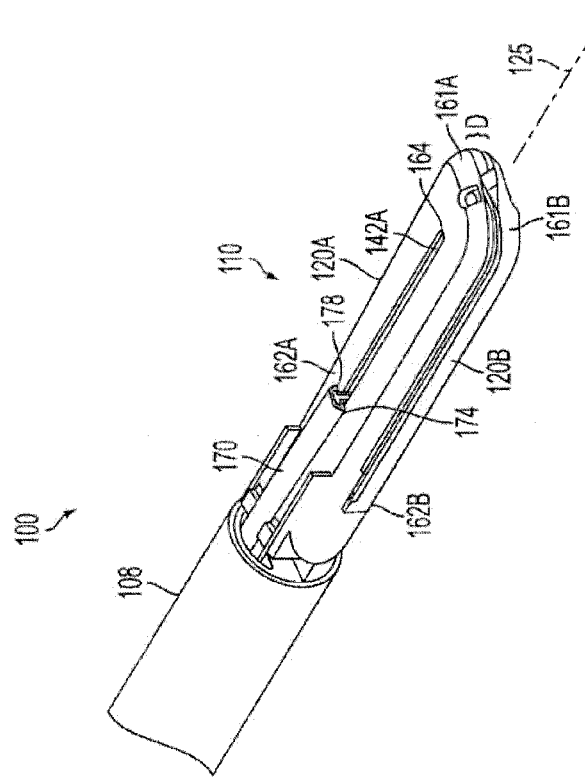
FIG. 4 is a perspective view of the end effector of the surgical instrument of FIG. 1 illustrated in a closed configuration; the distal end of the closure beam is illustrated in a partially advanced position.
Figure 3:
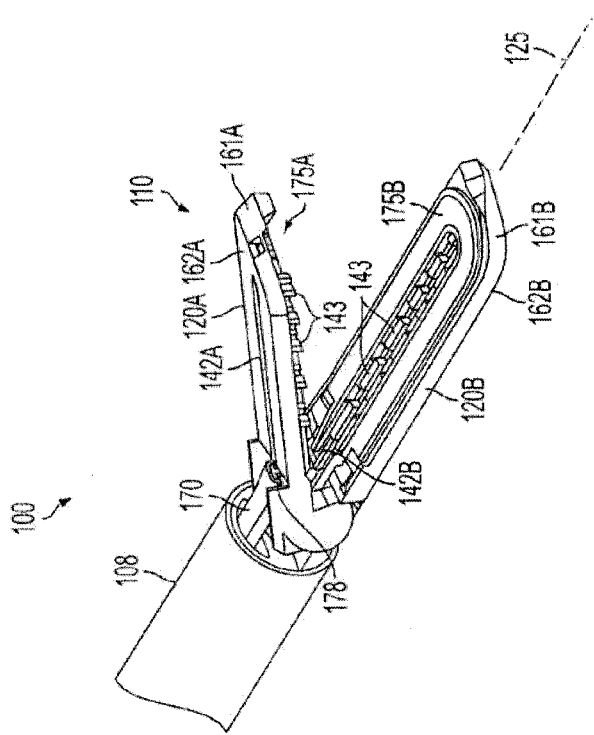
FIG. 3 is a perspective view of an end effector of the surgical instrument of FIG. 1 illustrated in an open configuration; the distal end of a closure beam is illustrated in a retracted position.

FIGS. 3 and 4 illustrate perspective views of the end effector 110. FIG. 3 shows the end effector 110 in an open configuration and FIG. 4 shows end effector 110 in a closed configuration. As noted above, the end effector 110 may comprise the upper first jaw 120A and the lower second jaw 120B. Further, the first jaw 120A and second jaw 120B may each have tissue-gripping elements, such as teeth 143, disposed on the inner portions of first jaw 120A and second jaw 120B. The first jaw 120A may comprise an upper first jaw body 161A with an upper first outward-facing surface 162A and an upper first energy delivery surface 175A of a first electrode, for example. The second jaw 120B may comprise a lower second jaw body 161B with a lower second outward-facing surface 162B and a lower second energy delivery surface 175B of a second electrode, for example. The first energy delivery surface 175A and the second energy delivery surface 175B may both extend in a "U" shape about the distal end of end effector 110. The energy delivery surfaces 175A, 175B may provide a tissue contacting surface or surfaces for contacting, gripping, and/or manipulating tissue therebetween.

Figure 5:
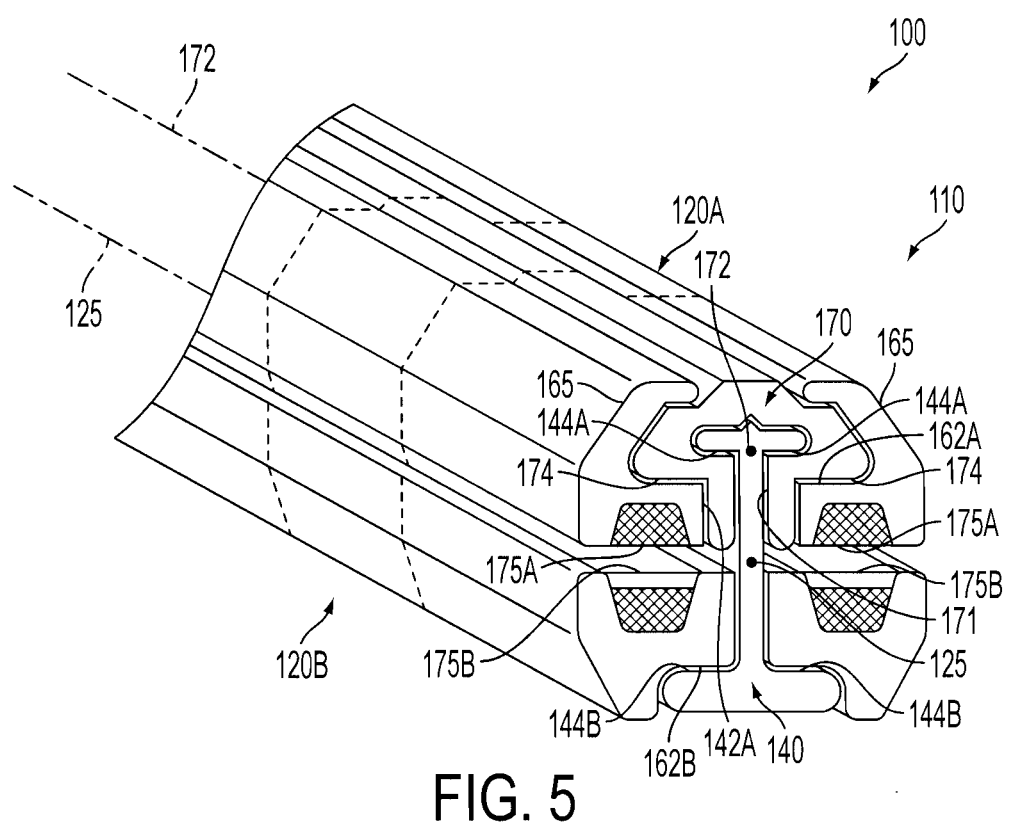
FIG. 5 is a perspective cross-sectional view of a portion of an end effector of the surgical instrument of FIG. 1.

Referring to FIGS. 3-5, in at least one embodiment, the closure beam 170 and the cutting member 140 may be sized and configured to fit at least partially within the channel 142A of the first jaw 120A. As seen in FIG. 5, the cutting member 140 may also be sized and configured to fit at least partially within the channel 142B of the second jaw 120B. In any event, the closure beam 170 and the cutting member 140 may translate along the channel 142A between a first, retracted position correlating with the first jaw being at the open position (FIG. 3), and a second, advanced position correlating with the second jaw being at the closed position (see, for example, FIG. 4). The trigger 128 of handle 105, see FIG. 2, may be adapted to actuate the cutting member 140 and, subsequently, the closure beam 170, which also functions as a jaw-closing mechanism. For example, the cutting member 140 and/or closure beam 170 may be urged distally as the trigger 128 is pulled proximally along the path 129 via the shuttle 146, seen in FIG. 2 and discussed above. The cutting member 140 and the closure beam 170 may each comprise one or several pieces, but in any event, may each be movable or translatable with respect to the elongate shaft 108 and/or the jaws 120A, 120B. Also, in at least one embodiment, the cutting member 140 may be made of 17-4 precipitation hardened stainless steel, for example. In one embodiment, at least a portion of the cutting member 140 is 716 stainless steel. The distal portion of the cutting member 140 may comprise a flanged "I"-beam configured to slide within the channels 142A and 142B in jaws 120A and 120B. In at least one embodiment, the distal portion of the closure beam 170 may comprise a "C"-shaped beam configured to slide within one of channels 142A and 142B. As illustrated in FIGS. 3-5, the closure beam is shown residing in and/or on the channel 142A of the first jaw 120A. The closure beam 170 may slide within the channel 142A, for example, to open and close the first jaw 120A with respect to the second jaw 120B. The distal portion of the closure beam 170 may also define inner cam surfaces 174 for engaging outward facing surfaces 162A of the first jaw 120A, for example. Accordingly, as the closure beam 170 is advanced distally through the channel 142A, from, for example, a first position (FIG. 3) to a second position (FIG. 4), the first jaw 120A may be urged closed (FIG. 4). The closure beam 170 may also be guided by upper walls 165 of the first jaw 120A, which as seen in FIG. 5 may at least partially envelope the closure beam 170. The upper walls 165 have been omitted from FIGS. 3-4 for purposes of clarity.

Additionally, in various embodiments, the cutting member 140 may be sized and configured to at least partially fit or slide within the closure beam 170, such as within an inner channel 171 of the closure beam 170, for example. In at least one embodiment, as seen in FIG. 5, while part of the cutting member 140 may be positioned within the closure beam 170, a portion of the cutting member 140 may protrude from the closure beam 170 in a direction transverse to a longitudinal axis 172 defined by the closure beam 170. The flanges 144A and 144B of cutting member 140 may define inner cam surfaces for engaging the inner channel 171 of the closure beam 170 and the outward facing surfaces 162B of the second jaw 120B. As discussed in greater detail below, the opening and closing of jaws 120A and 120B can apply very high compressive forces on tissue using cam mechanisms which may include reciprocating "C-beam" closure beam 170 and/or "I-beam" cutting member 140 and the outward facing surfaces 162A, 162B of jaws 120A, 120B.

More specifically, referring still to FIGS. 3-5, collectively, the flanges 144A and 144B of the distal end of the cutting member 140 may be adapted to slidably engage the inner channel 171 of the closure beam 170 and the second outward-facing surface 162B of the second jaw 120B, respectively. The channel 142A within the first jaw 120A and the channel 142B within the second jaw 120b may be sized and configured to accommodate the movement of closure beam 170 and/or the cutting member 140, which may comprise a tissue-cutting element, for example, a sharp distal edge and/or surface. FIG. 4, for example, shows the distal end 178 of the closure beam 170 advanced at least partially through the channel 142A. The advancement of the closure beam 170 can close the end effector 110 from the open configuration shown in FIG. 3 to the closed configuration shown in FIG. 4. The closure beam 170 may move or translate along the channel 142A between a first, retracted position and a second, fully advanced position. The retracted position can be seen in FIG. 3, where the jaws 120A, 120b are in an open position and a distal end 178 of the closure beam 170 is positioned proximal to the upper outward-facing surface 162A. The fully advanced position, while not shown, may occur when the distal end 178 of the closure beam 170 is advanced to a distal end 164 of the channel 142A and the jaws are in a closed position, see FIG. 4. Likewise, the cutting member 140 (FIG. 5) may be configured to translate with respect to the first jaw between a retracted position, where the jaws 120A, 120B are in an open position (FIG. 3) and a fully advanced position where the cutting member is advanced to the distal end 164 of the channel 142A, for example, with the jaws in a closed position (FIG. 4). As noted above, the cutting member 140 may also translate with respect to the closure beam 170 as the closure beam 170 is being advanced through the jaws 120A, 120B.

In at least one embodiment, distal portions of the closure beam 170 and the cutting member 140 may be positioned within and/or adjacent to one or both of the jaws 120A and 120B of the end effector 110 and/or distal to the elongate shaft 108. Further, in the closed position shown by FIG. 4, the upper first jaw 120A and the lower second jaw 120B define a gap or dimension D between the first energy delivery surface 175A and the second energy delivery surface 175B of the first jaw 120A and the second jaw 120B, respectively. Dimension D may equal from about 0.0005" to about 0.040", for example, and in some embodiments may equal about 0.001" to about 0.010", for example. Also, the edges of first energy delivery surface 175A and second energy delivery surface 175B may be rounded to prevent the dissection of tissue.

Referring now to FIGS. 1 and 3, the end effector 110 may be coupled to the electrical source 145 and the controller 150. The first energy delivery surface 175A and the second energy delivery surface 175B may likewise each be coupled to electrical source 145 and the controller 150. The first energy delivery surface 175A and the second energy delivery surface 175B may be configured to contact tissue and deliver electrosurgical energy to engaged tissue which is adapted to seal or weld the tissue. The controller 150 can regulate the electrical energy delivered by the electrical source 145 which in turn delivers electrosurgical energy to the first energy-delivery surface 175A and the second energy-delivery surface 175B. The energy delivery may be initiated by an activation button 124 operably engaged with the trigger 128 and in electrical communication with the controller 150 via the cable 152. As mentioned above, the electrosurgical energy delivered by the electrical source 145 may comprise radiofrequency (RF) energy, or other suitable forms of energy. Further, in some embodiments, at least one of the opposing first and second energy delivery surfaces 175A and 175B may carry variable resistive positive temperature coefficient (PTC) bodies. In one embodiment, the first energy delivery surface 175A comprises a passive electrode and the second energy delivery surface 175B comprises an active electrode. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

With some electrosurgical devices, obtaining effective ligation on single vessels and large tissue bundles may be difficult. One type of commonly observed failure is tissue rupturing along the inner and outer edges of a seal. Tissue rupture may be the result of unequal compression between the vessel walls being approximated. Furthermore, due to the high concentration of electrical current, tissue within an active electrode contact zone and zones immediately lateral to this zone liquefy to a coagulum material. As the jaws approximate the vessel walls, pressure is resisted by the intact "unaffected" tissue while the amorphous coagulum is ruptured. Additionally, high stress concentration at the outer edge of the jaw, high stress concentration at the inner edge of the knife slot, unequal distribution of thermal activity at the area between the active electrode and the outer wall as well as the inner wall contact surfaces on the upper jaw and lower jaw may also contribute to tissue rupture.

Another type of commonly observed failure includes tissue within the knife slot remaining unaffected after completion of the RF energy cycle. Such a failure may lead to difficulty cutting tissue to obtain proper transection and may also negatively impact seal integrity. Furthermore, in some instances, tissue may inadvertently be charred locally at an area in direct contact with the active electrode surface. The localized heating may cause limited formation of coagulum and subsequent desiccation of the greater seal volume. The tissue within this locally heated zone becomes desiccated too quickly, before the current and therefore temperature is distributed to the rest of the seal volume.

Figure 6:
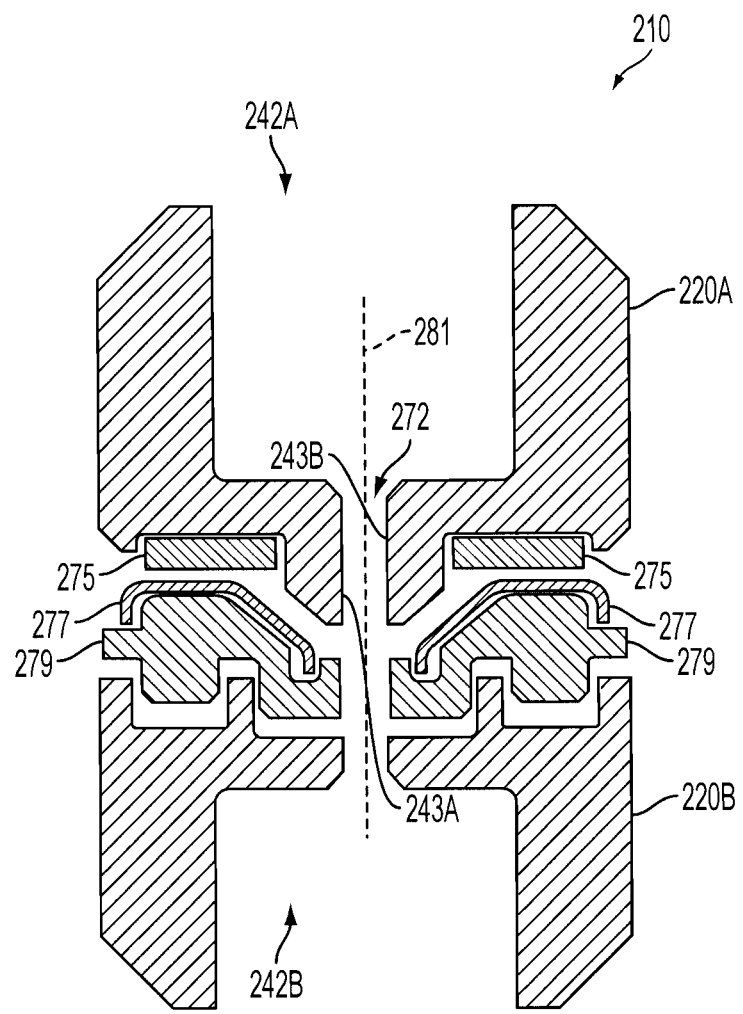
FIG. 6 is a cross-sectional view of an end effector in accordance with one non-limiting embodiment.

When grasping and managing tissue, the end effector may comprise teeth to prevent slipping and milking. The shape and design of the teeth may be designed to minimize damage to the tissue. When the teeth are combined with an RF bi-polar device, for example, they need to work in concert with the electrical and compressive properties of the device to aid in both tissue sealing and tissue grasping. Thus, teeth are required that are not only atraumatic but also function properly with the RF sealing, or other type of energy-based sealing. FIG. 6 is a cross-sectional view of an end effector 210 having atraumatic teeth in a closed position in accordance with one non-limiting embodiment. Similar to the end effector 110 illustrated in FIGS. 3-5, the end effector 210 comprises a first jaw 220A and a second jaw 220b. The first and second jaws 220A and 220B may each define a channel 242A and 242B, respectively, for receiving a closure beam (not illustrated). A knife slot 272 may be defined to receive a cutting element (not illustrated) during an operation stroke. The inner channel 272 (FIG. 6) defines a transection plane 233 (FIG. 10) of the end effector 210, which is the plane through which the cutting element travels during an operational stroke. In FIG. 6, a cross-sectional end view of a transection plane 233 is schematically indicated by plane edge 281. As is to be appreciated, in some embodiments, the transection plane may be curved if the path of the cutting member in the end effector 210 is curved. At least one of the first jaw 220A and second jaw 220B may have teeth 243 positioned to assist with grasping, manipulating, energy delivery and/or compressing captured tissue. In some embodiments, at least one of the first jaw 220A and second jaw 220B carry a variable resistive positive temperature coefficient (PTC) body 275. When in the closed position, in one embodiment, at least a portion of PTC body 275 generally opposes an electrode 277. The electrode 277 may ride on an insulative body 279 to avoid contact between the electrode 277 and a return path to the RF source 145 (FIG. 1), such as the conductive portion of the second jaw 220B.

Figure 7:
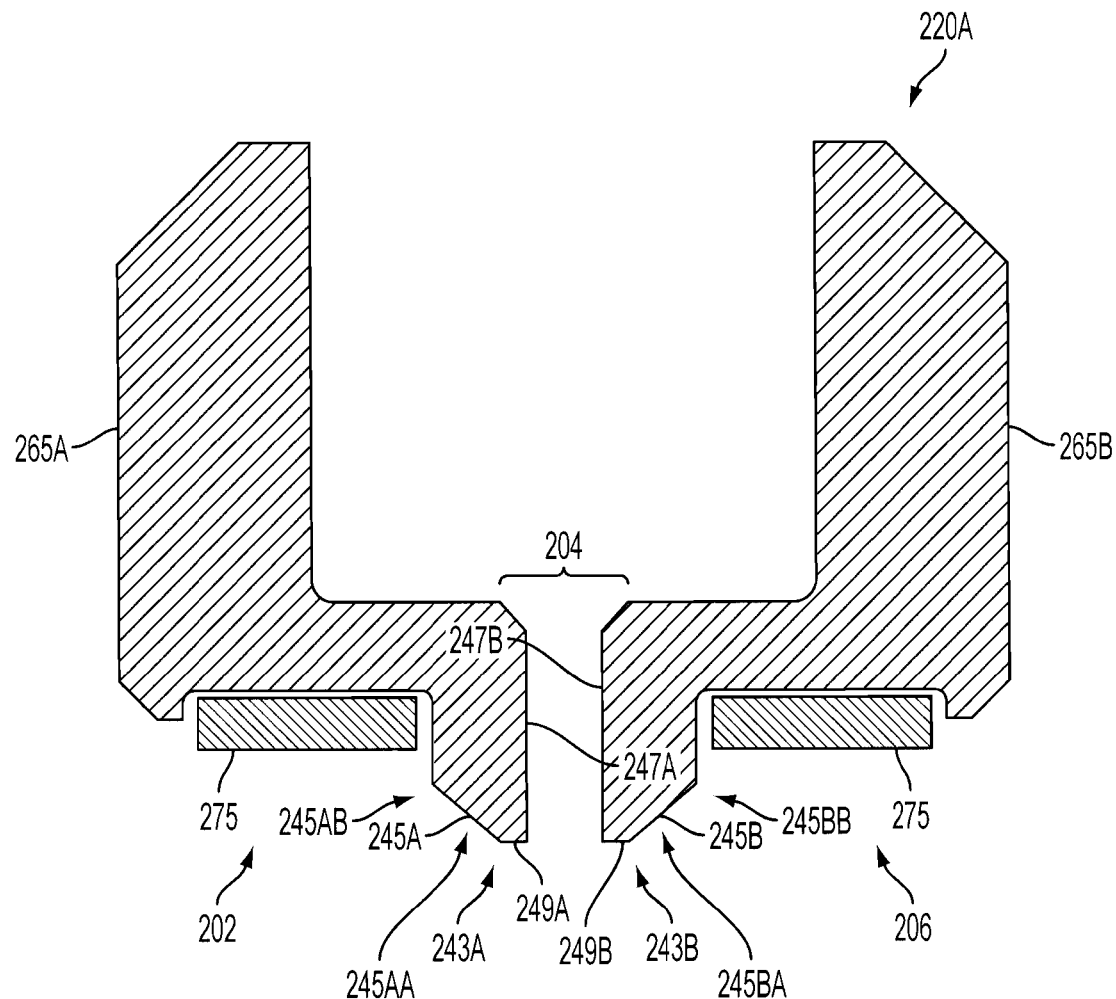
FIG. 7 is an enlarged cross-sectional view of the first jaw of the end effector shown in FIG. 6.

FIG. 7 is an enlarged cross-sectional view of the first jaw 220A of the end effector 210 shown in FIG. 6. The first jaw 220A may generally define a transection zone 204 that is disposed intermediate a first lateral portion 202 and a second lateral portion 206 and parallel to the transection plane of the end effector 210. The first lateral portion 202 may carry a first tooth 243A and the second lateral portion may carry a second tooth 243B. The teeth 243 may be integral or unitary with upper walls 265A and 265B of the first jaw 220A, as illustrated. In other embodiments, the teeth 243 may be joined to or otherwise coupled to the first jaw 220A using suitable attachment means. Laterally disposed teeth, such as tooth 243A and 243B may collectively have a generally "V-shaped" cross-sectional profile. For example, the first tooth 243A may have a slanted face 245A and the second tooth 243B may have a slanted face 245B. The slanted face 245A may comprise an inner portion 245AA and an outer portion 245AB. The slanted face 245A may be slanted such that the inner portion 245AA is positioned closer to the transection zone 204 than the outer portion 245AB. Similarly, the slanted face 245B may comprise an inner portion 245BA and an outer portion 245BB. The slanted face 245B may be slanted such that the inner portion 245BA is positioned closer to the transection zone 204 than the outer portion 245BB. The first tooth 243A may have a first transection zone face 247A and the second tooth 243B may have a second transection zone face 247B that is laterally opposed to the first transection zone face 247A. The first tooth 243A may comprise a lower face 249A that joins the slanted face 245A to the first transection zone face 247A and the second tooth 243B may comprise a lower face 249B that joins the slanted face 245B to the second transection zone face 247B to aid in the atraumatic engagement of captured tissue. While the slanted faces 245A and 245B are illustrated as being planar, it is to be appreciated that in some embodiments, the slanted faces 245A and/or 245B may be curved, or a combination of planar and curved components.

Figure 7A:
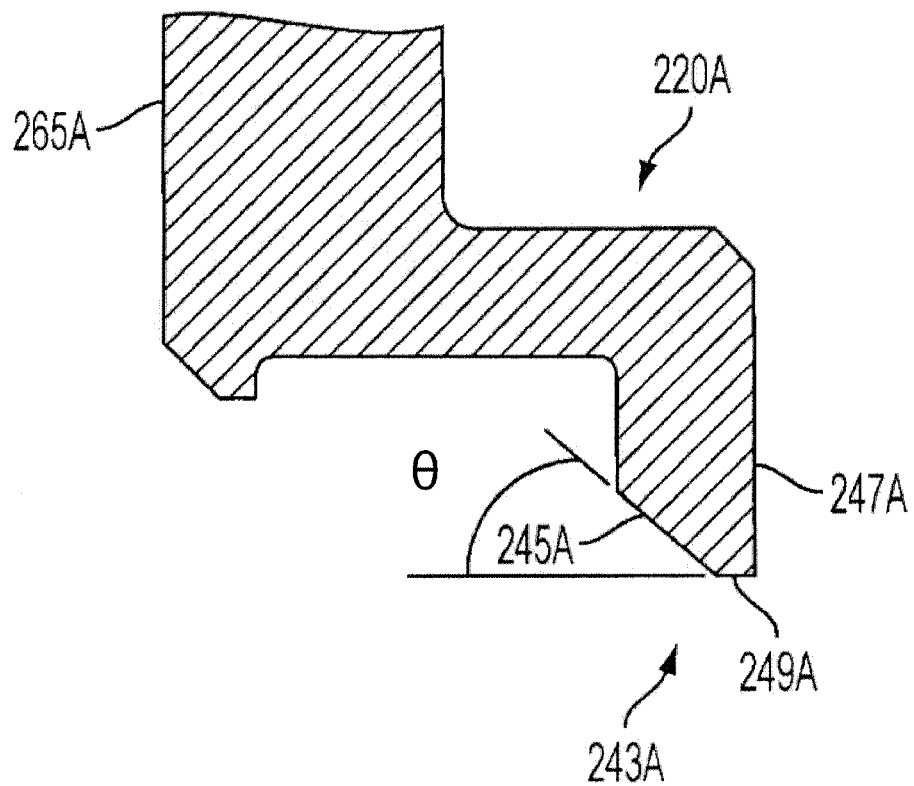
FIG. 7A is an enlarged view of tooth shown in FIG. 7 in accordance with one non-limiting embodiment.

FIG. 7A is an enlarged view of the first tooth 243A and a portion of the first jaw 220A in accordance with one non-limiting embodiment. As discussed, the first tooth 243A may comprise a lower face 249A that joins the slanted face 245A to the first transection zone face 247A to aid in the atraumatic engagement of captured tissue. The slanted face 245A has a slant angle of θ. In one embodiment, slant angle θ is approximately 42 degrees. The slant angle θ may differ based on application. In some embodiments, the slant angle θ of the tissue slanted faces may be based on the type of tissue being captured by the end effector 210 or may be based on the size of the end effector 210. In some embodiments, the slant angle θ may be in the range from about 10 degrees to about 80 degrees, for example.

Figure 8:
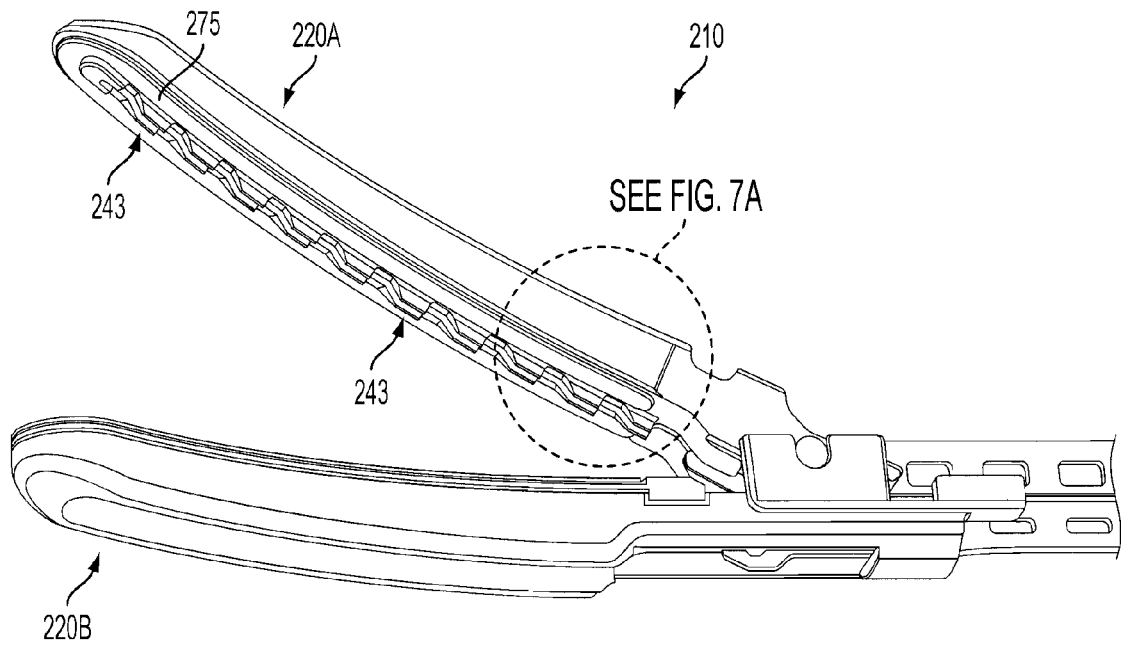
FIG. 8 is a perspective view of an end effector in accordance with one non-limiting embodiment.
Figure 8A:
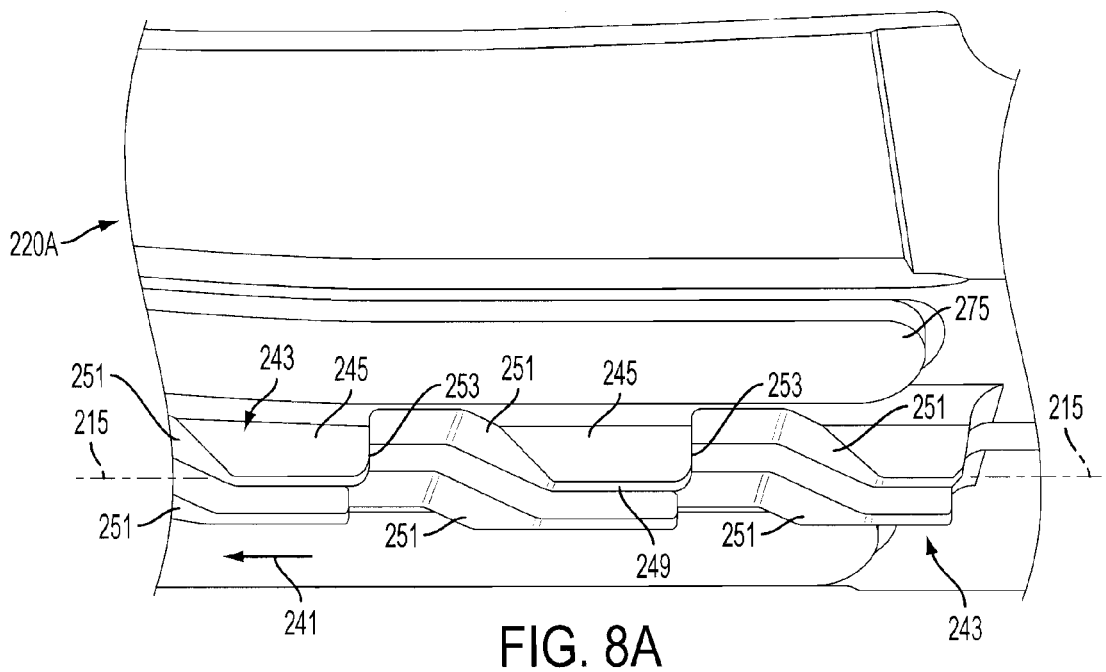
FIG. 8A is an enlarged view of a proximal portion of the first jaw shown in FIG. 8.

FIG. 8 is a perspective view of the end effector 210 and FIG. 8A is an enlarged view of a proximal portion of the first jaw of the end effector 210. As illustrated in FIGS. 8 and 8A, the end effector 210 may have a plurality of teeth 243 each with a slanted face 245 that serves as a tissue engaging surfaces. The teeth 243 may be elongated in the longitudinal direction with leading face 251 on the distal side and a trailing face 253 on the proximal side. The leading face 251 may be angled such that it is substantially oblique to a longitudinal axis 215 of the first jaw 220A. The trailing face 253 may be substantially normal to the longitudinal axis 215 of the first jaw 220A. In some embodiments, the trailing face 253 may also be slanted at either the same or different angle as the leading face 251. Generally, the angled leading face 251 allows tissue to move into the jaws 220A and 220B relatively easily while the square back (e.g., trailing face 253) assists in locking the tissue in place once the jaws are closed. The transitions from the leading face 251 to the lower face 249 and to the trailing face 253 may be rounded to reduce trauma to the captured tissue.

In some embodiments, the relatively long side profile of the teeth 243 provide tissue compression to maximize sealing when the RF (or other type of energy) energizes the tissue. For example, in one embodiment, the longitudinal length of an individual tooth 243 in the direction indicated by the arrow 241 may be about 3 to about 5 times the depth of the tooth 243, as determined by the length of the trailing face 253. In one embodiment, the longitudinal length of an individual tooth 243 in the direction indicated by the arrow 241 may be about 2 to about 7 times the depth of the tooth. In some embodiments, the longitudinal space between adjacent teeth may be about 2 to about 3 times smaller than the longitudinal length of the teeth 243 to increase the conductive and compressive nature of the teeth. In some embodiments, the longitudinal length of at least one tooth 243 may differ from the longitudinal length of a different tooth 243. Furthermore, while the teeth 243 are illustrated as being a component of the first jaw 220A, it is to be appreciated that the teeth 243 may instead be located on the second jaw 220B, or on both first and second jaws 220A and 220B. In some embodiments, the teeth 243 are conductive and are part of the return path for the RF source 145 (FIG. 1) with their relatively large surface area helping to compress and deliver energy to the captured tissue for sealing.

Figure 9:
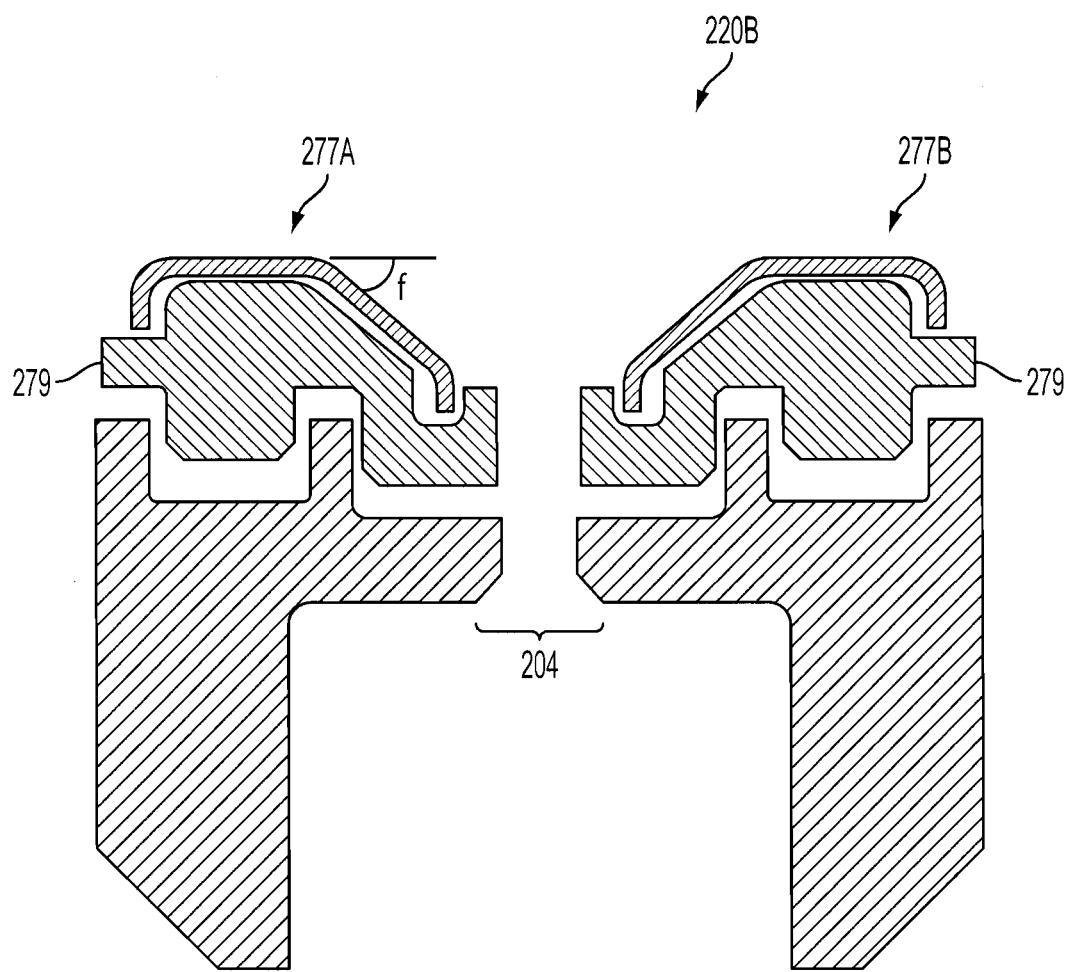
FIG. 9 is an enlarged cross-sectional view of the second jaw of the end effector shown in FIG. 6.

FIG. 9 is an enlarged cross-sectional view of the second jaw 220B of the end effector 210 shown in FIG. 6. The electrode 277 may have a first lateral portion 277A and a second lateral portion 277B that are separated by the transection zone 204. The first and second lateral portions 277A and 277B may collectively have a generally "V-shaped" cross-sectional profile. The particular profile of the electrode 277 may be coordinated with the profile of the teeth 243. For example, an electrode slant angle φ may be substantially similar to the slant angle θ of the slanted face 245A (FIG. 7A). Generally, a V-shaped electrode profile serves to increase the amount of contact with captured tissue thereby reducing the likelihood of charring the tissue, for example.

Figure 9A:
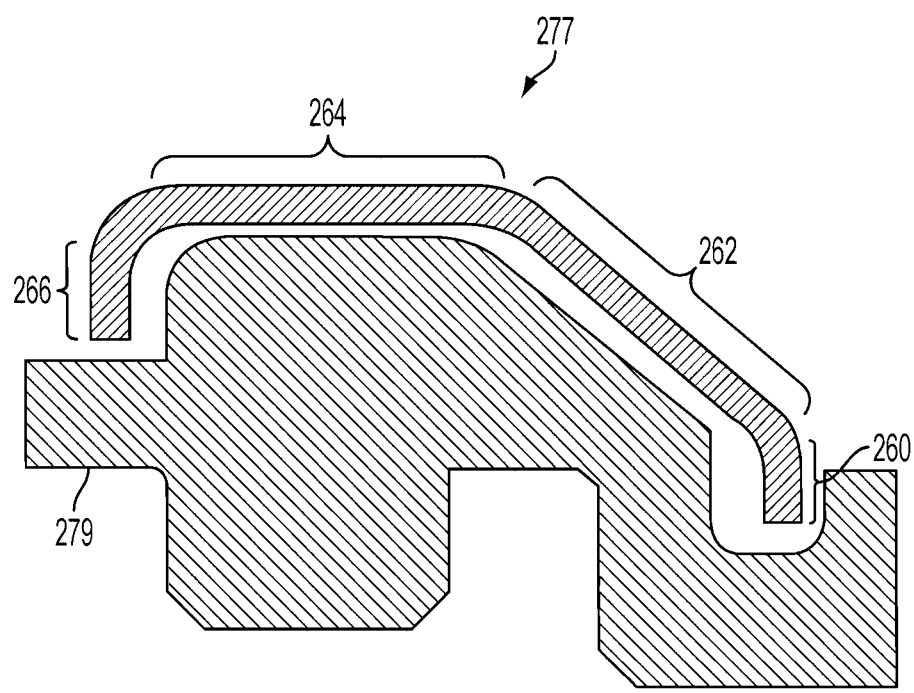
FIG. 9A is an enlarged view of a portion of FIG. 9.

FIG. 9A is an enlarged view of a portion of FIG. 9. The electrode 277 comprises a plurality of different sections, such as four sections, for example. Positioned proximate the transection plane is a inner vertical section 260 which transitions into a slanted section 262. Transitioning outwardly from the slanted section 262 yields a horizontal section 264 which then transitions into an outer vertical section 266. As illustrated, the transitions between the various sections of the electrode 277 may be rounded in order to reduce incidental damage to the captured tissue. As is to be appreciated, other embodiments may utilize an electrode 277 having a different cross-sectional profile. In any event, the teeth 243 (FIG. 7A) may have a cross-sectional profile that provides a beneficial interaction with the electrode 277. For example, in the closed position, the slanted face 245A of the first tooth 243A may be generally parallel to the slanted section 262 of the electrode.

Figure 6A:
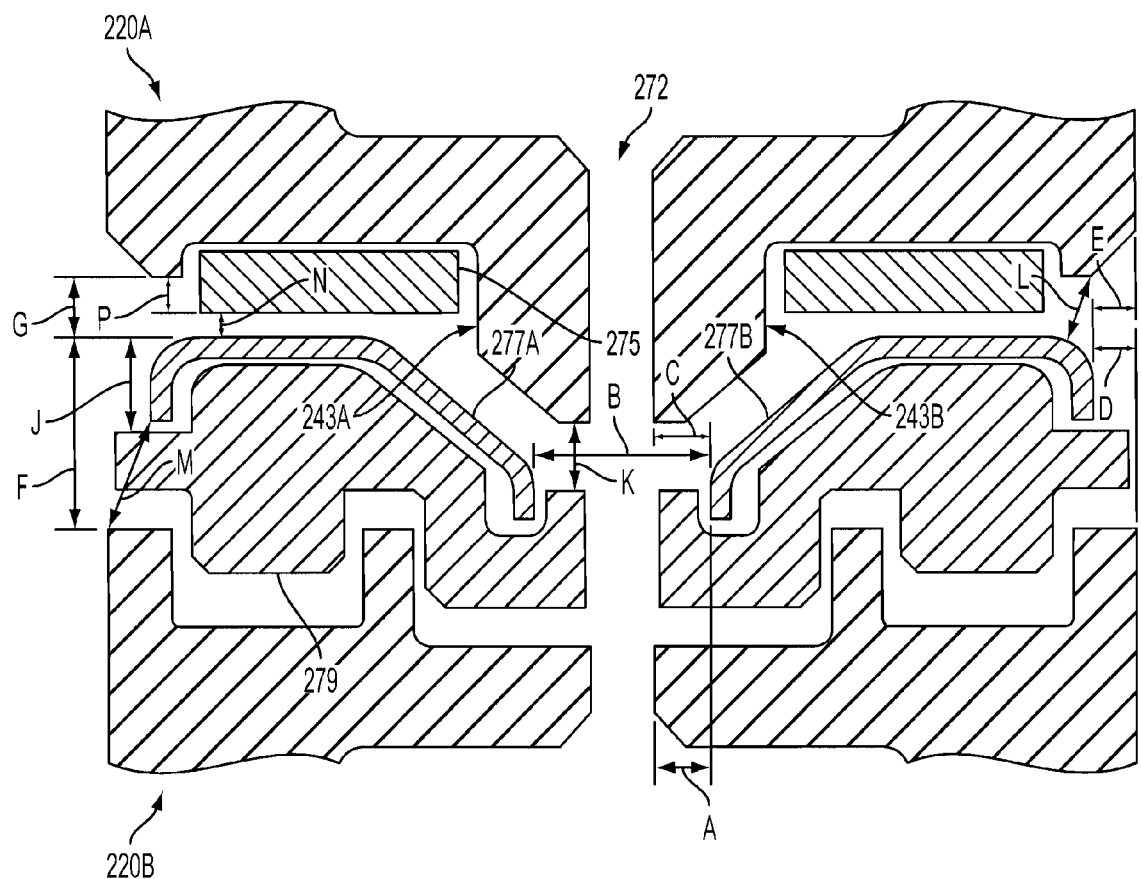
FIG. 6A is a cross-sectional view illustrating the interaction between the first jaw and the second jaw when the end effector is in the closed position in accordance with one non-limiting embodiment.

FIG. 6A is a cross-sectional view showing the interaction between the first and second jaws 220A, 220B in the closed position in accordance with one non-limiting embodiment. In the illustrated embodiment, the first jaw 220A comprises teeth 243A and 243B. As is to be appreciated, in some embodiments, the first jaw 220A may or may not comprise teeth and the second jaw 220B may or may not comprise teeth. Furthermore, first jaw 220A is illustrated carrying the variable resistive PTC body 275. As is to be appreciated, in some embodiments, the PTC body 275 may be wider, narrower, thinner or thicker than the illustrated embodiment. As used herein, the active electrode contact length is measured as the perimeter of the electrode 277 that is in contact with captured tissue when viewed from a cross sectional plane perpendicular to the transection plane. In some embodiments, the active electrode contact length may range from about 0.088" to about 0.269", for example. In some embodiments, the active electrode contact length may range from about 0.050" to about 0.400", for example. As used herein, the passive electrode contact length is measured as the portions of the first and second jaws 220A and 220B that are in contact with captured tissue when viewed from a cross sectional plane perpendicular to the transection plane. In some embodiments, the passive electrode contact length may range from about 0.113" to about 0.804", for example. In some embodiments, the passive electrode contact length may range from about 0.080" to about 1.000", for example. As used herein, the ratio of contact areas is the ratio between the active electrode contact length to the passive electrode contact length. In some embodiments, the ratio of contact areas ranges from about 0.145 to about 2.382, for example. In some embodiments, the ratio of contact areas ranges from about 0.080 to about 3.000, for example.

Still referring to FIG. 6A, The distance identified by distance "A" is the internal horizontal spacing between the knife slot 272 and the active electrode 277 on the second jaw 220B. In one embodiment, distance A is in the range of about 0.0" to about 0.044", for example. In another embodiment, distance A is in the range of about 0.0" to about 0.060", for example. The distance identified by distance "B" is the horizontal spacing between opposing active electrode 277 contact zones. In one embodiment, distance B is in the range of about 0.0" to about 0.034", for example. In another embodiment, distance B is in the range of about 0.0" to about 0.112", for example. The distance identified by distance "C" is the internal horizontal spacing between the knife slot 272 defined by the first jaw 220A and the active electrode 277 on the second jaw 220B. In one embodiment, distance C is in the range of about 0.0" to about 0.044", for example. In another embodiment, distance C is in the range of about 0.0" to about 0.060", for example. The distance identified by distance "D" is the external horizontal spacing between the active and passive electrode on the second jaw 220B. In one embodiment, distance D is in the range of about 0.0" to about 0.013", for example. In another embodiment, distance D is in the range of about 0.0" to about 0.025", for example. The distance identified by distance "E" is the external horizontal spacing between the active electrode on the second jaw 220B and the passive electrode on the first jaw 220A. In one embodiment, distance E is in the range of about 0.0" to about 0.012", for example. In another embodiment, distance E is in the range of about 0.0" to about 0.025", for example. The distance identified by distance "F" is the external vertical spacing between the active and passive electrode on the second jaw 220B. In one embodiment, distance F is in the range of about 0.0" to about 0.023", for example. In another embodiment, distance F is in the range of about 0.0" to about 0.035", for example. The distance identified by distance "G" is the external vertical spacing between the active electrode on the second jaw 220B and passive electrode on the first jaw 220A. In one embodiment, distance G is in the range of about 0.0" to about 0.028", for example. In another embodiment, distance G is in the range of about 0.0" to about 0.040", for example. The distance identified by distance "J" is the compression relief spacing on second jaw 220B. In one embodiment, distance J is about 0.002", for example. In another embodiment, distance J is about 0.005", for example. The distance identified by distance "K" is the vertical exposure of active electrode 277 to the knife slot 272. In one embodiment, distance K is in the range of about 0.006" to about 0.058", for example. In another embodiment, distance K is in the range of about 0.005" to about 0.060", for example. The distance identified by distance "L" is the straight line spacing between the upper edge/corner of the active electrode 277 to the lower edge/corner of the outer wall of the first jaw 220A. In one embodiment, distance L is in the range of about 0.008" to about 0.031", for example. In another embodiment, distance L is in the range of about 0.005" to about 0.040", for example. The distance identified by distance "M" is the straight line spacing between the lower edge/corner of the active electrode 277 to the upper edge/corner of the outer wall of the second jaw 200B. In one embodiment, distance M is in the range of about 0.005" to about 0.037", for example. In another embodiment, distance M is in the range of about 0.002" to about 0.045", for example. The distance identified by distance "N" is the straight line distance between the tissue contact surface of the second jaw 220B and the surface of the first jaw 220A. In one embodiment, distance N is in the range of about 0.0" to about 0.031", for example. In one embodiment, distance N is in the range of about 0.0" to about 0.045", for example. The distance identified by distance "P" is the compression relief spacing on first jaw 220A. In one embodiment, distance P is about 0.002", for example. In another embodiment, distance P is about 0.005", for example.

Generally, the V-shape cross-sectional profile of the electrode 277 provides numerous benefits, such as adding additional contact length to the active electrode surface, allowing closer proximity of the active electrode surface to the knife slot, allowing closer proximity between seal zones and better thermal communication between seal zones, and allowing inclusion of non traumatic teeth providing required compression and grasping capabilities.

Figure 10:
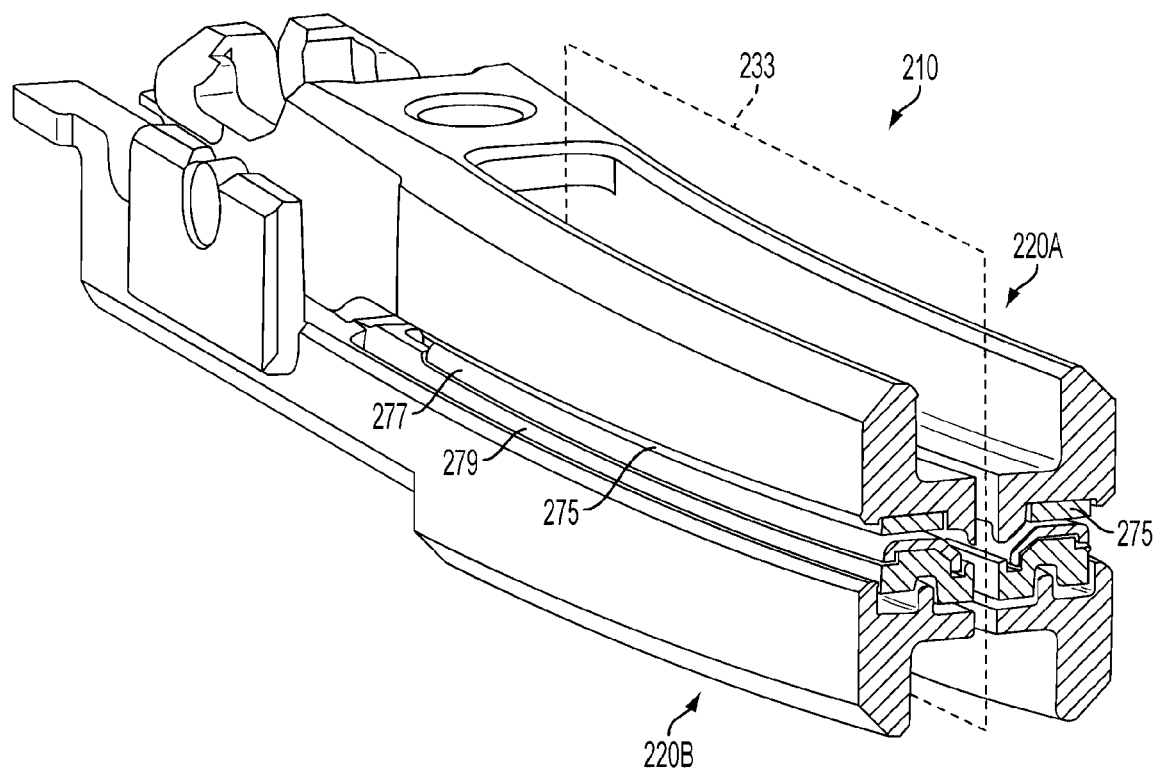
FIG. 10 is a cross-sectional perspective view of the end effector incorporating offset electrodes in accordance with one non-limiting embodiment.

FIG. 10 is a cross-sectional perspective view of the end effector 210 incorporating offset electrodes in accordance with one non-limiting embodiment. A transection plane 233 is illustrated that is generally parallel to the path that a cutting element (not illustrated) travels during an operational stroke. As illustrated, the transection plane 233 is curved to match the curve of the first jaw 220A and second jaw 220B. It is to be appreciated, that in embodiments having straight jaws, for example, the transection plane 233 will also be straight.

Figure 11:
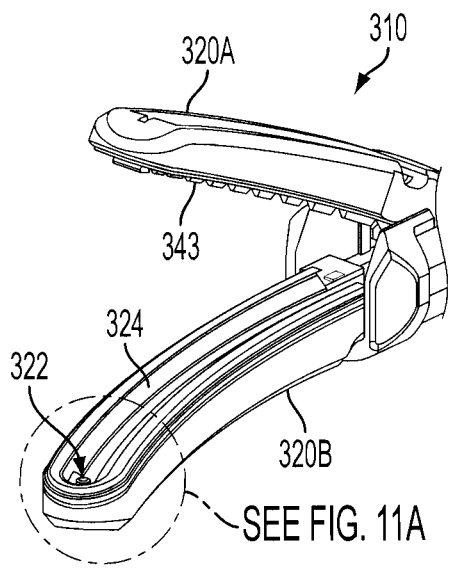
FIG. 11 illustrates an end effector in accordance with one non-limiting embodiment.
Figure 11A:
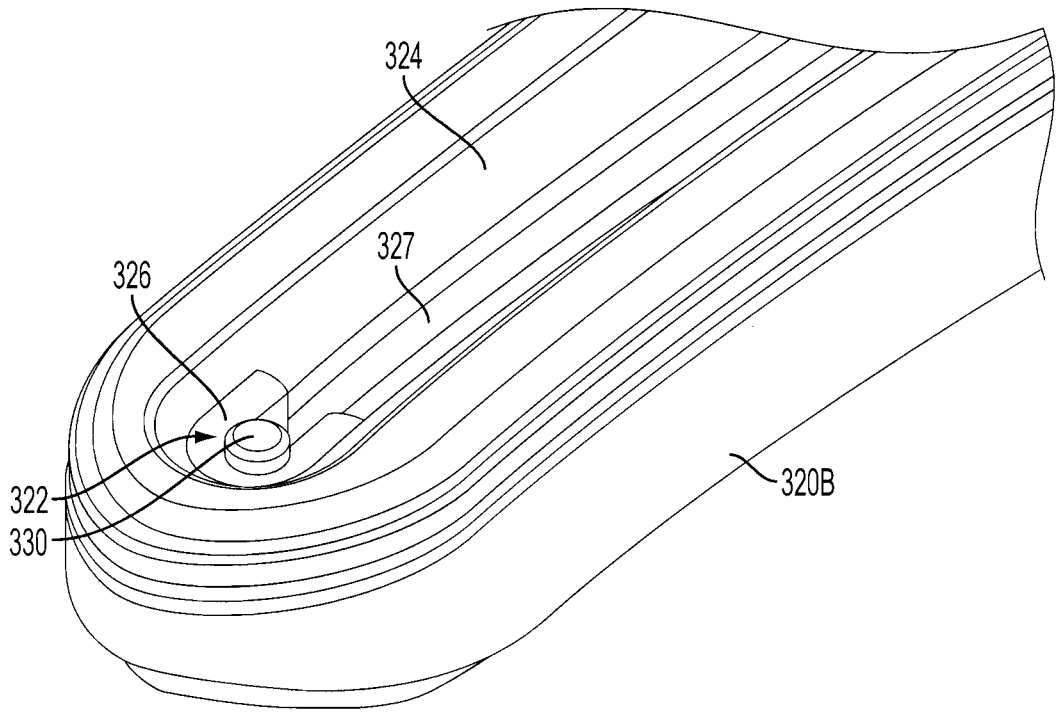
FIG. 11A is an enlarged view of a distal portion of the second jaw of the end effector shown in FIG. 11.
Figure 12:
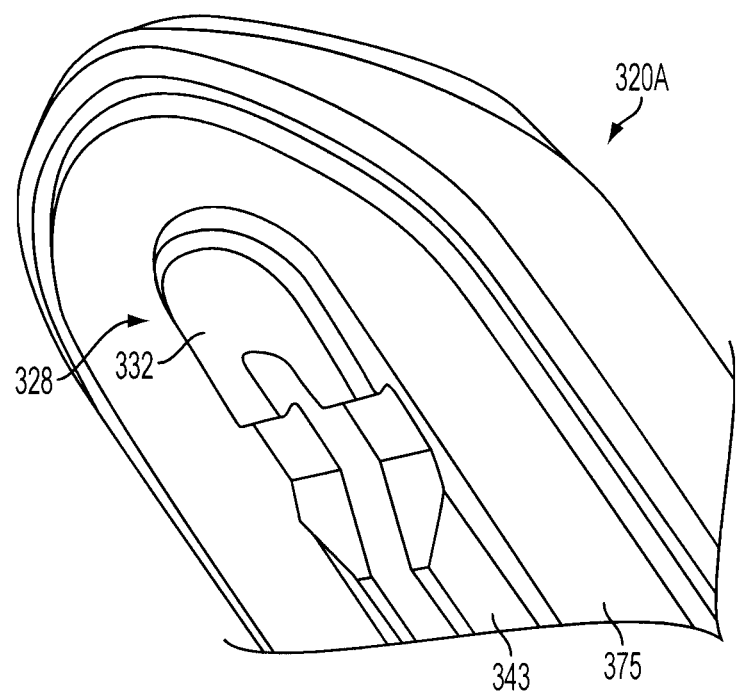
FIG. 12 is a partial perspective view of the first jaw of the end effector of FIG. 11 in accordance with one non-limiting embodiment.

FIG. 11 is an end effector 310 in accordance with one non-limiting embodiment. FIG. 11A is an enlarged view of a portion of FIG. 11. The end effector 310 may be structured similarly to the end effector 110 illustrated in FIG. 1 such that it has a first jaw 320A and a second jaw 320B. At least one of the jaws 320A and 320B may have teeth 343 for aiding in the manipulation and grasping of tissue. In some embodiments, the teeth 343 may be structured similarly to the teeth 243 illustrated in FIG. 7, for example. When using a bi-polar RF device having an end effector with sealing jaws, such as electrosurgical instrument 100 that is illustrated in FIG. 1, for example, it is important that the two separate conducting paths (e.g., energy supply path and energy return path) do not touch when tissue is not present in between the jaws of the end effector since a short circuit will result. As shown in FIG. 11A, the second jaw 320B may include a first conductive stop 322. The first conductive stop 322 is insulated from a supply electrode 324, which is in communication with the energy supply path, by an insulator 326. In one embodiment, the first conductive stop 322 may be positioned at the distal end of a knife slot 327. FIG. 12 is a partial perspective view of the first jaw 320A of the end effector 310 in accordance with one non-limiting embodiment. The first jaw 320A may include, for example, a variable resistive positive temperature coefficient (PTC) body 375, which is in electrical communication with the energy return path. The first jaw 320A may also include a second conductive stop 328. The first conductive stop 322 may have a surface 330 that can contact a surface 332 of the second conductive stop 328 when the end effector 310 in the closed position without any tissue intermediate the jaws. This interaction prevents the unwanted flow of energy (e.g., RF energy) when the electrosurgical instrument is not being used since the electrode 324 will be prevented from coming in contact with the PTC body 375, or any other part of the energy return path. Additionally, this interaction between the first and second conductive stops 322 and 328 prevents potentially damaging high force from being applied to the PTC body 375. As illustrated in FIGS. 11A and 12, the first and second conductive stops 322 and 328 may be made from the same material as other parts of the end effector 310, thereby easing manufacturing.

As illustrated in FIG. 11, the first conductive stop 322 may be positioned near the distal tip of the end effector 310. While the conductive stop 322 illustrated in FIG. 11 is cylindrical, it is to be appreciated that any suitable structure may be used. In one embodiment, the interaction between the first and second conductive stops 322 and 328 does not set the tissue gap for sealing but only prevents unwanted contact between a supply electrode and a return electrode of the end effector 310 when there is no tissue intermediate the jaws 320A and 320B. For example, an I-beam associated with the cutting element may set the tissue gap for sealing, while the conductive stop 322 is used to form a clearance between the supply electrode 324 and the PTC body 375 when no tissue is present between the jaws of the end effector. In any event, since the first and second conductive stops 322 and 328 may be conductive, they may serve as return paths when energy is delivered to tissue captured between the jaws 320A and 320B and therefore may aid in the sealing of the tissue.

Figure 13A:
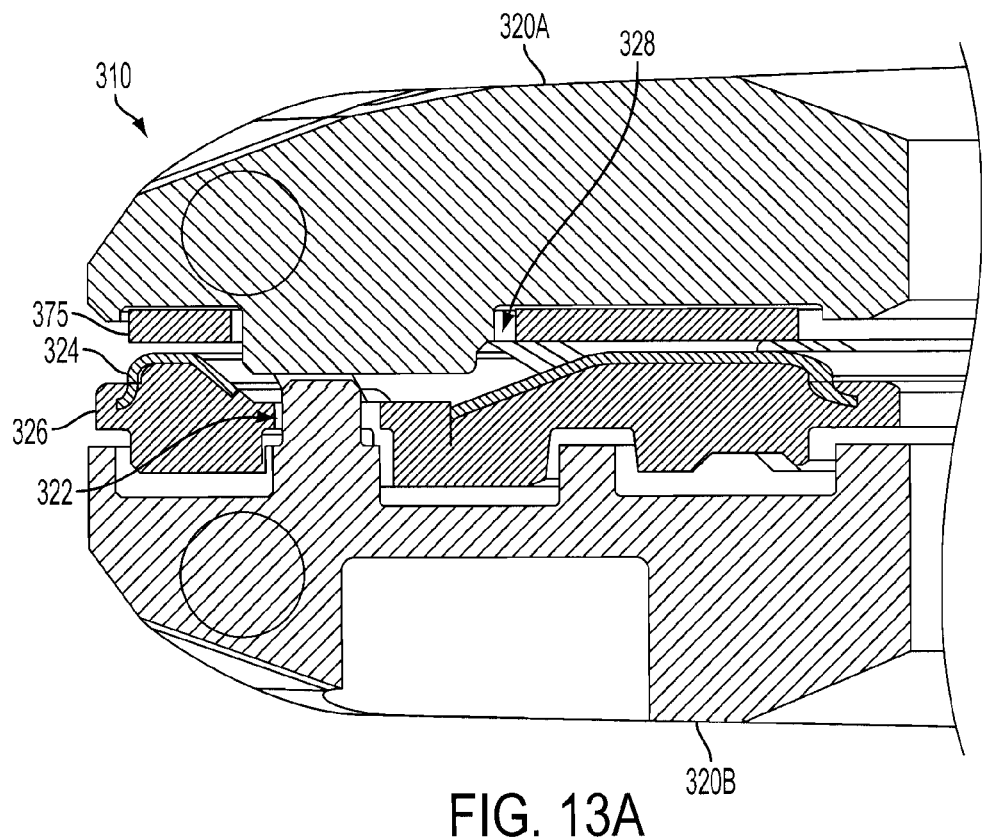
FIGS. 13A and 13B are cross-sectional side views of the distal end of the end effector illustrated in FIG. 11 during two states of operation.
Figure 13B:
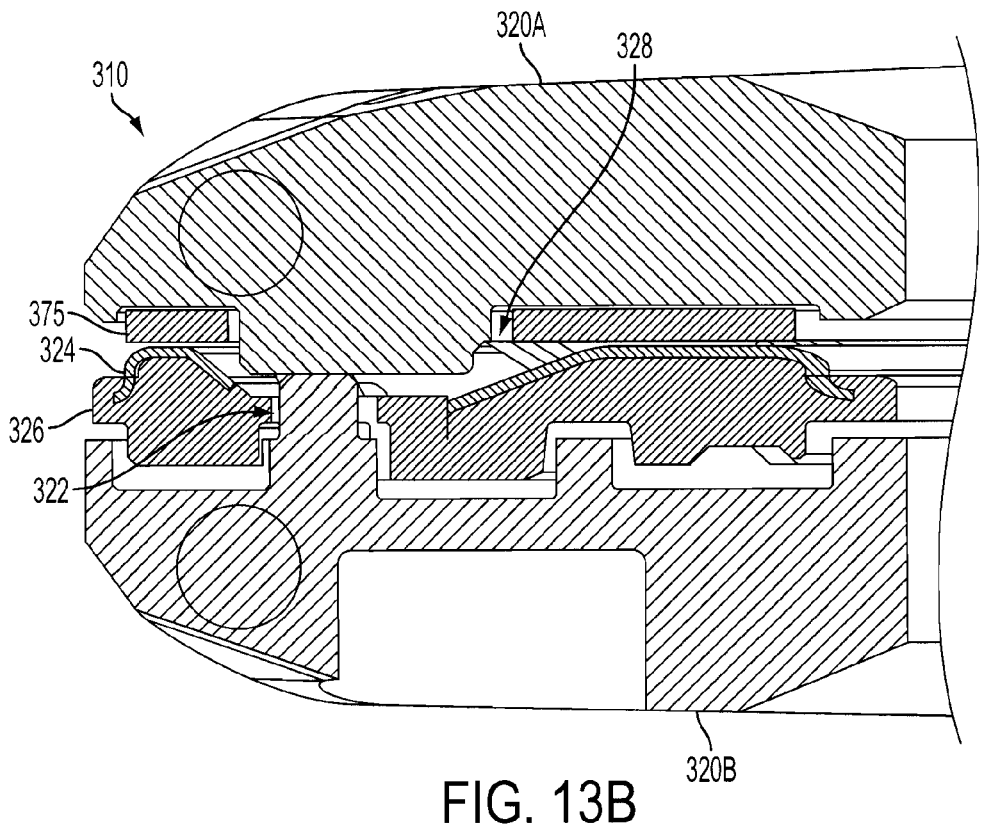

FIGS. 13A and 13B are cross-sectional side views of the distal end of the end effector 310 illustrated in FIG. 11 during two different states of operation. In FIG. 13A the placement of the first jaw 302A relative to the second jaw 302B is set by the I-beam (not illustrated) when it distally advanced through the end effector 310. In this state, in addition to separation between the electrode 324 and the PTC body 375, there is a separation between the first conductive stop 322 and the second conductive stop 328. In other words, during standard operation the first conductive stop 322 may not necessarily contact the second conductive stop 328. Comparatively, FIG. 13B illustrates the end effector in an "over-closed" state. An over-closed state may be caused by a variety of factors, such as loose fitting components, components out of tolerance, or gravity, for example. In this over-closed state, there is contact between the first conductive stop 322 and the second conductive stop 328. In this state, the electrode 324 is still prevented from making physical contact with the PTC body 375.

Figure 14:
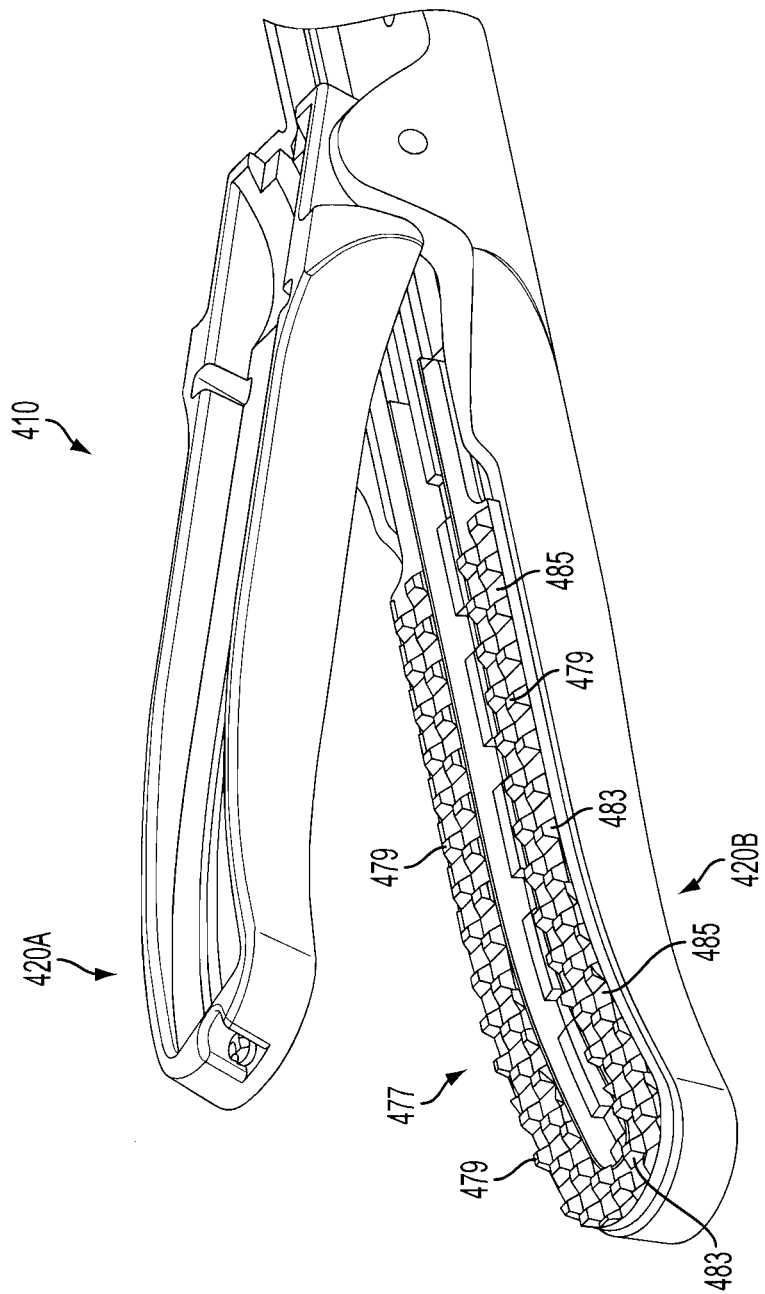
FIG. 14 illustrates an end effector that has an electrode that incorporates a waffle pattern in accordance with one non-limiting embodiment.
Figure 15:
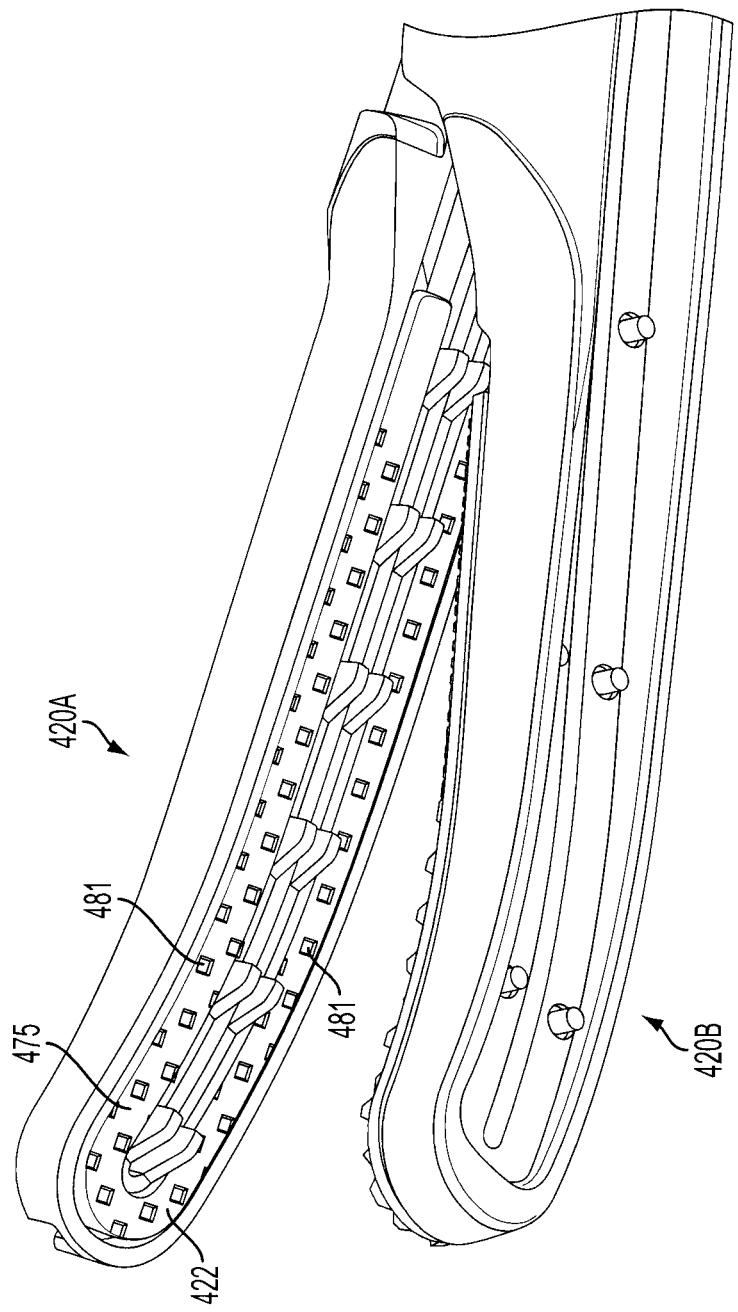
FIG. 15 illustrates the tissue contacting surface of the first jaw of the end effector shown in FIG. 14 in accordance with one non-limiting embodiment.

FIG. 14 is an end effector 410 that has an electrode 477 that incorporates a waffle pattern. As used herein, waffle pattern includes a grid-like pattern, as well as non-grid-like patterns. As illustrated the waffle pattern is incorporated onto the second jaw 420B. It is to be appreciated, however, that the waffle pattern may be incorporated into the first jaw 420A. Generally, the waffle pattern on the electrode 477 increases the surface area and the number of edges, thereby increasing the amount of tissue in contact with the electrode 477 when capturing tissue. The sharp edges also can help to concentrate electrical energy to improve transfer efficiency of the electrode 477. FIG. 15 shows the tissue contacting surface 422 of the first jaw 420A. As illustrated, a reverse pattern of the waffle pattern of the second jaw 420B may be incorporated into the first jaw 420A. The reverse waffle pattern may be created by the PTC body 475, for example. In some embodiments, the raised surfaces on the electrode may be use to form the corresponding indentations by heating the two elements and compressing to a desired depth.

The waffle pattern incorporated into the end effector 410 may be any suitable pattern, such as a grid of raised surfaces 479 (FIG. 14). In some embodiments, the waffle pattern may comprise randomly placed raised surfaces, or may comprise a combination of raised surface in a grid and raised surfaces in random locations. The waffle pattern may cover substantially the entire electrode 477, or less than substantially the entire electrode 477. The raised surface may be any suitable shape, such as square (as illustrated), oval, circular, or any other bounded shape. The corresponding indentions 481 may be a similar shape as the raised surface 479. In some embodiments, the raised surface 479 may incorporate a plurality of different shapes. The connecting surfaces 483 which span the raised surfaces 479 and base surface 485 may be outwardly slanted to increase the amount of surface area, as illustrated, or generally perpendicular to the base surface 485. The raised surfaces 479 may be generally evenly distributed across the electrode 477 or may have higher or lower concentrations in different portions of the electrode 477. In some embodiments, the end effector 410 may comprise more than 5 raised surfaces 479. In some embodiments, the end effector 410 may comprise more than 20 raised surfaces 479. In some embodiments, the end effector 410 may comprise more than 10 raised surfaces 479. In some embodiments, the end effector 410 may comprise more than 100 raised surfaces 479. The waffle-pattern may be generated through any suitable manufacturing technique, such as milling or stamping, for example. Additionally, in some embodiments, the raised surfaces may be incorporated into the PTC body 475 (or other return electrode) and the indentions may be incorporated into the active electrode 477. In some embodiments, the raised surfaces 479 may have a height of about 0.020" and the indentations may have a depth of about 0.020".

Figure 16:
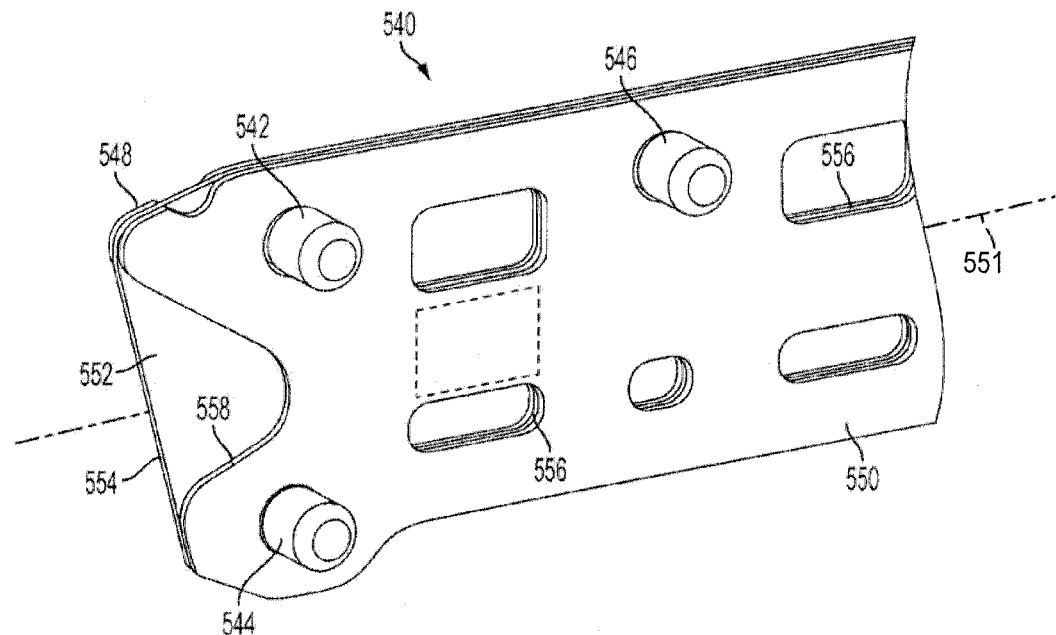
FIG. 16 illustrates the distal end of a movable cutting member in accordance with one non-limiting embodiment.

FIG. 16 is the distal end of a movable cutting member 540 in accordance with one non-limiting embodiment. The movable cutting member 540 may comprise a plurality of lateral extending elements, such as a first jaw closure pin 542 and a second jaw closure pin 544. Some embodiments of the movable cutting member 540 may have a jaw opening pin 546. As is to be appreciated, the pins may laterally extend from both sides of the movable cutting member 540. The movable cutting member 540 may be comprised of a plurality of bands, such as a first support band 548, a second support band 550, and a knife band 552 disposed intermediate the support bands 548 and 550. The knife band 552 may have a sharp distal cutting edge 554. The support bands 548 and 550 may provide rigidity to the movable cutting member 540 and protect the sharp distal cutting edge 554 from the walls of the knife slot 530 (FIG. 17), thereby preventing unintended wear on the distal cutting edge 554.

In some embodiments, the movable cutting member 540 may define at least one cutout 556 through at least one of the bands. The at least one cutout 556 may improve lateral flexibility of the movable cutting member 540. The first and second support bands 548 and 550 may also define a distal cutout 558, such as notch, for example. The cutout 558 may be generally symmetric about a longitudinal axis 551 or may be asymmetric (as illustrated). During transection, the distal cutout 558 provides a funneling action to the tissue to force it to the center of the cutting edge 554. Additionally, the movable cutting member 540 may be electrically coupled to the energy source to serve as part of the energy return path (e.g., the passive electrode).

Figure 17:
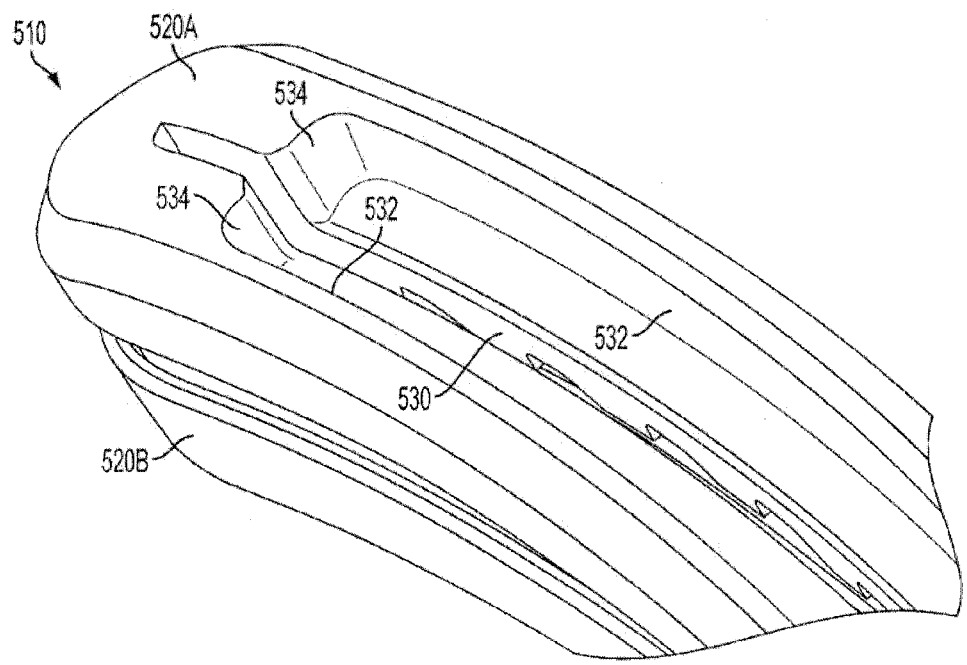
FIG. 17 is a view of a distal end of an end effector for use with the movable cutting member shown in FIG. 16.

FIG. 17 is a view of a distal end of an end effector 510 for use with the movable cutting member 540. The end effector has a first jaw 520A and a second jaw 520B. The first jaw 520A defines a knife slot 530 through which the movable cutting member 540 translates. The first jaw 520A may further define closure pin tracks 532 on either side of the knife slot 530. At the distal end of at least one of closure pin tracks 532 is a closure pin stop 534 to impede distal movement of the first jaw closure pin 542 during an operational stroke. As is to be appreciated, the second jaw 520B may include similar closure pin tracks and closure pin stop to accommodate second jaw closure pin 544. The knife slot 530 may distally extend further than the closure pin tracks 532, as the first and second jaw closure pins 542 and 544 are positioned slightly proximal from the sharp distal cutting edge 554. During a transection stroke, the first and second jaw closure pins 542 and 544 ride in the pin closure tracks to simultaneously close the end effector 510 and compress the tissue. The sharp distal cutting edge 554 transects the tissue as the movable cutting member 540 is distally progressed. The moveable cutting member 540 may be distally progressed until at least one of the jaw closure pins 542 and 544 engages a pin stop, such as pin stop 534. In some embodiment, the use of the pin stop 534 may provide repeatable cutting length and prevent damage to the sharp distal cutting edge 554 by preventing the sharp distal cutting edge 554 from contacting the distal end of the knife slot 530.

When closing a jaw of an end effector on tissue, using an I-beam, for example, there is a high starting load. This high starting load is due, in part, to the tissue being far away from the end effector's pivot and the I-beam, or other closing member, closing the jaw while close to the end effector's pivot. Tissue generally acts as a spring when it is compressed. The more it is compressed the higher the force necessary to compress it. Once the fluids have been forced out of the tissue, tissue becomes even more difficult to compress. Generally, the higher the compressive loads the greater the force to fire the I-beam. Even relatively small changes in jaw closure height, as little as 0.001 inches, for example, can greatly change the compressive loads from the tissue to the I-beam. Additionally, for embodiments having a single trigger with a relatively small throw (e.g., less than about 40 mm), the trigger has to perform a lot of work with a relatively small stroke (e.g., the path 129 in FIG. 2). As discussed in more detail below, systems and methods are presented herein to reduce the force necessary to perform the operational stroke (e.g., "force to fire").

Figure 18:
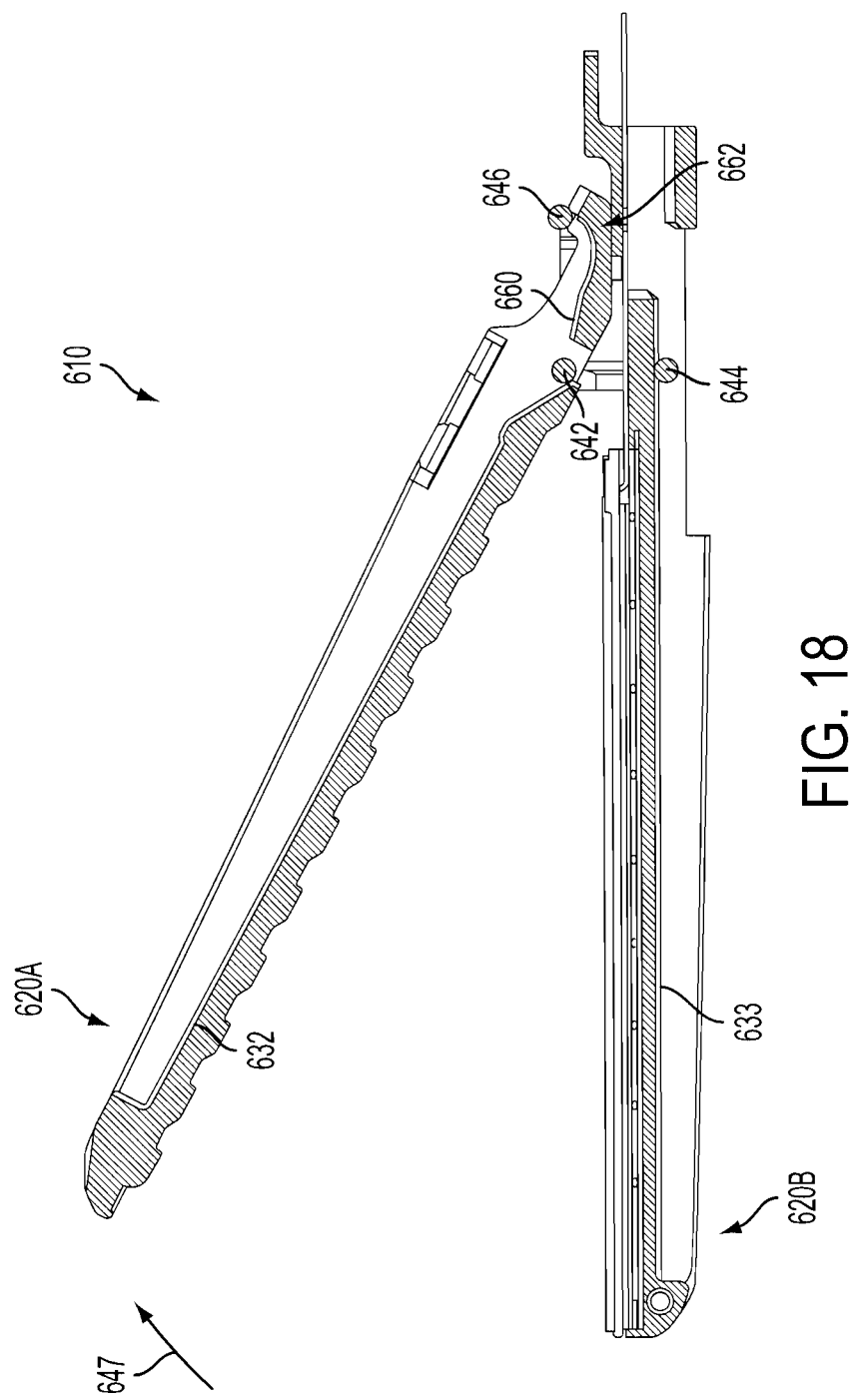
FIG. 18 is a cross-sectional view of an end effector in an opened position in accordance with one non-limiting embodiment.

In one embodiment, the amount of force necessary to distally advance the cutting member after the tissue has been clamped may be reduced by altering the shape of a path (e.g., the ramp) that the closing member, such as an I-beam, travels during an operational stroke. In various embodiments, the shape of the ramp profile may be cammed to generally reduce the amount of tissue compression. FIG. 18 shows a cross-sectional view of an end effector 610 in an opened position in accordance with one non-limiting embodiment. Similar to previously discussed embodiments, the end effector 610 may have a first jaw 620A that is pivotable towards a second jaw 620B during an operational stroke. A variety of pins that are coupled to a movable cutting member (not illustrated) may engage with various ramps within the end effector 610 open and/or close the jaws 620A and 620B.

In one embodiment, to open the jaws 620A and 620B of the end effector 610, a proximal pin 646 may engage an opening ramp 660 when the proximal pin 646 is drawn proximally (e.g., at the conclusion of an operational stroke). The opening ramp 660 may have a curved tail section 662 that the causes the first jaw 620A to rapidly pivot in the direction indicated by the arrow 647 when engaged with the proximal pin 646. As is to be appreciated, the cross-sectional shape of the opening ramp 660 will affect the relative speed at which the jaws 620A and 620B open. For example, an end effector having an opening ramp that has a relatively gradual slope will open more slowly than an end effector with a steeper opening ramp. As illustrated, the jaws 620A and 620B may "open" when the second jaw 620B remains relatively stationary while the distal end of the first jaw 620A pivots away from the distal end of the second jaw 620A. In some embodiments, however, the second jaw 620B may also comprise an opening ramp similar to the opening ramp 660 of the first jaw 620A. In yet other embodiments, only the second jaw 620B comprises an opening ramp that is configured to pivot the distal end of the second jaw 620B away from the distal end of the first jaw 620A.

Figure 19:
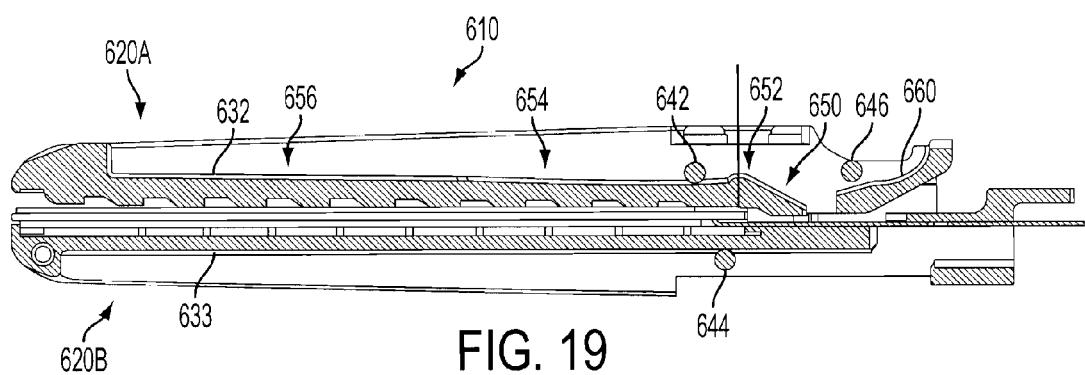
FIGS. 19 and 20 illustrate the end effector shown in FIG. 18 after the first jaw has been pivoted toward the second jaw.
Figure 20:
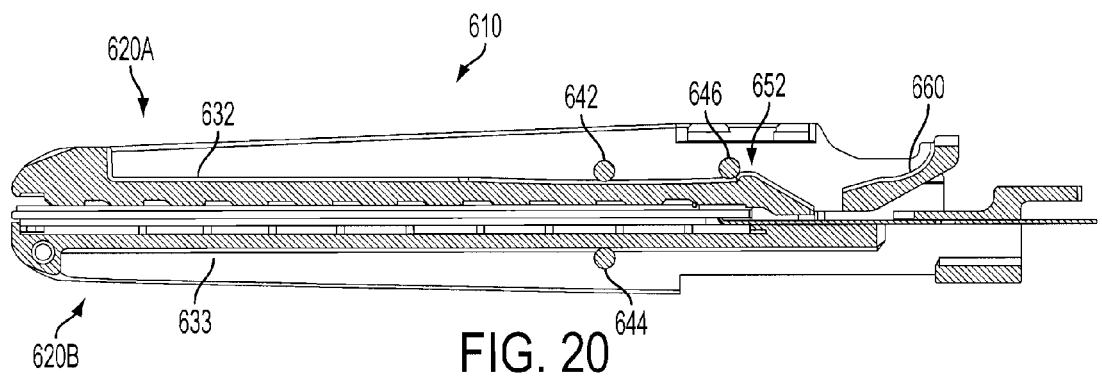

The end effector 610 may comprise additional cammed compression pathways to accommodate a first jaw closure pin 642 and a second jaw closure pin 644 during an operational stroke. In one embodiment, the first jaw 620A has a first closure pin track 632 and the second jaw 620B has a second closure pin track 633. The second closure pin track 633 can be substantially linear, as illustrated, or may include a variety of sloped or curved portions. In the illustrated embodiment, the first closure pin track 632 has a plurality of sloped profiles to affect the action of the first jaw 620A during an operational stroke and reduce the force to fire. FIG. 19 illustrates the end effector after the first jaw 620A has been pivoted toward the second jaw 620B through distal advancement of the movable cutting member. At the proximal end of the first closure pin track 632 is a relatively steep closure ramp 650. As the first jaw closure pin 642 is distally translated from the position shown in FIG. 18, it engages the closure ramp 650 to pivot the first jaw 620A toward the second jaw 620B relatively quickly. The first jaw closure pin 642 then encounters a ridge 652 at the top of the closure ramp 650. The ridge 652 may have a flat portion that transitions down to a ramped section 654. In some embodiments, the tissue contacting surface of the first jaw 620A may be angled to reduce the compressive impact on the tissue at the distal end of the end effector 610 prior to advancement of the moveable cutting member. FIG. 20 illustrates the first jaw closure pin 642 engaged to the ramped section 654. The ramped section 654 transitions to a flat section 656 positioned intermediate the ramped section 654 and the distal end of the end effector 610. The relative elevation of the flat section 656 may be substantially similar to that of the flat portion of the ridge 652. In various embodiments, the proximal pin 646 may be positioned on the movable cutting member such that it does not contact the first closure pin track 632. The second jaw closure pin 644 may progress along the second closure pin track 633 during the operational stroke.

Figure 21:
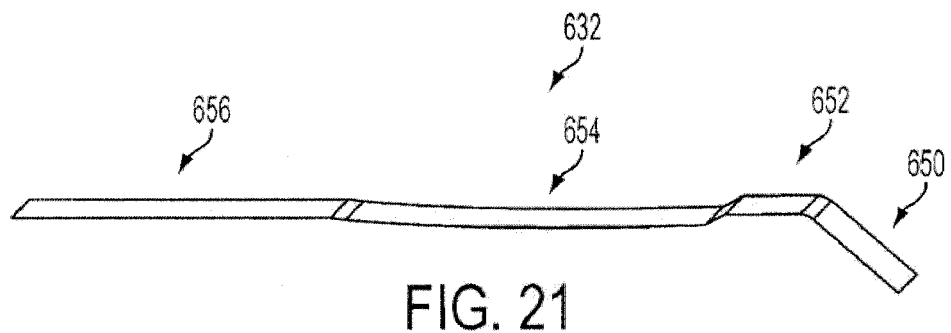
FIG. 21 is a profile of a first closure pin track in accordance with one non-limiting embodiment.

For clarity, the profile of the first closure pin track 632 in accordance with one non-limiting embodiment is illustrated in FIG. 21. The closure ramp 650 leads to a ridge 652 that has a full close flat portion. The flat portion of the ridge 652 leads to a downward ramped section 654. The downward ramped section 654 generally relieves the closing pressure where the loads are highest. The ramped section 654 ramps back up to a full close flat section 656 for final compression. By having a multi-sloped track, the mechanical advantage of the handle can be better utilized and the force to fire may be reduced while the handle puts forth low mechanical advantage. The force to return the moveable cutting member is also reduced due to less compression as it returns. As is to be appreciated, the profile of the track may be modified in various embodiments. For example, the length of slope of the ramped section 654 may be modified, or the flat section 656 may be modified to have a slope, or other modifications may be made. Furthermore, the second closure pin track 633 may be modified to have features similar to that of first closure pin track 632.

In some embodiments, various finishings, coatings, and/or lubrications may be used to reduce trigger forces by lowering friction between the moving components of the end effector. In some embodiments, at least one of the first jaw closure pin 642 and a second jaw closure pin 644 are coated with a friction reducing substance. The tracks in which the pins travel may also be coated with a friction reducing substance. In some embodiments, the friction reducing substances may include boron aluminum manganese (BAM), aluminum titanium nitride (AlTiN), titanium nitride, diamond-like carbon (DLC), molybdenum disulfide titanium, or vanadium carbide (VC), for example. The sides of the moveable cutting member may also be coated with a friction reducing substance, such as titanium nitride (TiN), for example, to help reduce galling against the jaw track. Additionally, any suitable lubrication substance may be used to reduce the force to fire and improve operation of the surgical instrument. A non-exhaustive and non-limiting list of suitable lubricants include KRYTOX, sodium stearate, DOW 360, and NUSIL, for example. The surface finish of various components of the end effector 610 may also be modified to lower friction. For example, the interfaces between various components of the end effector may be electropolished and secondary mechanical polishing using abrasives may be utilized. In some embodiments, an average surface roughness of about 4 to 16 microinches is targeted.

In some embodiments, various components may be made from specific materials that help to reduce frictional forces. As described above, lowering the friction of interface components can reduce the force to fire of the end effector. In one embodiment, spinodal bronzes may be utilized to assist in the reduction of friction. Generally, spinodal bronzes contain copper and nickel and operate well in applications having high loads and low speeds. A variety of parts of the end effector 610 may be comprised of spinodal bronze, such as the pins 642, 644, and 646, for example. Spinodal bronzes are available from ANCHOR BRONZE (e.g., NICOMET) and BRUSH-WELLMAN (e.g., TOUGHMET). Parts comprised of spinodal bronze may be used in a wide variety of surgical instruments, such as endocutters, staplers, RF devices, and ultrasonice devices, for example.

Figure 22:
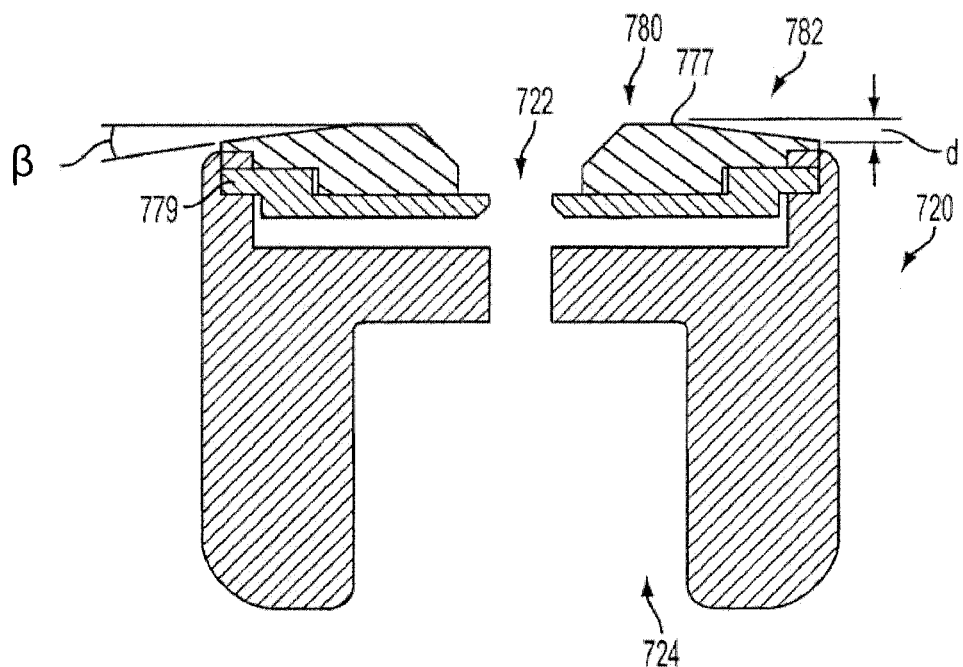
FIG. 22 is a cross-sectional view of a jaw in accordance with one non-limiting embodiment.

In some embodiments, other techniques are used to reduce the force at the trigger and enable a greater chance of success of seal. For example, the amount of force required to compress the tissue may be reduced by reducing the amount of tissue being compressed to a relatively small thickness, such as 0.006", for example. FIG. 22 is a cross-sectional view of a jaw 720 in accordance with one non-limiting embodiment. Similar to previously described jaw, the jaw 720 may define a cavity 724 to receive a compression element, such as an I-beam, for example, and a knife cavity 722 through which a cutting element can pass. The jaw 720 also has a tapered electrode 777 positioned on an insulator 779. The tapered electrode 777 has an inner region 780 that is positioned toward an inner edge of the tapered electrode 777. In one embodiment, at full compression there is about a 0.006" gap between the inner region 780 and a passive electrode positioned on an opposing jaw (not shown). This narrow region is the area intended to have the greatest seal strength. Moving outward, the tapered electrode 777 tapers away from the inner region 780 and increases the gap. As the gap increases, the amount of tissue compression is decreased. The taper angle β may be any suitable angle, such as in the range from about 1 to about 30 degrees, for example. In one embodiment, the taper angle β is about 10 degrees. In one embodiment, an outer region 782 descends a distance d from the inner region 780. In one embodiment, the distance d is about 0.007". In some embodiments, the distance d may be in the range of about 0.002" to about 0.020", for example. Through the use of tapered surface, the tissue load in the jaw may decrease in the range of about 30% to about 50%. In some embodiments, the passive electrode may be alternatively tapered, or both the active electrode and the passive electrode may be tapered. Generally, tapering the electrode effectively reduces the amount of tissue that is to be compressed by the jaws, with tissue proximate the cutting element receiving the most compression. In some embodiments, other electrode configuration may be implemented to achieve a variation in tissue compression across the contacting surface of the electrode. In one embodiment, for example, the electrode is cylindrically shaped to compress the tissue at a narrow line contact along the jaw length. All such implementations are intended to be covered by this disclosure.

Figure 23A:
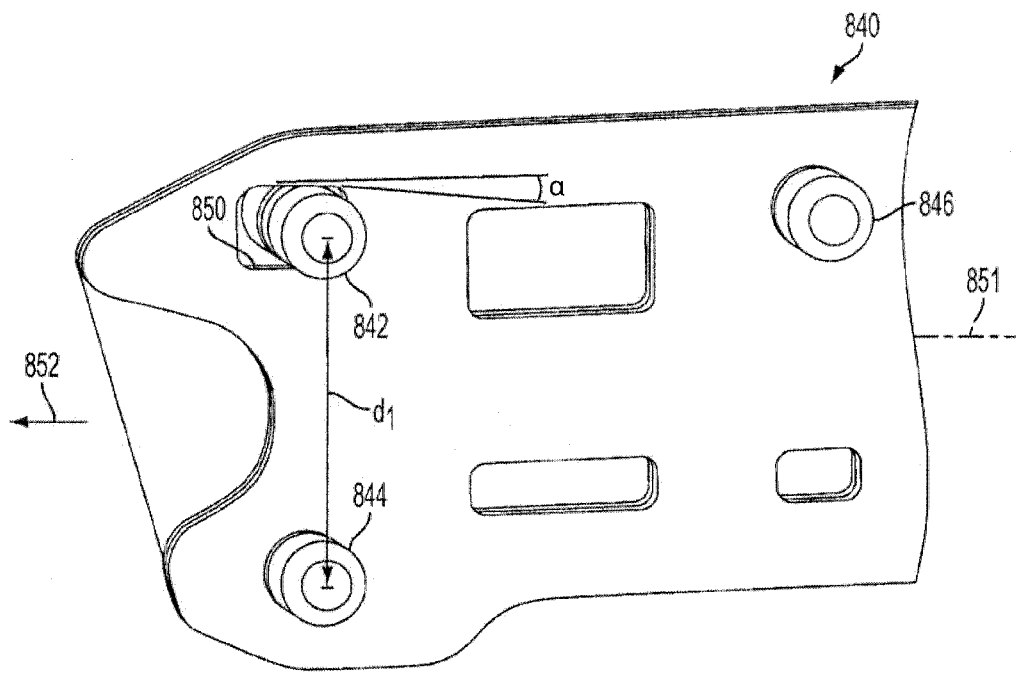
FIGS. 23A and 23B illustrates a closure pin affixed to a moveable cutting member during two states of operation in accordance with one non-limiting embodiment.
Figure 23B:
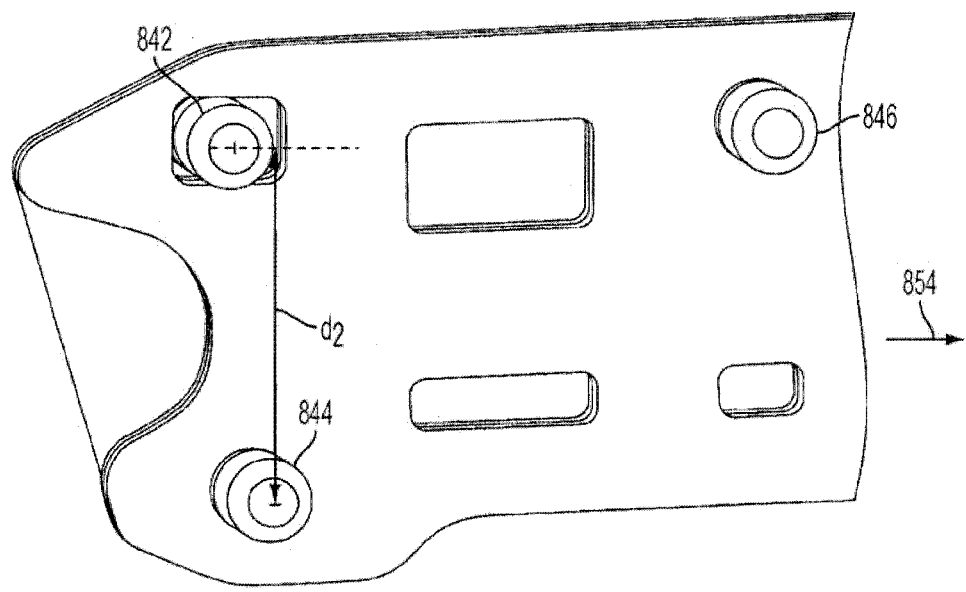

In some embodiments, the relative distance between the compression pins on the movable cutting member may differ during different stages of the operational stroke. For example, the pins may be relatively closer during the compression/cutting portion of the stroke and relatively further away when the moveable cutting member is being retracted from the distal end of the end effector and translated toward the proximal end of the end effector. A movable cutting member 840 with movable pins is illustrated in FIGS. 23A and 23B. While the movable cutting member 840 is illustrated as a banded cutting member similar to the cutting member 540 illustrated in FIG. 16, it is to be appreciated that any suitable movable cutting member may be used. The movable cutting member 840 comprises a first jaw closure pin 842, a second jaw closure pin 844 and a proximal pin 846. At least one of the first and second jaw closure pins 842 and 844 may ride in a slot or cam surface to allow the pins 842 and 844 to move relative to one another. As illustrated, the first jaw closure pin 842 may be positioned in a slot 850. The slot 850 may be oblique to a longitudinal axis 851 of the movable cutting member 840. In one embodiment the slot angle α is about 5 degrees. In some embodiments, the slot angle α may be in the range of about 2 degrees to about 30 degrees, for example. The particular position of the first jaw closure pin 842 within the slot 850 will depend on the action of movable cutting member 840. In FIG. 23A, for example, the first jaw closure pin 842 is shown in the position corresponding to when the movable cutting member 840 is being translated in the direction indicated by arrow 852 (e.g., during cutting). In this position, the first jaw closure pin 842 is driven downward and the vertical separation between the first jaw closure pin 842 and the second jaw closure pin 844 is distance $d_1$. Comparatively, in FIG. 23B the first jaw closure pin 842 is shown in the position corresponding to when the movable cutting member 840 is translated in the direction indicated by arrow 854 (e.g., during retraction). In this position, the first jaw closure pin 842 is driven upward and the vertical separation from the first jaw closure pin 842 and the second jaw closure pin 844 is increased to a distance $d_2$, where $d_2 > d_1$. As is to be appreciated the difference between $d_2$ and $d_1$ is at least partially based on the slot angle α. In other words, the greater the slot angle α, the greater the difference between $d_2$ and $d_1$. The additional distance of separation between the jaw closure pins 842 and 844 in the reverse direction will increase the compression gap which will lower the force required to retract the compression system.

Figure 24:
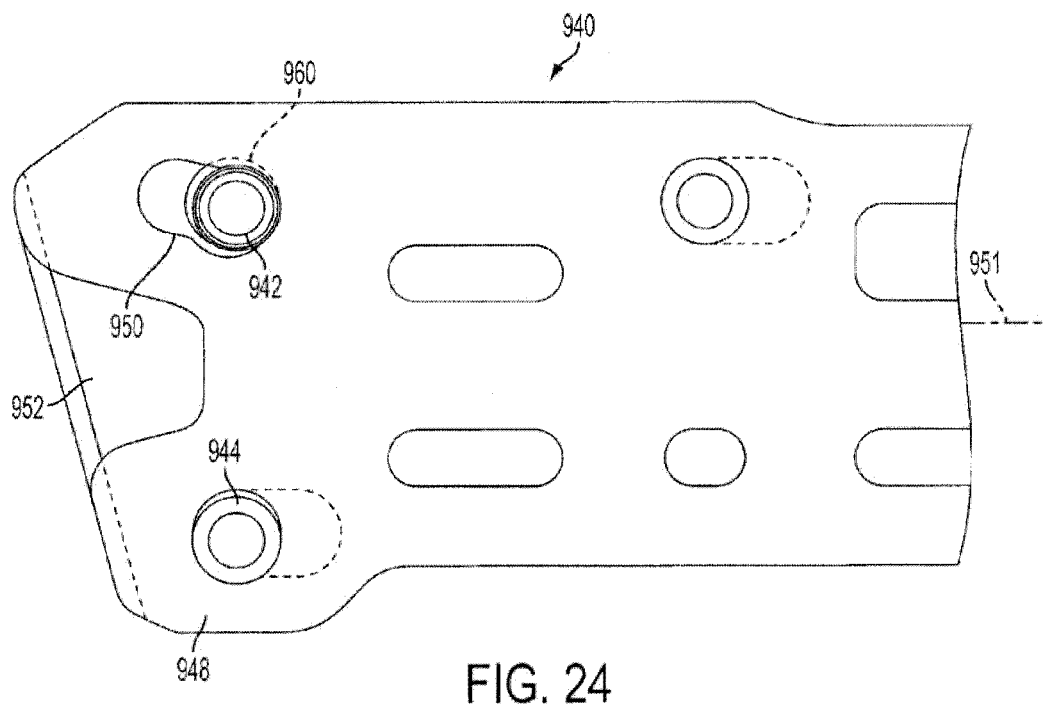
FIG. 24 illustrates a moveable cutting member with translating bands in accordance with one non-limiting embodiment.
Figure 25:
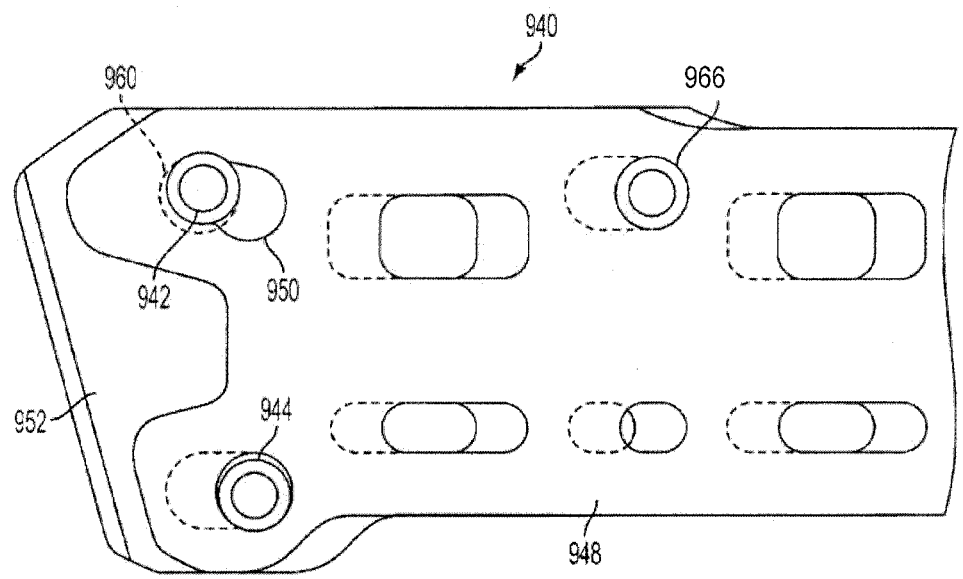
FIG. 25 illustrates the movable cutting member of FIG. 24 during retraction/return.

In some embodiments, additional features (slots, notches, or cutouts, for example) in the bands of the moveable cutting member may be used to ensure the closure pin moves back (down) and forward (up) appropriately during an operational stroke. The multiple bands may be timed to push the slotted pin either up or down based on the forward or reverse motion of the moveable cutting member. A moveable cutting member 940 with translating bands in accordance with one non-limiting embodiment is shown in FIG. 24. A central band 952 has a vertical slot 960. Two outer bands 948 each have an angled slot 950. The angled slot 950 is oblique to a longitudinal axis 951 of the movable cutting member 940. A first jaw closure pin 942 rests between the three bands. During a cutting stroke, the outer bands 948 are pushed distally relative to the central band 952 and the first jaw closure pin 942 is forced toward the proximal end of the angled slot 950 and the bottom of the vertical slot 960. In this position, the first jaw closure pin 942 and the second jaw closure pin 944 are exerting a relatively high amount of compression force on the captured tissue. FIG. 25 illustrates the movable cutting member 940 during a retraction/return. When the outer bands 948 are pulled proximally in relation to the central band 952, the first jaw closure pin 942 is forced toward the distal end of the angled slot 950 and the top of the vertical slot 960, thereby increasing the vertical separation between the first jaw closure pin 942 and the second jaw closure pin 944. In this position, the distance separating pins 942 and 944 decreases the amount of tissue compression and reduces the force required to retract the moveable cutting member 940.

Figure 26:
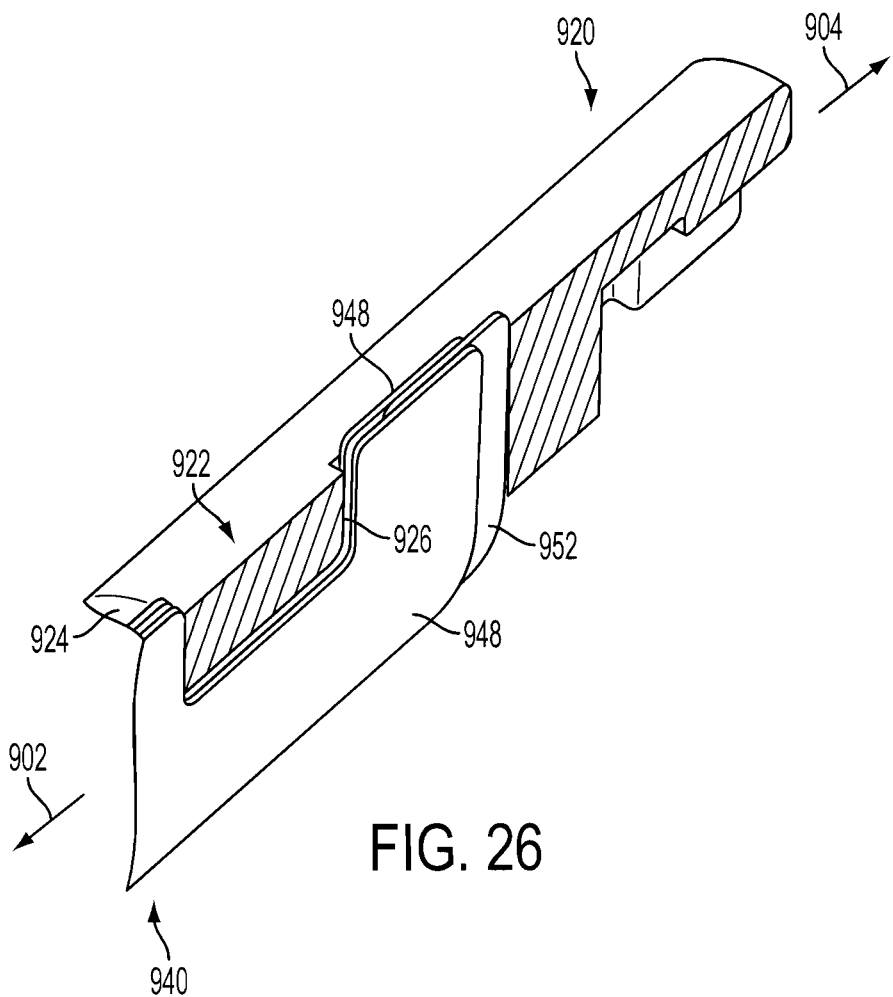
FIGS. 26 and 28 are cross-sectional views of a firing rod operatively coupled to a pusher block in accordance with one non-limiting embodiment.
Figure 27:
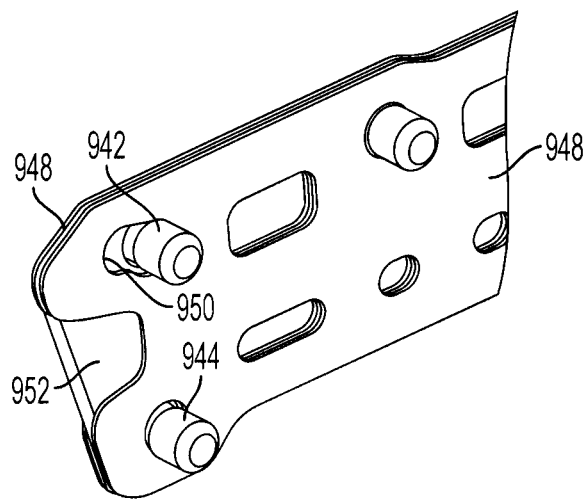
FIGS. 27 and 29 are perspective views of the movable cutting member in accordance with one non-limiting embodiment.
Figure 28:
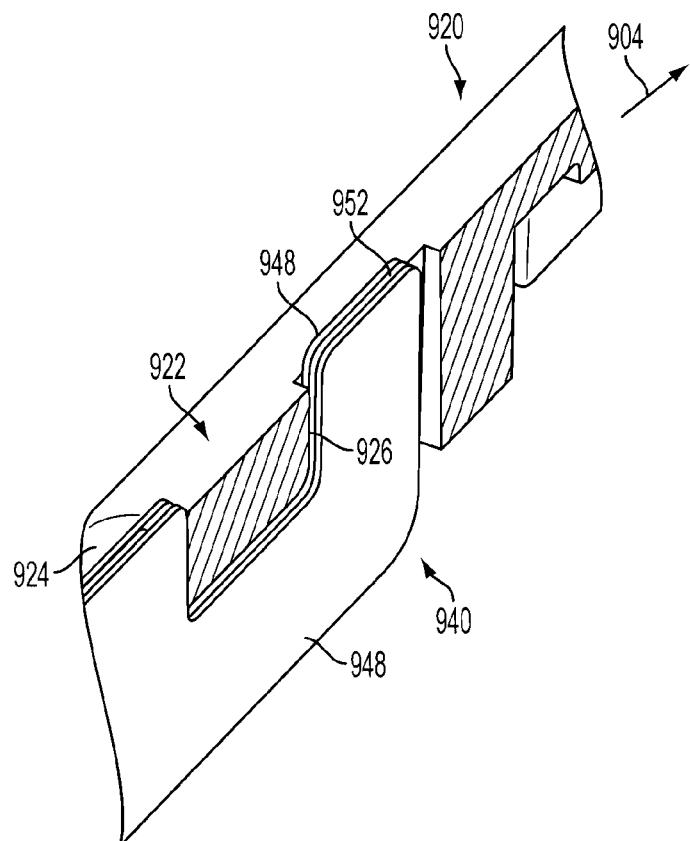
Figure 29:
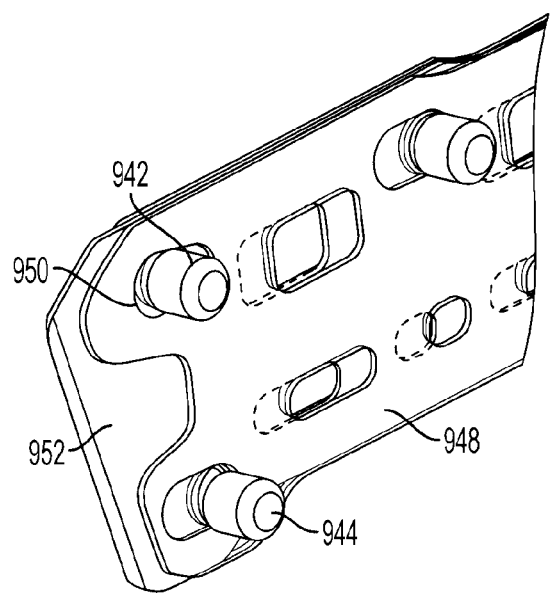

In some embodiments, a pusher block may be used to facilitate the relative translation of the central band 952 and the outer bands 948 during various stages of the operational stroke. FIG. 26 illustrates a cross-sectional view of a firing rod 920 operatively coupled to a pusher block 922 during a cutting stroke. The firing rod 920 may be operatively coupled to a trigger (not shown) of the surgical instrument such that the firing rod 920 may be selectively advanced and/or retracted in the directions indicated by arrows 902 and 904, respectively. The pusher block 922 has a distal face 924 and a proximal face 926. During the cutting stroke (e.g., when the firing rod 920 is advanced in the direction indicated by arrow 902), the three bands of the movable cutting member 940 align on the distal face 924. A perspective view of the movable cutting member 940 during the cutting stroke is shown in FIG. 27. In this position, the vertical separation between the first and second jaw closure pins 942 and 944 is at a minimum distance to generate maximum tissue compression. FIG. 28 illustrates a cross-sectional view of the firing rod 920 during retraction of the movable cutting member 940 (e.g., when the firing rod 920 is retracted in the direction indicated by arrow 904). During retraction, the three bands of the movable cutting member 940 align on the proximal face 926. A perspective view of the movable cutting member 940 during the retraction is shown in FIG. 29. In this position, the vertical separation between the first and second jaw closure pins 942 and 944 is at a maximum distance to provide a reduced amount of tissue compression.

Figure 31A:
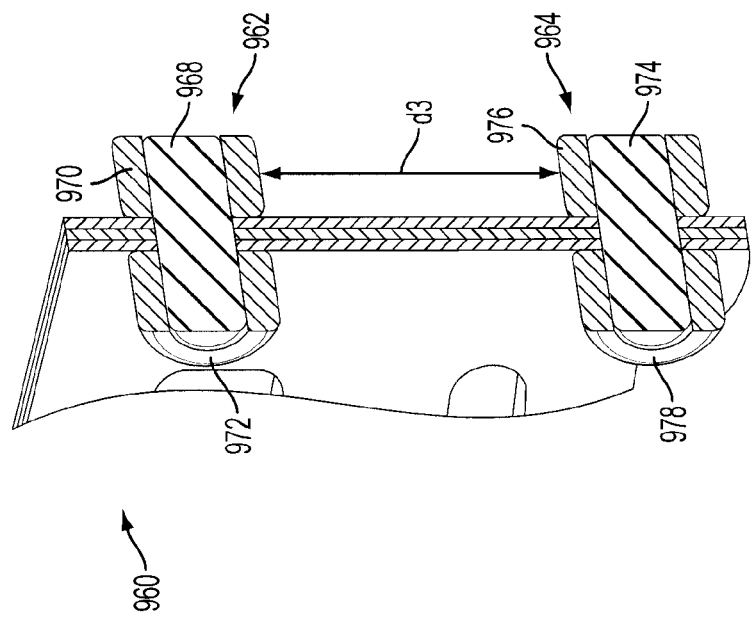
FIG. 31A is a cross-sectional view of the movable cutting member of FIG. 31.
Figure 31:
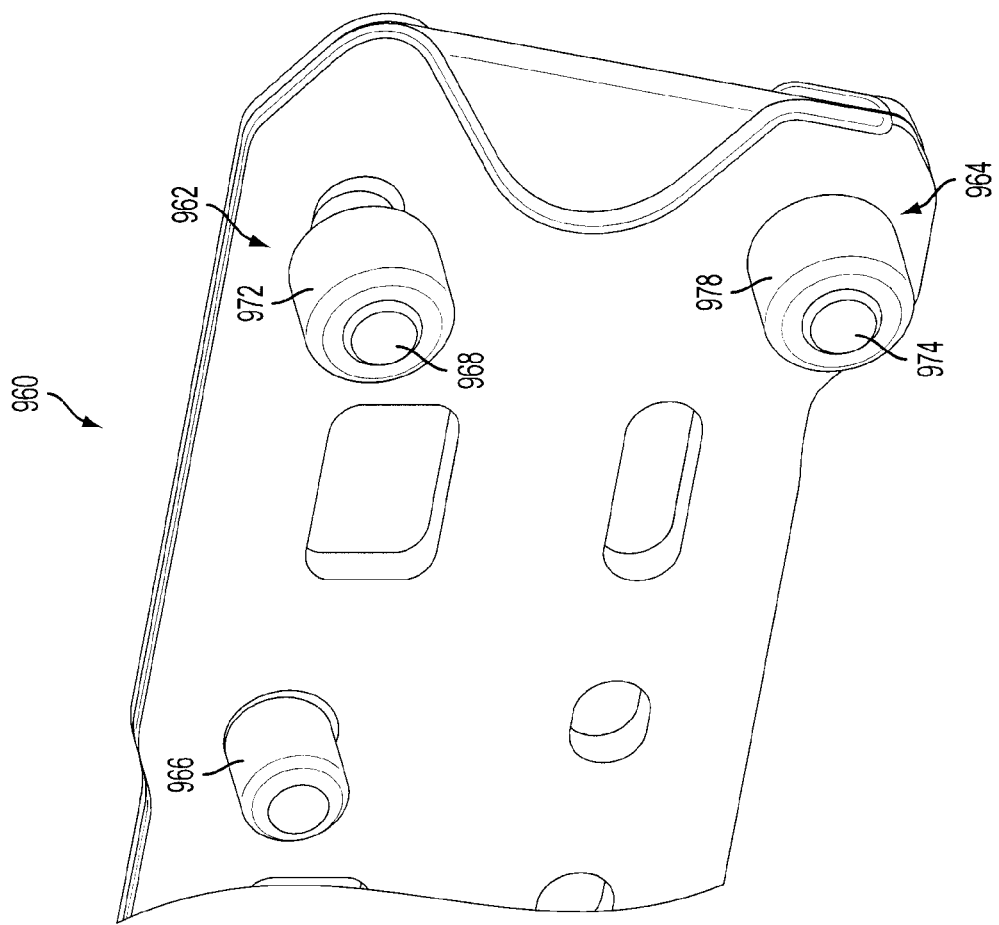
FIG. 31 is a perspective view of the movable cutting member of FIG. 30 in an assembled configuration.

In some embodiments, at least one of the closure pins may be an assembly comprised of two or more individual components. FIG. 30 is a perspective exploded view of a movable cutting member 960 comprising closure pin assemblies. FIG. 31 is a perspective view of the movable cutting member 960 of FIG. 30 in an assembled configuration. FIG. 31A is a cross-sectional view of the movable cutting member 960. In the illustrated embodiment, first and second closure pin 962, 964 are assemblies while proximal pin 966 is unitary. The first closure pin 962 may comprise a shaft 968 and first and second rings 970, 972. The shaft 968 and first and second rings 970, 972 may be manufactured from any suitable material. In one embodiment, the shaft 968 is 17-7PH stainless steel and the first and second rings 970, 972 are an alloy, such as TOUGHMET. The first and second rings 970, 972 may be, for example, press-fit onto the shaft 968. As illustrated, the second closure pin 964 may be assembled similarly to the first closure pin 962. For example, the second closure pin may comprise a shaft 974 and first and second rings 976, 978. As is to be appreciated, during an operational stroke, the rings 970, 972, 976, 978 contact the various closure pin tracks of an associated end effector.

The size of the shafts 968, 974 and the rings 970, 972, 976, 978 may differ based on the size of the end effector. In one embodiment, for example, the shafts 968, 974 have outer diameters of about 0.0400" with a tolerance of +/−0.0002". In one embodiment, for example, the rings 970, 972, 976, 978 have an inner diameter of about 0.0394" with a tolerance of +/−0.0003". In one embodiment, for example, the rings 970, 972, 976, 978 have an outer diameter of about 0.070" with a tolerance of +/−0.0003". In one embodiment, the distance $d_3$ (FIG. 31A) between the first and second closure pins 962, 064 may be about 0.148" with a tolerance of about +/−0.001".

Generally, in accordance with one embodiment, the rings 970, 972, 976, 978 allow for a relatively large outer diameter to capture the closure pins 962, 968 in the tracks of the end effector. Furthermore, the relatively large outer diameters of the rings 970, 972, 976, 978 may prevent the closure pins 962, 968 from cocking within the track which may lead to a jam. If the track is deformed, such as due to high clamp loads, the relatively large diameter of the rings 970, 972, 976, 978 also may assist in ensuring the closure pins 962, 964 remain engaged with the track. Additionally, in some embodiments, the closure pins 962, 964 may be manufactured without a peening process which eliminates a source of process variability.

Figure 32:
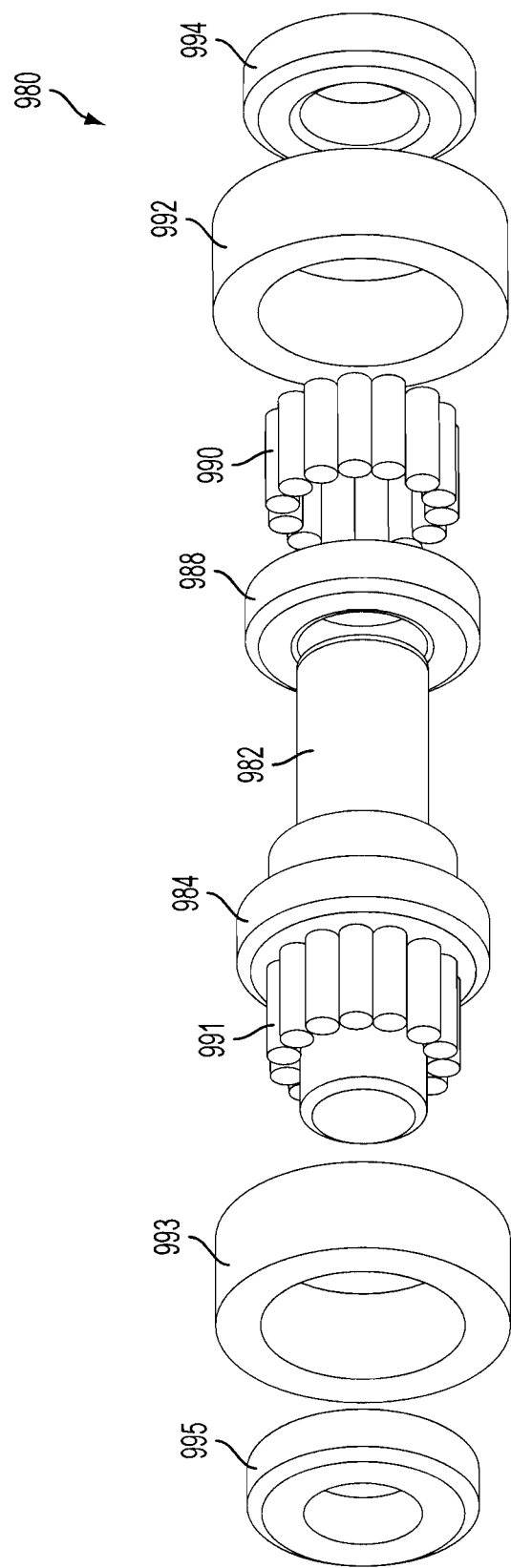
FIG. 32 is an exploded view of a closure pin comprising needle bearings in accordance with one non-limiting embodiment.
Figure 33:
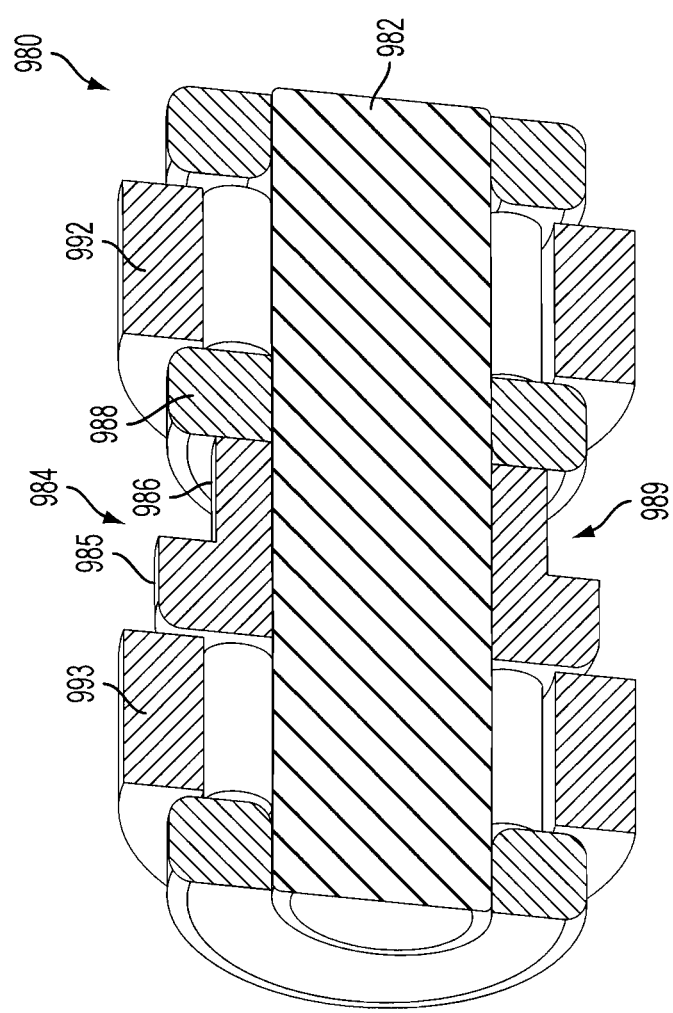
FIG. 33 is a cross-sectional view of the assembled closure pin of FIG. 32.

In some embodiments, the closure pins may incorporate bearings to reduce frictional concerns while firing. FIG. 32 is an exploded view of a closure pin 980 comprising needle bearings. FIG. 33 is a cross-sectional view of the assembled closure pin 980. In one embodiment, the closure pin 980 comprises a shaft 982. The shaft may be, for example, about 1 mm in diameter. The closure pin 980 may comprise a stepped collar 984 having a first portion 985 and a second portion 986. The outer diameter of the first portion 985 may be larger than the outer diameter of the second portion 986. The closure pin 980 may also comprise an inner collar 988. When assembled, the inner collar 988 and the stepped collar 984 may define a notch 989. As is to be appreciated, the notch 989 receives an associated movable cutting member (not illustrated). The closure pin 980 may also comprise a first and second set of needle bearings 990, 991. In one embodiment, each needle of the needle bearings 990, 991 is about 0.010" in diameter. First and second wheels 992, 993 may receive the first and second set of needle bearings 990, 991, respectively. First and second end collars 994, 995 may be attached to the shaft 982 using a press-fit engagement, for example.

When coupled to a movable cutting member of an end effectors, the wheels 992, 993 of the closure pin 980 may engage a track of the end effector. As the movable cutting member is translated through the end effector, the wheels 992, 993 may rotate with respect to the shaft 968 via the first and second sets of needle bearings 990, 991. Accordingly, frictional forces that may be experienced during an operational stroke may be reduced.

Figure 34:
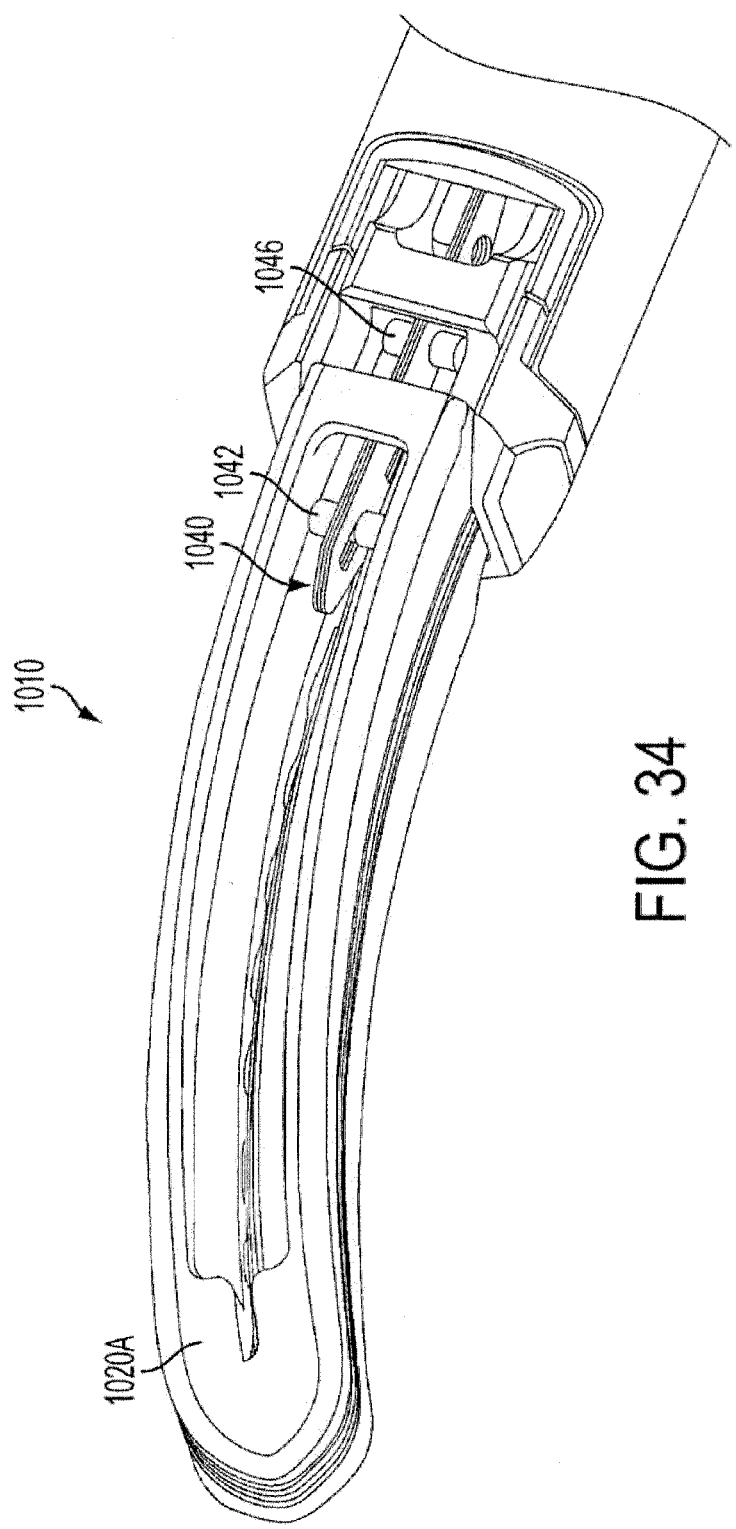
FIG. 34 is a perspective view of an end effector in accordance with one non-limiting embodiment.
Figure 35:
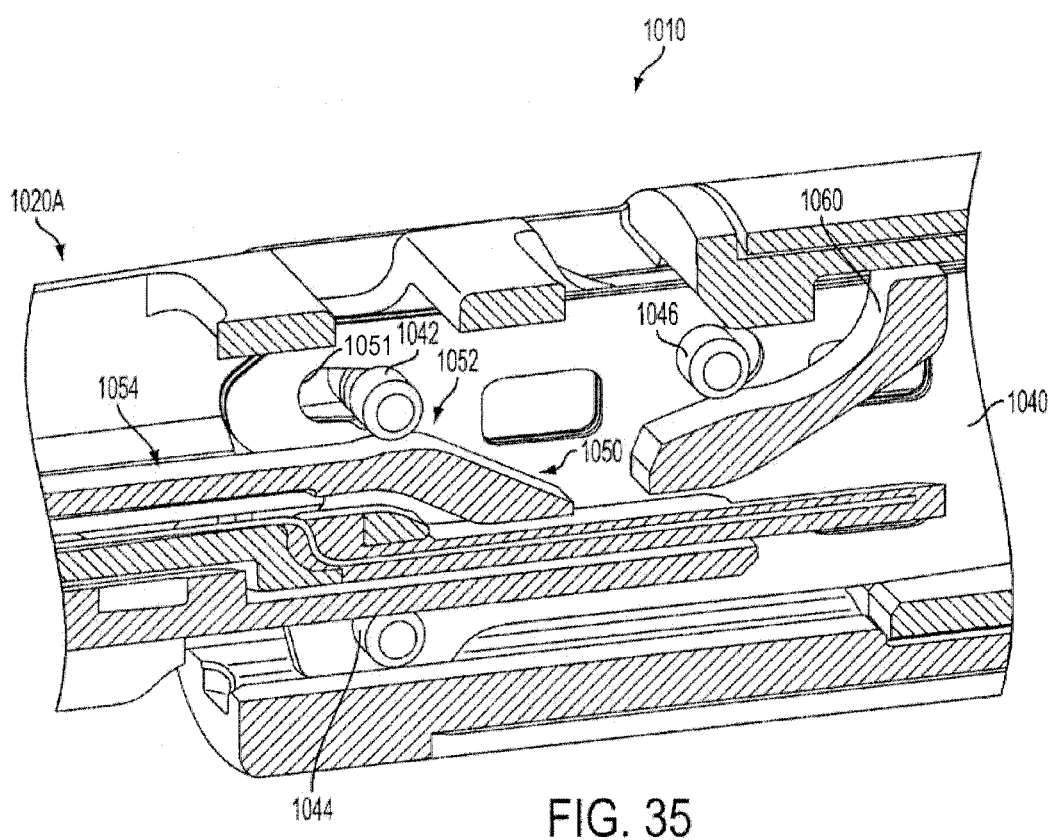
FIG. 35 is a cross-sectional view of a portion of the end effector shown in FIG. 34.

In some embodiments, the end effector may comprise a variety of features that collectively assist in reducing the force to fire and/or the force to return. FIG. 34 is a perspective view of an end effector 1010 in accordance with one non-limiting embodiment. FIG. 35 is a cross-sectional view of a portion of the end effector 1010. As illustrated in FIGS. 30 and 31, the moveable cutting member 1040 has a first jaw closure pin 1042 that translates relative to a second jaw closure pin 1044 via an oblique slot 1051 to alter the distance of separation between the two pins. Additionally, the first jaw 1020A comprises a multi-sloped track to engage the first jaw closure pin 1042 and the proximal pin 1046. As illustrated, the first jaw 1020A comprises an opening ramp 1060, a closure ramp 1050, a ridge 1052, and a ramped section 1054 similar to the end effector 610 shown in FIG. 19

Figure 36:
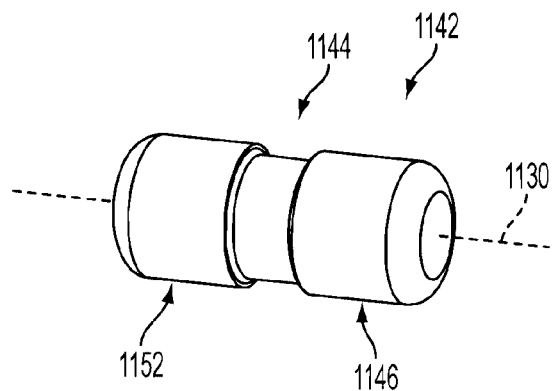
FIG. 36 illustrates a stepped pin in accordance with one non-limiting embodiment.
Figure 37A:
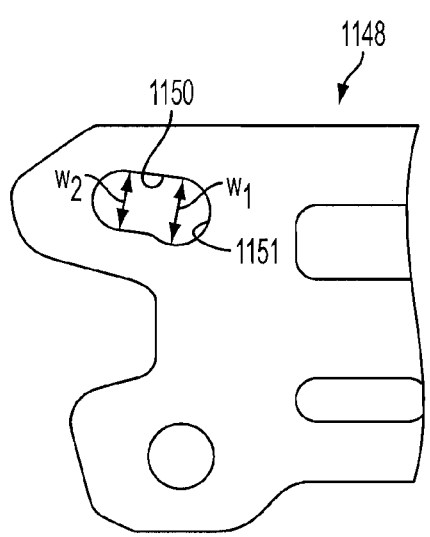
FIGS. 37A and 37B illustrate outer bands of a movable cutting member in accordance with one non-limiting embodiment.
Figure 37B:
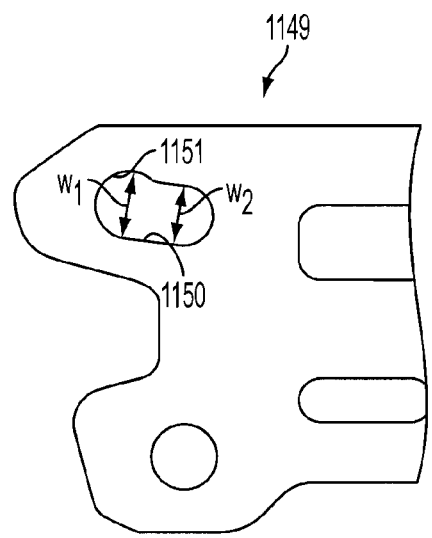
Figure 38A:
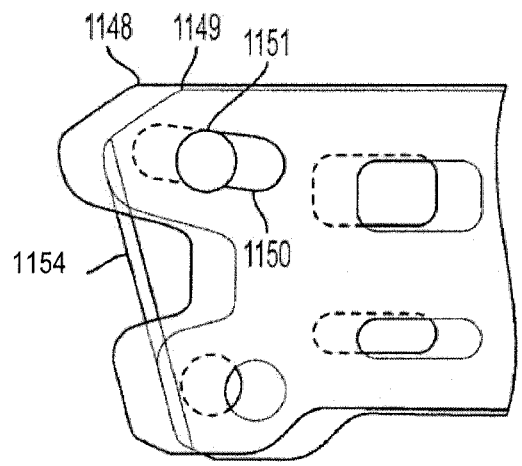
FIGS. 38A and 38B illustrate the outer bands of FIGS. 37A and 37B in an assembly position.
Figure 38B:
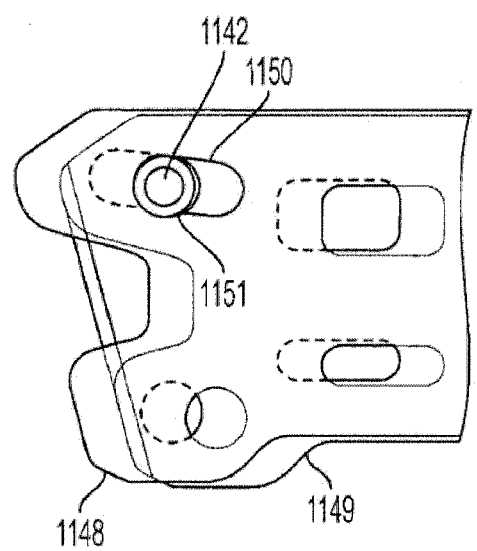
Figure 39:
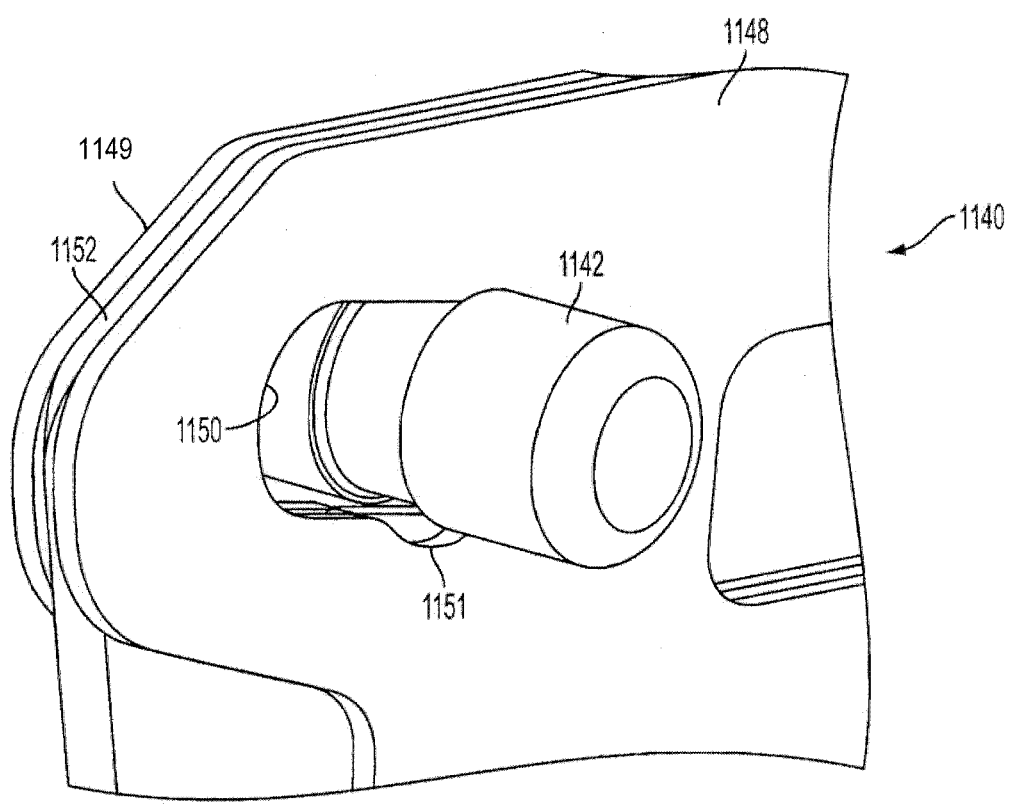
FIG. 39 is a perspective view of the top distal end of the moveable cutting member after a first jaw closure pin has been affixed.

The various pins associated with the moveable cutting member may be affixed using any suitable technique. In one embodiment the pins may be secured to a multi-banded movable cutting member using a key slot technique. For such embodiments, a stepped pin 1142, as illustrated in FIG. 36 may be used. The stepped pin 1142 has a longitudinal axis 1130 at least two portions along the longitudinal axis 1130 that have different outer diameters. In one embodiment, a middle portion 1144 has a smaller diameter than a first outer portion 1146 and a second outer portion 1152. FIGS. 37A and 37B show outer bands 1148 and 1149 according to one non-limiting embodiment. Each outer band 1148 and 1149 has a slot 1150 with a larger aperture 1151 at one end. The aperture 1151 on the outer band 1148 is on the opposite end of the slot 1150 as compared to the outer band 1149. The apertures 1151 have width of $w_1$ and the slots 1150 have a width of $w_2$. The width $w_2$ may be slight greater than the outer diameter of one of the first outer portion 1146 and a second outer portion 1152 of the stepped pin 1142. The width $w_1$ may be slightly greater than the outer diameter of the a middle portion 1144 but less than the diameter of the first and second outer portions 1146 and 1152. To assemble the moveable cutting member, two outer bands 1148 and 1149 are positioned such that the apertures 1151 are aligned. FIG. 38A shows two bands 1148 and 1149 sandwiching a central band 1154 with their apertures 1151 aligned. To affix the stepped pin 1142 it is inserted through the aligned apertures 1151 (as shown in FIG. 38B) and the bands 1148, 1149 are pulled in opposite directions so that the narrower section of the slot 1150 traps the stepped pin 1142 in place. FIG. 39 is a perspective view of the top distal end of the moveable cutting member 1140 after the first jaw closure pin 1142 has been affixed.

Figure 40:
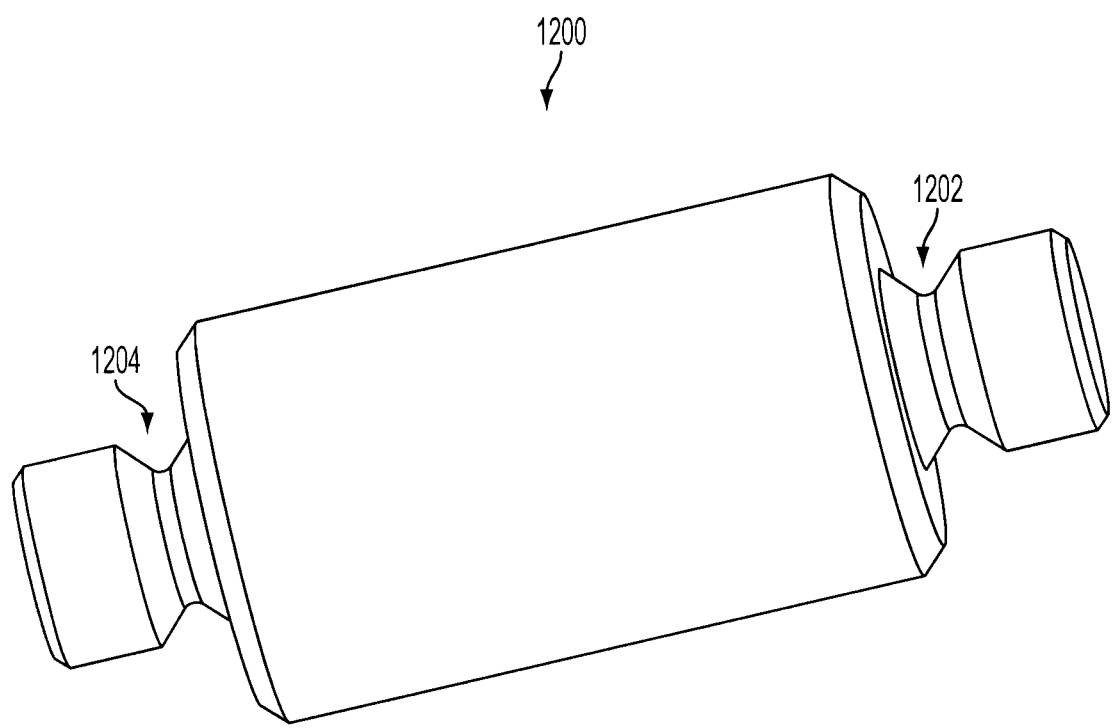
FIG. 40 illustrates a shear pin in accordance with one non-limiting embodiment.
Figure 41:
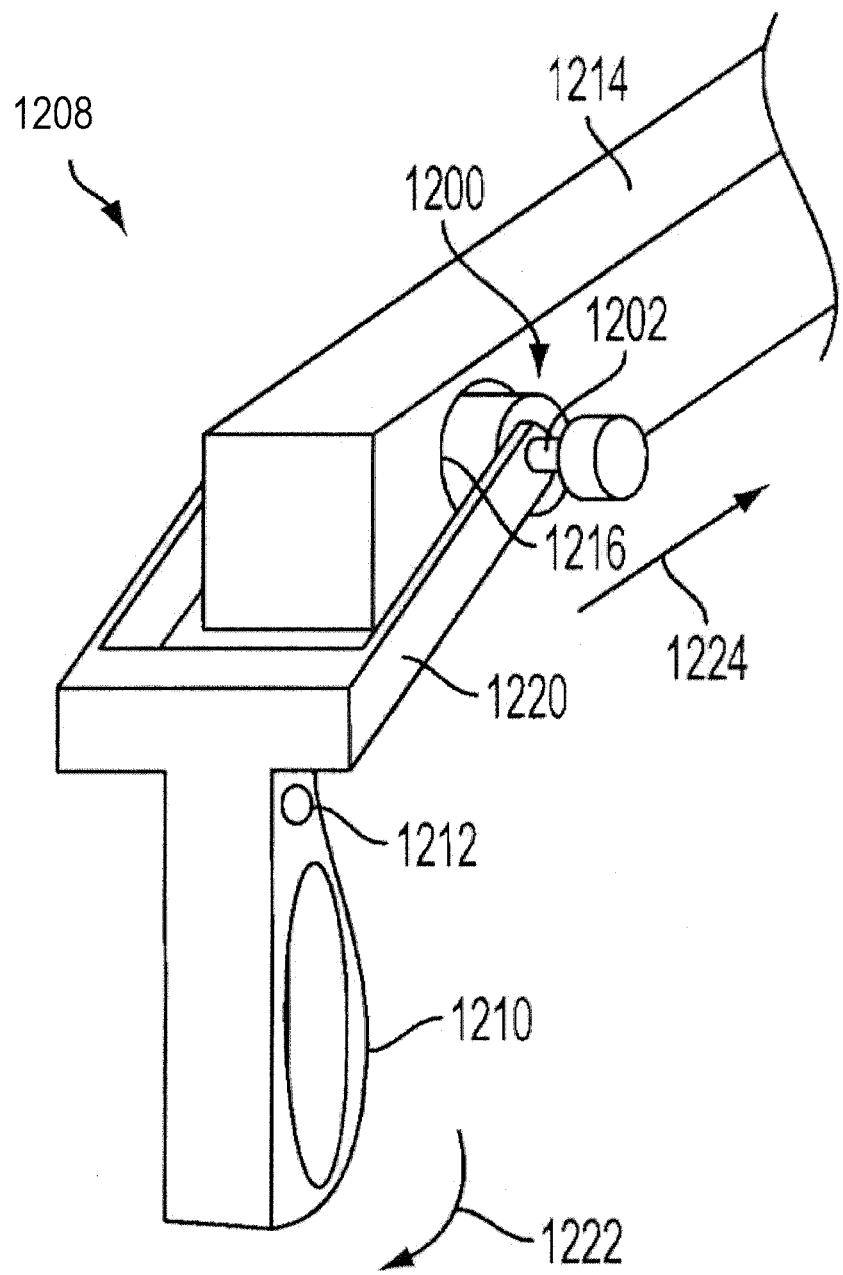
FIG. 41 illustrates a simplified version of a trigger assembly that includes a shear pin in accordance with one non-limiting embodiment.

During certain operational conditions, a surgical instrument may become overloaded. For example, if large vessels or large tissue bundles are being sealed and cut, the force necessary to clamp the jaws and distally drive the cutting element may overload various components of the device. In one embodiment, in order to prevent an overload condition of the device, a shear pin may be used which intentionally fractures when the force reaches a load threshold. FIG. 40 shows a shear pin 1200 in accordance with one non-limiting embodiment. The shear pin 1200 may be manufactured from or comprise any suitable material, such as aluminum (e.g., aluminum alloy 2024) or steel, for example. In one embodiment, the shear pin 1200 may shear in two points during an overloaded condition. A first shear groove 1202 is positioned at one end of the shear pin 1200 and a second shear groove 1204 is positioned at the other end of the shear pin 1200. As is to be appreciated, a single shear groove located at any suitable position may be used in some embodiments. The size of shear pin 1200 may be determined by application and operational thresholds. In some embodiments, the shear pin 1200 may shear at about 60 lbf, which is lower than the force that could damage components of an associated surgical instrument. The shear pin can be assembled in the trigger assembly, allowing free motion of the trigger after shear occurs. FIG. 41 is a simplified version of a trigger assembly 1208 that includes a shear pin 1200. A trigger 1210 is pivotable about pivot 1212 to impart linear movement upon the firing rod 1214. The firing rod 1214 may be operatively coupled to an end effector (not shown) at its distal end. The firing rod 1214 defines a bore 1216 that receives the shear pin 1200. The trigger 1210 is coupled to a cradle 1220 which is operatively coupled to the shear groove 1202 of the shear pin 1200. Force from the trigger 1210 is delivered to the end effector (not shown) through the shear pin 1200. The trigger 1210 may, for example, distally advance a knife in the end effector. During non-overloaded conditions, rotation of the trigger 1210 in the direction indicated by arrow 1222 cause the firing rod 1214 to translate distally (e.g., in the direction indicated by arrow 1224). During an overload event, however, the force delivered to the shear groove 1202 by the cradle 1220 will shear the shear pin 1200 at the shear grove 1202 and de-couple the trigger 1210 from the firing rod 1214.

Figure 42:
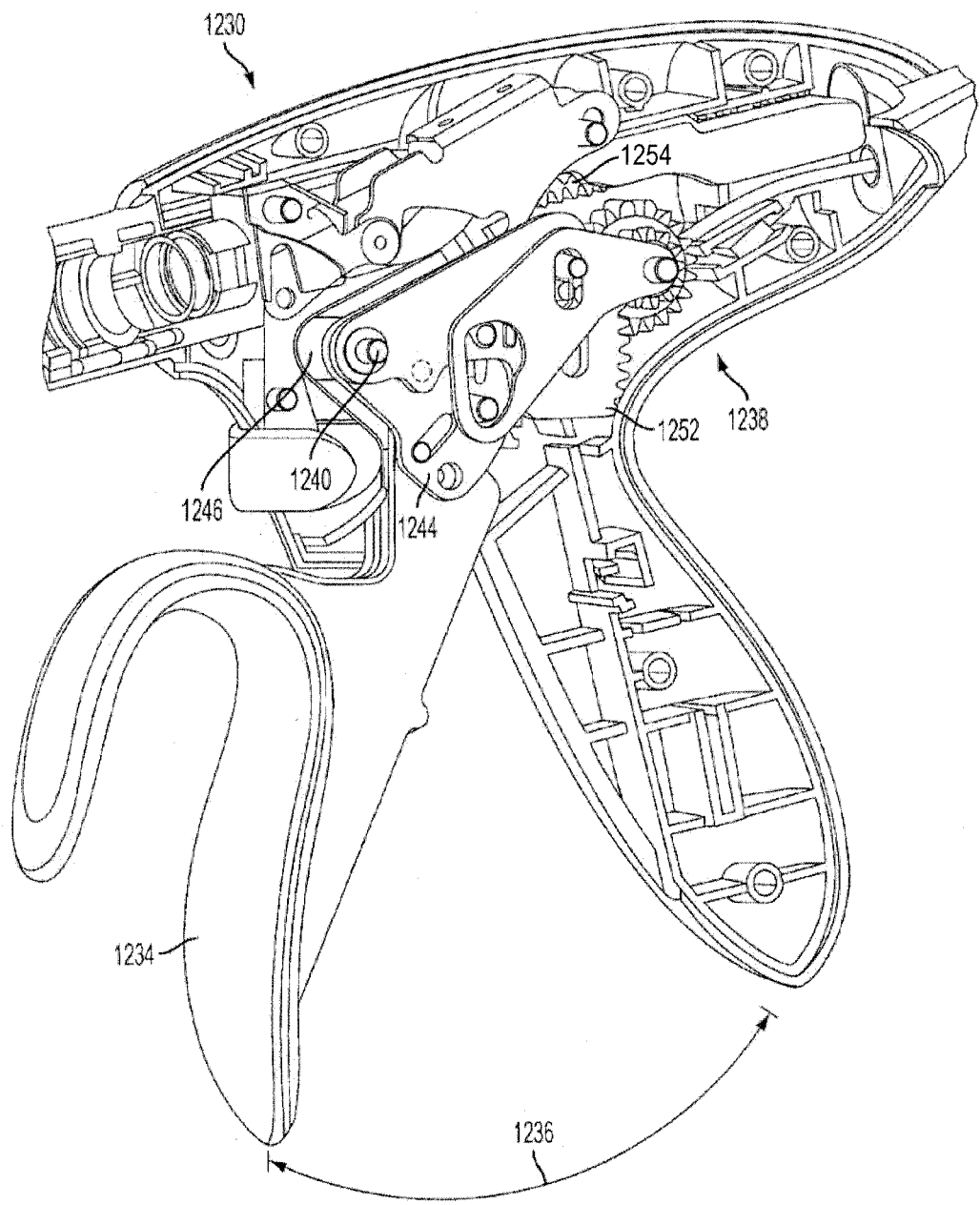
FIG. 42 illustrates a surgical instrument in accordance with one non-limiting embodiment with part of the housing removed to show various internal components.
Figure 43:
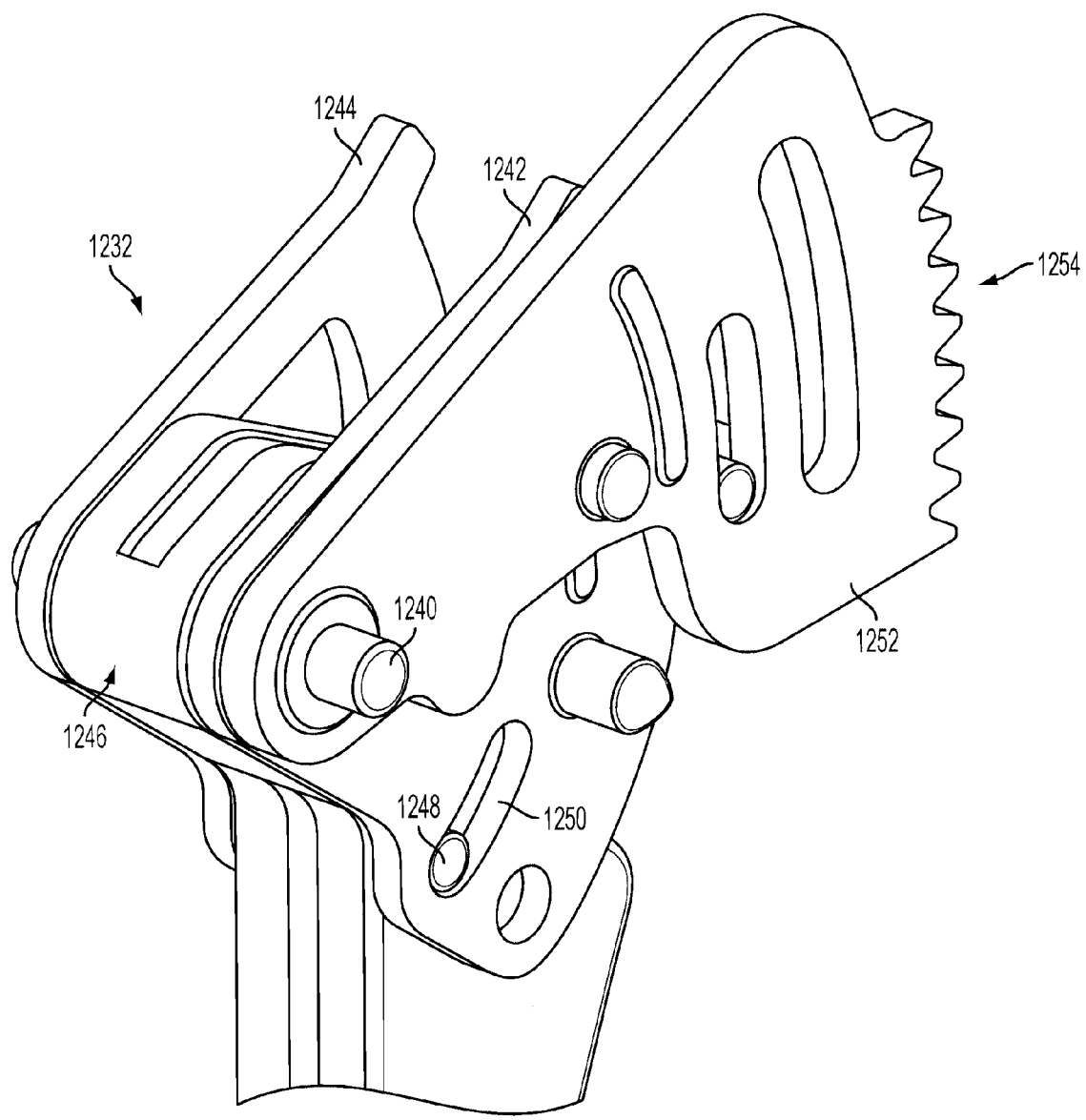
FIG. 43 is an enlarged view of a portion of a trigger assembly with various components removed for clarity.
Figure 44:
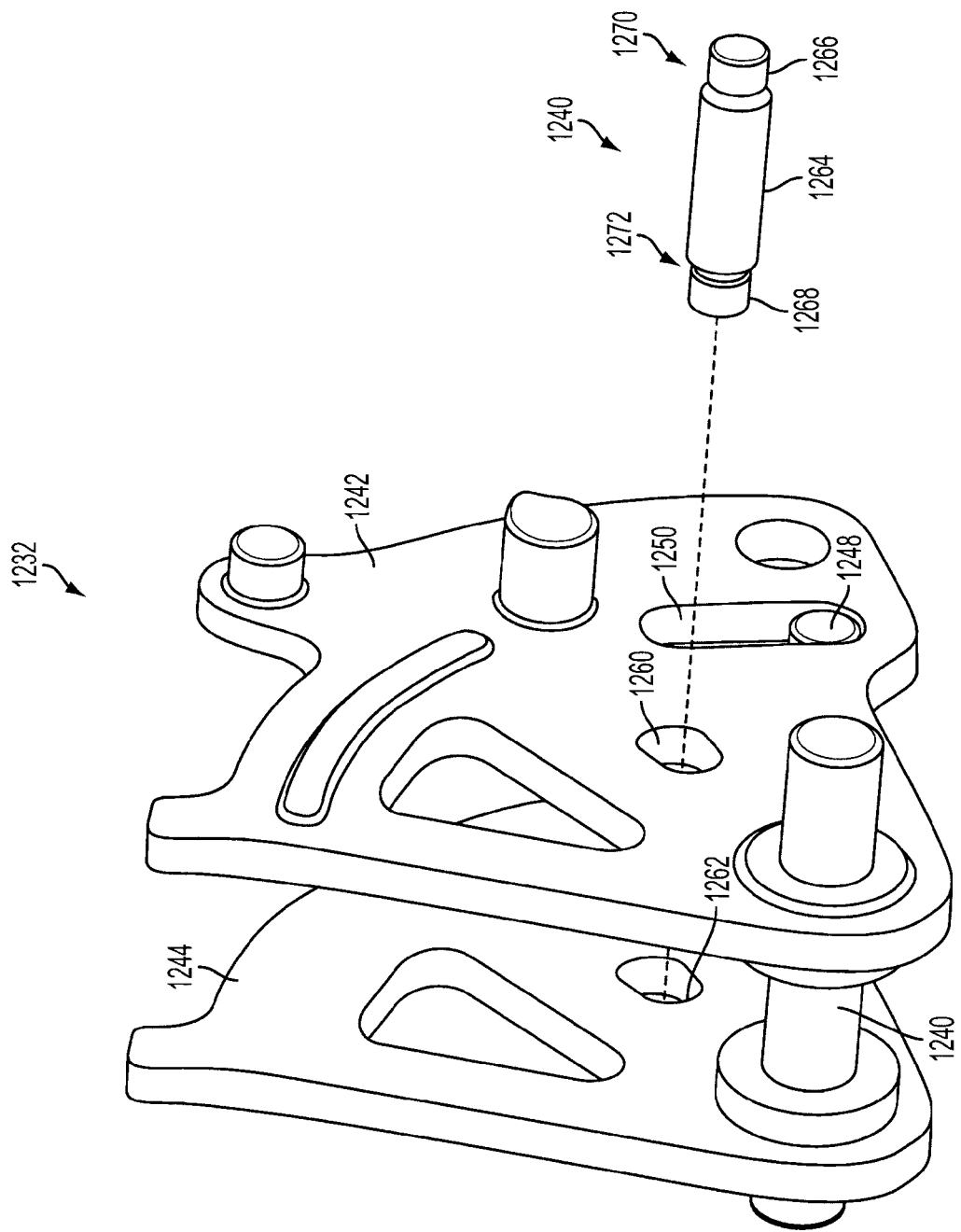
FIG. 44 is an exploded view of various components of the trigger assembly of FIG. 43 with various components removed for clarity.

FIG. 42 illustrates a surgical instrument 1230 with part of the housing removed to show various internal components. The surgical instrument 1230 incorporates a shear pin 1240 (FIG. 44) as an overload member. FIG. 43 is an enlarged view of a portion of the trigger assembly 1232 with various components removed for clarity. FIG. 44 is an exploded view of various components of the trigger assembly 1232 with various components removed for clarity. Referring to FIGS. 42-44, the surgical instrument 1230 generally may operate similar to previously discussed embodiments. For example, movement of a trigger 1234 along a path 1236 may actuate an end effector (not shown). For example, the end effector may have jaws through which a knife is translated. The actuation of the end effector may be driven by a gear assembly 1238 which is operatively coupled to the trigger 1234 and a rack 1240. The trigger assembly 1232 may pivot about a pivot pin 1240 when an operator moves the trigger 1234 along the path 1236. The trigger assembly may comprise a first side trigger plate 1242 and a second side trigger plate 1244 with a central trigger plate 1246 disposed therebetween. The central trigger plate 1246 may be coupled to the trigger 1234. As discussed in more detail below, a return pin 1248 may be coupled to the central trigger plate 1246 and ride in a return slot 1250 defined by the first side trigger plate 1242. The second side trigger plate 1244 may define a slot similar to the return slot 1250 and configured to receive a portion of the return pin 1248. An actuation plate 1252 may also pivot about the pivot pin 1240 upon actuation of the trigger 1234 such that a rack 1254 engages the gear assembly 1238 and ultimately actuates the end effector.

As shown in FIG. 44, the first and second side trigger plates 1242, 1244 may each define first and second shear pin bores 1260, 1262, respectively. The shear pin 1240 may be received by the first and second shear pin bores 1260, 1262. When assembled, a central portion 1264 of the shear pin 1240 may engage a bore of the central trigger plate 1246 (FIG. 43). The shear pin 1240 may have first and second ends 1266, 1268 that engage the first and second side trigger plates 1242, 1244, respectively. The shear pin 1240 may define a first shear groove 1270 positioned intermediate the first end 1266 and the central portion 1264 and a second shear groove 1272 positioned intermediate the central portion 1264 and the first end 1266.

Referring now to FIGS. 42-44, in one embodiment, the surgical instrument 1230 may be used to distally advance a knife in an end effector comprising jaws for grasping tissue (not shown). When the load becomes too high, the first and second side trigger plates 1242, 1244 exert excess force onto the first and second ends 1266, 1268 of the shear pin 1240. Eventually, the shear pin 1240 fractures at one or both of the shear grooves 1270, 1272. Once the shear pin fractures 1240, the trigger 1234 can no longer push the knife forward due to the decoupling of the first and second side trigger plates 1242, 1244 from the central trigger plate 1246. After the shear pin 1240 fractures, however, the return pin 1248 allows the trigger 1234 to pull the knife back through its engagement with the return slot 1250. Therefore, in one embodiment, even though the trigger 1234 can no longer distally advance the knife, the trigger 1234 can still be used to can retract the knife via the coupling of the return pin 1248 with the first and second side trigger plates 1242, 1244. Once the knife if retracted, the jaws of the end effector may be opened and the tissue removed. Thus, in one embodiment, after an overload condition has been experienced, the trigger 1234 is prohibited from pushing the knife forward but still may return the knife to disengage the end effector from the captured tissue. While the shear pin 1240 is illustrated in the context of an electrosurgical instrument, it may also be used with other types of surgical instruments, such as an endocutter for clamping, severing and stapling tissue, for example.

In some embodiments, other features may be incorporated into the surgical device to limit the maximum amount of force that may be applied to various components of the end effector. In one embodiment, for example, a spring, or a series of springs, may serve as compression means to limit the maximum force applied to the end effector. The springs may be preloaded with the maximum desired compression loading amount and only translate (e.g., compress) when an overload force is applied. The springs may be axial in nature and may be any suitable type, such as compression type, belleville type, die spring, or other type of linear spring member. During normal operational loading, the compression member generally acts as a solid member. The compression force is passed directly from a trigger to the moveable cutting member via a firing rod, for example. When an overload force is applied, however, the compression member will compress to absorb the excess force and limit the amount of force that is translated to the end effector. In one embodiment, the amount of force necessary to compress the compression member is less than the amount of force that would cause a component of the end effector to fail.

Figure 45:
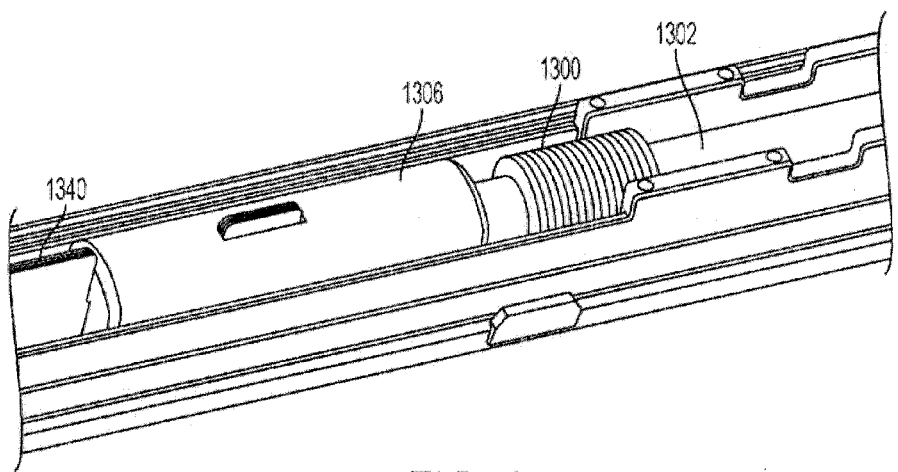
FIG. 45 illustrates a compression member mounted internal to a drive shaft of a surgical instrument in accordance with one non-limiting embodiment.
Figure 45A:
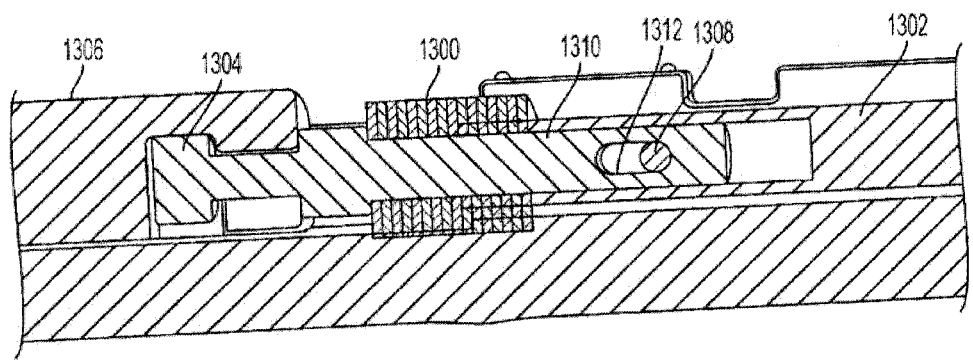
FIG. 45A is a cross-sectional view of FIG. 45.

FIG. 45 shows a compression member 1300 mounted internal to a drive shaft of a surgical instrument in accordance with one non-limiting embodiment. A firing rod 1302 transfers a force from a trigger (not shown) to a movable cutting member 1340. The compression member 1300 is illustrated as a series of belleville washers, although any suitable compression member may be used. FIG. 45A is a cross-sectional view of FIG. 45. A plunger 1304 is operatively engaged with a pusher block 1306. When an overload force is applied, the firing rod 1302 will translate relative to the plunger 1304 due to the compression of the compression member 1300. In some embodiments, the firing rod 1302 may be coupled to a pin 1308 and the plunger 1304 may be operatively coupled to a member 1310. The member 1310 can define a slot 1312 to receive the pin 1308. During overload conditions, the pin 1308 may translate relative to the slot 1312 when the compression member 1300 compresses. Accordingly, the longitudinal length of the slot 1312 may limit the relative translation of the firing rod 1302 to the plunger 1304.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision incisions (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A surgical instrument for supplying energy to tissue, comprising:
   a handle, comprising:
      a trigger; and
      an electrical input;
   a shaft extending from the handle, wherein the shaft comprises a conductor, and wherein the trigger is selectively actuatable to electrically couple the electrical input and the conductor; and
   an end effector defining a longitudinal axis, comprising:
      a first jaw member;
      a second jaw member, wherein at least one of the first jaw member and the second jaw member is movable relative to the other of the first jaw member and the second jaw member between an open and closed positions to clamp tissue intermediate the first jaw member and the second jaw member in the closed position;

the first and second jaw members defining a channel;

a cutting member including a distal end, wherein the cutting member is sized and configured to fit at least partially within the channel, the cutting member configured to translate along the channel between a retracted position and a fully advanced position, the cutting member comprising at least a first, second, and third bands, wherein the second band is disposed intermediate the first and third bands and comprises a sharp distal cutting element; and at least one compression element extending from the cutting member, wherein the at least one compression element engages one of the first and second jaw members to move the first and second jaw members from the open position to the closed position when the cutting member translates with respect to the first jaw member beyond the retracted position.

2. The surgical instrument of claim 1, the first jaw member comprises a first track and the second jaw member comprises a second track, wherein the at least one compression element comprises a first compression element that moves in the first track and a second compression element that moves in the second track.

3. The surgical instrument of claim 2, wherein the first track comprises a first distal stop to engage the first compression element and the second track comprises a second distal stop to engage the second compression element.

4. The surgical instrument of claim 2, wherein the channel extends in a distal direction further than the first and second tracks.

5. The surgical instrument of claim 1, wherein the first and third bands comprise a funneling portion proximate to the sharp distal cutting element.

* * * * *